(12) United States Patent
Rinaldi et al.

(10) Patent No.: US 12,331,101 B2
(45) Date of Patent: Jun. 17, 2025

(54) TREATMENT OF SPINAL AND BULBAR MUSCULAR ATROPHY

(71) Applicant: Oxford University Innovation Limited, Oxford (GB)

(72) Inventors: Carlo Rinaldi, Oxford (GB); Wooi Fang Lim, Oxford (GB); Matthew Wood, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 0 days.

(21) Appl. No.: 17/765,116

(22) PCT Filed: Oct. 2, 2020

(86) PCT No.: PCT/GB2020/052435
§ 371 (c)(1),
(2) Date: Mar. 30, 2022

(87) PCT Pub. No.: WO2021/064421
PCT Pub. Date: Apr. 8, 2021

(65) Prior Publication Data
US 2022/0380438 A1   Dec. 1, 2022

(30) Foreign Application Priority Data
Oct. 3, 2019  (GB) .................. 1914296.7

(51) Int. Cl.
| C12N 15/11 | (2006.01) |
| A61K 48/00 | (2006.01) |
| A61P 21/00 | (2006.01) |
| C07K 14/075 | (2006.01) |
| C07K 14/72 | (2006.01) |
| C12N 15/86 | (2006.01) |

(52) U.S. Cl.
CPC ........ *C07K 14/721* (2013.01); *A61K 48/0058* (2013.01); *A61P 21/00* (2018.01); *C07K 14/075* (2013.01); *C12N 15/86* (2013.01)

(58) Field of Classification Search
CPC ............... A61K 48/00; A61K 48/0066; A61K 31/7088; C12N 15/63; C12N 15/67
See application file for complete search history.

(56) References Cited

U.S. PATENT DOCUMENTS

| 2002/0165381 A1 | 11/2002 | Ahrens-Fath et al. |
| 2010/0286229 A1* | 11/2010 | Gurova ............. A61P 35/00 435/254.2 |
| 2015/0045416 A1* | 2/2015 | Mitrani-Rosenbaum ............. A61P 21/00 435/320.1 |
| 2015/0252426 A1* | 9/2015 | Joseph ................ A61K 45/06 435/6.12 |
| 2018/0311380 A1* | 11/2018 | Gao ........................ C12N 5/10 |
| 2018/0334677 A1* | 11/2018 | Freedman .......... A61K 31/7125 |

FOREIGN PATENT DOCUMENTS

| JP | 2003000273 A | 1/2003 |
| JP | 2003 102333 A | 4/2003 |
| WO | 92/06180 A1 | 4/1992 |
| WO | 94/08598 A1 | 4/1994 |
| WO | WO-2019023651 A2 * | 1/2019 ........... A61K 31/445 |

OTHER PUBLICATIONS

Monks et al., Overexpression of wild-type androgen receptor in muscle recapitulates polyglutamine disease, PNAS, vol. 104, pp. 18259-18264. (Year: 2007).*
Monks et al., Androgen receptor and Kennedy disease/spinal bulbar muscular atrophy, Hormones and Behavior, vol. 53, pp. 729-740. (Year: 2008).*
International Search Report and Written Opinion for WO 2021/064421 (PCT/GB2020/052435), dated Dec. 3, 2020, pp. 1-20.
UK Search Report for GB 1914296.7, dated Apr. 9, 2020, p. 1.
Isabelle Ahrens-Fath et al: "Androgen receptor function is modulated by the tissue-specific AR45 variant: Androgen receptor variant form", FEBS Journal, vol. 272, No. 1, Dec. 2, 2004 (Feb. 12, 2004), pp. 74-84.
Naemeh Pourshafi E et al: "MiR-298 Counteracts Mutant Androgen Receptor Toxicity in Spinal and Bulbar Muscular Atrophy", Molecular Therapy, vol. 24, No. 5, May 1, 2016 (May 1, 2016), pp. 937-945.
Maria Pennuto et al: "From gene to therapy in spinal and bulbar muscular atrophy: Are we there yet?", Molecular and Cellular Endocrinology., vol. 465, Apr. 1, 2018 (Apr. 1, 2018), pp. 113-121.
Database Geneseq [Online] Dec. 18, 2003, "Human androgen receptor-related protein.", Database accession No. ADC55548.
Database Geneseq [Online] Jan. 25, 2018 (Jan. 25, 2018), Human AR gene splice variant AR45 specific probe, SEQ 71., Database accession No. BER87864.
Database Geneseq [Online] Dec. 15, 2016 (Dec. 15, 2016), Human AR gene quantitative PCR primer AR45_FW, SEQ ID 5., Database accession No. BDI09323.
Weiss et al., Phylogenetic conservation of the androgen receptor AR45 variant form in placental mammals, Gene, 399 (2), 2007, pp. 105-111.
Grunseich et al., Lancet Neurol. Dec. 2018;17:1043-1052.
Cunningham et al., Science 244, 1081-1085 (1989).
Wang et al., Gene Therapy 15, 1489-1499 (2008).
Goldspiel et al., Clinical Pharmacy 12:488-505 (1993).
Wu and Wu, Biotherapy 3:87-95 (1991).
Tolstoshev, Ann. Rev. Pharmacol. Toxicol. 32:573-596 (1993).
Mulligan, Science 260:926-932 (1993).

(Continued)

*Primary Examiner* — Dana H Shin
(74) *Attorney, Agent, or Firm* — Thomas |Horstemeyer, LLP

(57) ABSTRACT

The present invention relates to treatment of AR-related disorders by modulating the levels of AR2, which is a naturally occurring AR variant and is capable of modulating AR transcriptional activity.

5 Claims, 18 Drawing Sheets
Specification includes a Sequence Listing.

(56) References Cited

OTHER PUBLICATIONS

Morgan and Anderson, Ann. Rev. Biochem. 62: 191-217 (1993).
May, Tibtech 11(5): 155-215 (1993).
Wu and Wu, J Biol. Chem. 262:4429-4432 (1987).
Koller and Smithies, Proc. Natl. Acad. Sci. USA 86:8932-8935(1989).
Zijlstra et al., Nature 342:435-438 (1989).
Stemple and Anderson, Cell 71 :973-985 (1992).
Rheinwald, Meth. Cell Bio. 21A:229 (1980).
Pittelkow and Scott, Mayo Clinic Proc. 61 :771 (1986).
Davey and Grossmann, Clin. Biochem. Rev. 37(1) (2016).
Shukla et al., Andrology, 4, 366-381 (2016).
Altschul, J Mol Evol. Mar. 1993;36(3):290-300.
Altschul, J Mol Biol. Oct. 5, 1990;215(3):403-10.
Henikoff and Henikoff (1992) PNAS 15:10915-9.
Karlin and Altschul (1993) PNAS 15:5873-7.
Devereux et al., (1984) Nucleic Acids Res. 12:387-395.
Schmidt, et al., Methods 48, 240-248 (2009).
Burger et al., Nucleic Acids Res. 47, 3467-3484 (2019).
Haraszti et al., Nucleic Acids Res. 45, 7581-7592 (2017).
Patro et al., Nat. Methods 14, 417-419 (2017).
Boneson et al., F1000 Research 4, 1521 (2016).
Sergushichev et al., bioRxiv 060012 (2016).
Turanov et al., Nat. Biotechnol. 36, 1164-1173 (2018).
Dehm et al., Alternatively spliced androgen receptor variants, Endocrine-Related Cancer (2011) 18, R183-R196.
Castanotto et al., A Multifunctional LNA Oligonucleotide-Based Strategy Blocks AR Expression and Transactivation Activity in PCa Cells, Molecular Therapy: Nucleic Acids, vol. 23 Mar. 2021.
Japanese Office Action for Patent Application No. 2022-520403, dated Aug. 6, 2024, pp. 1-14 (Translation Included).
Changxue Lu, Jun Luo, "Decoding the androgen receptor splice variants", Transl Androl Urol, 2013, vol. 2, No. 3, pp. 178-186.
Lim et al., "Gene therapy with AR isoform 2 rescues spinal and bulbar muscle atrophy phenotype by modulating AR transcriptional activity", Sci. Adv. 2021 (Aug. 20, 2021), pp. 1-30.
He et al., "Androgen receptor with short polyglutamine tract preferably enhances Wnt/β-catenin-medicated prostatic tumorigenesis", Oncogene (2020) 39:3276-3291, Springer Nature, pp. 1-16.
Katsuno et al., "Efficacy and safety of leuprorelin in patients with spinal and bulbar muscular atrophy (JASMITT study): a multicentre, randomised, double-blind, placebo-controlled trial", www.thelancet.com/neurology, vol. 9, Sep. 2010, pp. 1-10.

\* cited by examiner

Fig. 1B

| Adrenal gland | 0.06 | Small intestine | 1.50 |
|---|---|---|---|
| Uvula | 0.07 | Tongue | 2.06 |
| Kidney | 0.07 | Retina | 2.20 |
| Optic nerve | 0.09 | Tonsil | 2.30 |
| Larynx | 0.09 | Lung | 2.54 |
| Oviduct | 0.11 | Pericardium | 2.76 |
| Bone marrow | 0.11 | Ovary | 2.79 |
| Urinary bladder | 0.11 | Esophagus | 3.66 |
| Epididymis | 0.11 | Pituitary | 4.05 |
| Uterus | 0.13 | Liver | 4.53 |
| Heart | 0.15 | Brain | 4.81 |
| Testis | 0.15 | Pancreas | 5.04 |
| Lymph node | 0.26 | Lymphocytes | 5.46 |
| Skin | 0.29 | Vagina | 6.08 |
| Stomach | 0.37 | Placenta | 7.45 |
| Colon | 0.54 | Thymus | 8.35 |
| Ureter | 0.65 | Spleen | 11.27 |
| Trachea | 0.66 | Prostate | 16.99 |
| Salivary gland | 0.96 | Muscle | 17.58 |

SEQUENCE LISTING

<160> NUMBER OF SEQ ID NOS: 35

<210> SEQ ID NO 1
<211> LENGTH: 365
<212> TYPE: PRT
<213> ORGANISM: Artificial Sequence
<220> FEATURE:
<223> OTHER INFORMATION: Polypeptide sequence of an AR variant

<400> SEQUENCE: 1

Pro Gln Lys Thr Cys Leu Ile Cys Gly Asp Glu Ala Ser Gly Cys His
1               5                   10                  15

Tyr Gly Ala Leu Thr Cys Gly Ser Cys Lys Val Phe Phe Lys Arg Ala
            20                  25                  30

Ala Glu Gly Lys Gln Lys Tyr Leu Cys Ala Ser Arg Asn Asp Cys Thr
        35                  40                  45

Ile Asp Lys Phe Arg Arg Lys Asn Cys Pro Ser Cys Arg Leu Arg Lys
 50                  55                  60

Cys Tyr Glu Ala Gly Met Thr Leu Gly Ala Arg Lys Leu Lys Lys Leu
 65                  70                  75                  80

Gly Asn Leu Lys Leu Gln Glu Glu Gly Glu Ala Ser Ser Thr Thr Ser
                 85                  90                  95

Pro Thr Glu Glu Thr Thr Gln Lys Leu Thr Val Ser His Ile Glu Gly
                100                 105                 110

Tyr Glu Cys Gln Pro Ile Phe Leu Asn Val Leu Glu Ala Ile Glu Pro
                115                 120                 125

Gly Val Val Cys Ala Gly His Asp Asn Asn Gln Pro Asp Ser Phe Ala
130                 135                 140

Ala Leu Leu Ser Ser Leu Asn Glu Leu Gly Glu Arg Gln Leu Val His
145                 150                 155                 160

Val Val Lys Trp Ala Lys Ala Leu Pro Gly Phe Arg Asn Leu His Val
                165                 170                 175

Asp Asp Gln Met Ala Val Ile Gln Tyr Ser Trp Met Gly Leu Met Val
                180                 185                 190

Phe Ala Met Gly Trp Arg Ser Phe Thr Asn Val Asn Ser Arg Met Leu
195                 200                 205

Tyr Phe Ala Pro Asp Leu Val Phe Asn Glu Tyr Arg Met His Lys Ser
210                 215                 220

Arg Met Tyr Ser Gln Cys Val Arg Met Arg His Leu Ser Gln Glu Phe
225                 230                 235                 240

Gly Trp Leu Gln Ile Thr Pro Gln Glu Phe Leu Cys Met Lys Ala Leu
                245                 250                 255

Leu Leu Phe Ser Ile Ile Pro Val Asp Gly Leu Lys Asn Gln Lys Phe
                260                 265                 270

Phe Asp Glu Leu Arg Met Asn Tyr Ile Lys Glu Leu Asp Arg Ile Ile
                275                 280                 285

Ala Cys Lys Arg Lys Asn Pro Thr Ser Cys Ser Arg Arg Phe Tyr Gln
290                 295                 300

Leu Thr Lys Leu Leu Asp Ser Val Gln Pro Ile Ala Arg Glu Leu His
305                 310                 315                 320

Gln Phe Thr Phe Asp Leu Leu Ile Lys Ser His Met Val Ser Val Asp
                325                 330                 335

Phe Pro Glu Met Met Ala Glu Ile Ile Ser Val Gln Val Pro Lys Ile
                340                 345                 350

Leu Ser Gly Lys Val Lys Pro Ile Tyr Phe His Thr Gln
                355                 360                 365

<210> SEQ ID NO 2
<211> LENGTH: 1098
<212> TYPE: DNA
<213> ORGANISM: Artificial Sequence
<220> FEATURE:
<223> OTHER INFORMATION: cDNA encoding the AR variant of SEQ ID NO: 1

<400> SEQUENCE: 2
ccccagaaga cctgcctgat ctgtggagat gaagcttctg ggtgtcacta tggagctctc      60
acatgtggaa gctgcaaggt cttcttcaaa agagccgctg aagggaaaca gaagtacctg     120
tgcgccagca gaaatgattg cactattgat aaattccgaa ggaaaaattg tccatcttgt     180
cgtcttcgga aatgttatga agcagggatg actctgggag cccggaagct gaagaaactt     240
ggtaatctga aactacagga ggaaggagag gcttccagca ccaccagccc cactgaggag     300

```
acaacccaga agctgacagt gtcacacatt gaaggctatg aatgtcagcc catctttctg    360
aatgtcctgg aagccattga gccaggtgta gtgtgtgctg acacgacaa caaccagccc    420 gactcctttg cagccttgct ctctagcctc aatgaactgg gagagagaca gcttgtacac    480
gtggtcaagt gggccaaggc cttgcctggc ttccgcaact acacgtgga cgaccagatg    540 gctgtcattc agtactcctg gatggggctc atggtgtttg ccatgggctg gcgatccttc    600
accaatgtca actccaggat gctctacttc gcccctgatc tggttttcaa tgagtaccgc    660
atgcacaagt cccggatgta cagccagtgt gtccgaatga ggcacctctc tcaagagttt    720
ggatggctcc aaatcacccc ccaggaattc ctgtgcatga agcactgct actcttcagc    780 attattccag tggatgggct gaaaaatcaa aaattctttg atgaacttcg aatgaactac    840
atcaaggaac tcgatcgtat cattgcatgc aaaagaaaaa atcccacatc ctgctcaaga    900
cgcttctacc agctcaccaa gctcctggac tccgtgcagc ctattgcgag agagctgcat    960
cagttcactt ttgacctgct aatcaagtca cacatggtga gcgtggactt tccggaaatg    1020
atggcagaga tcatctctgt gcaagtgccc aagatccttt ctgggaaagt caagcccatc    1080
tatttccaca cccagtga                                                  1098
```

<210> SEQ ID NO 3
<211> LENGTH: 388
<212> TYPE: PRT
<213> ORGANISM: Homo sapiens

<400> SEQUENCE: 3

```
Met Ile Leu Trp Leu His Ser Leu Glu Thr Ala Arg Asp His Val Leu
1               5                   10                  15

Pro Ile Asp Tyr Tyr Phe Pro Pro Gln Lys Thr Cys Leu Ile Cys Gly
                20                  25                  30

Asp Glu Ala Ser Gly Cys His Tyr Gly Ala Leu Thr Cys Gly Ser Cys
            35                  40                  45

Lys Val Phe Phe Lys Arg Ala Ala Glu Gly Lys Gln Lys Tyr Leu Cys
        50                  55                  60

Ala Ser Arg Asn Asp Cys Thr Ile Asp Lys Phe Arg Arg Lys Asn Cys
65                  70                  75                  80

Pro Ser Cys Arg Leu Arg Lys Cys Tyr Glu Ala Gly Met Thr Leu Gly
                85                  90                  95

Ala Arg Lys Leu Lys Lys Leu Gly Asn Leu Lys Leu Gln Glu Glu Gly
                100                 105                 110

Glu Ala Ser Ser Thr Thr Ser Pro Thr Glu Glu Thr Thr Gln Lys Leu
            115                 120                 125

Thr Val Ser His Ile Glu Gly Tyr Glu Cys Gln Pro Ile Phe Leu Asn
        130                 135                 140

Val Leu Glu Ala Ile Glu Pro Gly Val Val Cys Ala Gly His Asp Asn
145                 150                 155                 160

Asn Gln Pro Asp Ser Phe Ala Ala Leu Leu Ser Leu Asn Glu Leu
                165                 170                 175

Gly Glu Arg Gln Leu Val His Val Val Lys Trp Ala Lys Ala Leu Pro
            180                 185                 190

Gly Phe Arg Asn Leu His Val Asp Asp Gln Met Ala Val Ile Gln Tyr
        195                 200                 205

Ser Trp Met Gly Leu Met Val Phe Ala Met Gly Trp Arg Ser Phe Thr
    210                 215                 220
```

```
Asn Val Asn Ser Arg Met Leu Tyr Phe Ala Pro Asp Leu Val Phe Asn
225                 230                 235                 240

Glu Tyr Arg Met His Lys Ser Arg Met Tyr Ser Gln Cys Val Arg Met
            245                 250                 255

Arg His Leu Ser Gln Glu Phe Gly Trp Leu Gln Ile Thr Pro Gln Glu
            260                 265                 270

Phe Leu Cys Met Lys Ala Leu Leu Leu Phe Ser Ile Ile Pro Val Asp
            275                 280                 285

Gly Leu Lys Asn Gln Lys Phe Phe Asp Glu Leu Arg Met Asn Tyr Ile
            290                 295                 300

Lys Glu Leu Asp Arg Ile Ile Ala Cys Lys Arg Lys Asn Pro Thr Ser
305                 310                 315                 320

Cys Ser Arg Arg Phe Tyr Gln Leu Thr Lys Leu Leu Asp Ser Val Gln
            325                 330                 335

Pro Ile Ala Arg Glu Leu His Gln Phe Thr Phe Asp Leu Leu Ile Lys
            340                 345                 350

Ser His Met Val Ser Val Asp Phe Pro Glu Met Met Ala Glu Ile Ile
            355                 360                 365

Ser Val Gln Val Pro Lys Ile Leu Ser Gly Lys Val Lys Pro Ile Tyr
370                 375                 380

Phe His Thr Gln
385

<210> SEQ ID NO 4
<211> LENGTH: 1167
<212> TYPE: DNA
<213> ORGANISM: Artificial Sequence
<220> FEATURE:
<223> OTHER INFORMATION: cDNA sequence of human AR2

<400> SEQUENCE: 4
atgatactct ggcttcacag tttggagact gccagggacc atgttttgcc cattgactat      60
tactttccac cccagaagac ctgcctgatc tgtggagatg aagcttctgg gtgtcactat     120
ggagctctca catgtggaag ctgcaaggtc ttcttcaaaa gagccgctga agggaaacag     180
aagtacctgt gcgccagcag aaatgattgc actattgata aattccgaag gaaaaattgt     240
ccatcttgtc gtcttcggaa atgttatgaa gcagggatga ctctgggagc cggaagctg      300 aagaaacttg gtaatctgaa actacaggag gaaggagagg cttccagcac caccagcccc     360
actgaggaga caacccagaa gctgacagtg tcacacattg aaggctatga atgtcagccc     420
atctttctga atgtcctgga agccattgag ccaggtgtag tgtgtgctgg acacgacaac     480
aaccagcccg actcctttgc agccttgctc tctagcctca tgaactggga gagagacag      540 cttgtacacg tggtcaagtg ggccaaggcc ttgcctggct ccgcaactt acacgtggac      600 gaccagatgg ctgtcattca gtactcctgg atggggctca tggtgtttgc catgggctgg     660
cgatccttca ccaatgtcaa ctccaggatg ctctacttcg cccctgatct ggttttcaat     720
gagtaccgca tgcacaagtc ccggatgtac agccagtgtg tccgaatgag gcacctctct     780
caagagtttg gatggctcca aatcaccccc caggaattcc tgtgcatgaa agcactgcta     840
ctcttcagca ttattccagt ggatgggctg aaaaatcaaa aattctttga tgaacttcga     900
atgaactaca tcaaggaact cgatcgtatc attgcatgca aagaaaaaa tcccacatcc      960 tgctcaagac gcttctacca gctcaccaag ctcctggact ccgtgcagcc tattgcgaga    1020
gagctgcatc agttcacttt tgacctgcta atcaagtcac acatggtgag cgtggacttt    1080
```

```
ccggaaatga tggcagagat catctctgtg caagtgccca agatcctttc tgggaaagtc    1140
aagcccatct atttccacac ccagtga                                         1167

<210> SEQ ID NO 5
<211> LENGTH: 555
<212> TYPE: PRT
<213> ORGANISM: Artificial Sequence
<220> FEATURE:
<223> OTHER INFORMATION: NTD of human AR

<400> SEQUENCE: 5

Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Val Ile Gln Asn Pro Gly Pro Arg His Pro Glu Ala Ala Ser Ala Ala
        35                  40                  45

Pro Pro Gly Ala Ser Leu Leu Leu Leu Gln Gln Gln Gln Gln Gln Gln
    50                  55                  60

Gln Gln Gln Gln Gln Gln Gln Gln Gln Gln Gln Gln Gln Gln Gln Gln
65                  70                  75                  80

Glu Thr Ser Pro Arg Gln Gln Gln Gln Gln Gln Gly Glu Asp Gly Ser
                85                  90                  95

Pro Gln Ala His Arg Arg Gly Pro Thr Gly Tyr Leu Val Leu Asp Glu
            100                 105                 110

Glu Gln Gln Pro Ser Gln Pro Gln Ser Ala Leu Glu Cys His Pro Glu
        115                 120                 125

Arg Gly Cys Val Pro Glu Pro Gly Ala Ala Val Ala Ala Ser Lys Gly
    130                 135                 140

Leu Pro Gln Gln Leu Pro Ala Pro Pro Asp Glu Asp Asp Ser Ala Ala
145                 150                 155                 160

Pro Ser Thr Leu Ser Leu Leu Gly Pro Thr Phe Pro Gly Leu Ser Ser
                165                 170                 175

Cys Ser Ala Asp Leu Lys Asp Ile Leu Ser Glu Ala Ser Thr Met Gln
            180                 185                 190

Leu Leu Gln Gln Gln Gln Gln Glu Ala Val Ser Glu Gly Ser Ser Ser
        195                 200                 205

Gly Arg Ala Arg Glu Ala Ser Gly Ala Pro Thr Ser Ser Lys Asp Asn
    210                 215                 220

Tyr Leu Gly Gly Thr Ser Thr Ile Ser Asp Asn Ala Lys Glu Leu Cys
225                 230                 235                 240

Lys Ala Val Ser Val Ser Met Gly Leu Gly Val Glu Ala Leu Glu His
                245                 250                 255

Leu Ser Pro Gly Glu Gln Leu Arg Gly Asp Cys Met Tyr Ala Pro Leu
            260                 265                 270

Leu Gly Val Pro Pro Ala Val Arg Pro Thr Pro Cys Ala Pro Leu Ala
        275                 280                 285

Glu Cys Lys Gly Ser Leu Leu Asp Asp Ser Ala Gly Lys Ser Thr Glu
    290                 295                 300

Asp Thr Ala Glu Tyr Ser Pro Phe Lys Gly Gly Tyr Thr Lys Gly Leu
305                 310                 315                 320

Glu Gly Glu Ser Leu Gly Cys Ser Gly Ser Ala Ala Ala Gly Ser Ser
                325                 330                 335

Gly Thr Leu Glu Leu Pro Ser Thr Leu Ser Leu Tyr Lys Ser Gly Ala
            340                 345                 350
```

-continued

Leu Asp Glu Ala Ala Ala Tyr Gln Ser Arg Asp Tyr Tyr Asn Phe Pro
            355                 360                 365

Leu Ala Leu Ala Gly Pro Pro Pro Pro Pro Pro His Pro His
370                 375                 380

Ala Arg Ile Lys Leu Glu Asn Pro Leu Asp Tyr Gly Ser Ala Trp Ala
385                 390                 395                 400

Ala Ala Ala Gln Cys Arg Tyr Gly Asp Leu Ala Ser Leu His Gly
            405                 410                 415

Ala Gly Ala Ala Gly Pro Gly Ser Gly Ser Pro Ser Ala Ala Ala Ser
            420                 425                 430

Ser Ser Trp His Thr Leu Phe Thr Ala Glu Glu Gly Gln Leu Tyr Gly
            435                 440                 445

Pro Cys Gly Gly Gly Gly Gly Gly Gly Gly Gly Gly Gly Gly
            450                 455                 460

Gly Gly Gly Gly Gly Gly Gly Gly Glu Ala Gly Ala Val Ala Pro
465                 470                 475                 480

Tyr Gly Tyr Thr Arg Pro Pro Gln Gly Leu Ala Gly Gln Glu Ser Asp
                485                 490                 495

Phe Thr Ala Pro Asp Val Trp Tyr Pro Gly Gly Met Val Ser Arg Val
            500                 505                 510

Pro Tyr Pro Ser Pro Thr Cys Val Lys Ser Glu Met Gly Pro Trp Met
            515                 520                 525

Asp Ser Tyr Ser Gly Pro Tyr Gly Asp Met Arg Leu Glu Thr Ala Arg
530                 535                 540

Asp His Val Leu Pro Ile Asp Tyr Tyr Phe Pro
545                 550                 555

<210> SEQ ID NO 6
<211> LENGTH: 920
<212> TYPE: PRT
<213> ORGANISM: Homo sapiens

<400> SEQUENCE: 6

Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
                20                  25                  30

Val Ile Gln Asn Pro Gly Pro Arg His Pro Glu Ala Ala Ser Ala Ala
            35                  40                  45

Pro Pro Gly Ala Ser Leu Leu Leu Leu Gln Gln Gln Gln Gln Gln Gln
        50                  55                  60

Gln Gln Gln Gln Gln Gln Gln Gln Gln Gln Gln Gln Gln Gln Gln Gln
65                  70                  75                  80

Glu Thr Ser Pro Arg Gln Gln Gln Gln Gln Gly Glu Asp Gly Ser
                85                  90                  95

Pro Gln Ala His Arg Arg Gly Pro Thr Gly Tyr Leu Val Leu Asp Glu
            100                 105                 110

Glu Gln Gln Pro Ser Gln Pro Gln Ser Ala Leu Glu Cys His Pro Glu
        115                 120                 125

Arg Gly Cys Val Pro Glu Pro Gly Ala Ala Val Ala Ala Ser Lys Gly
    130                 135                 140

Leu Pro Gln Gln Leu Pro Ala Pro Pro Asp Glu Asp Asp Ser Ala Ala
145                 150                 155                 160

Pro Ser Thr Leu Ser Leu Leu Gly Pro Thr Phe Pro Gly Leu Ser Ser

```
            165                 170                 175
Cys Ser Ala Asp Leu Lys Asp Ile Leu Ser Glu Ala Ser Thr Met Gln
        180                 185                 190

Leu Leu Gln Gln Gln Gln Glu Ala Val Ser Glu Gly Ser Ser Ser
        195                 200                 205

Gly Arg Ala Arg Glu Ala Ser Gly Ala Pro Thr Ser Ser Lys Asp Asn
        210                 215                 220

Tyr Leu Gly Gly Thr Ser Thr Ile Ser Asp Asn Ala Lys Glu Leu Cys
225                 230                 235                 240

Lys Ala Val Ser Val Ser Met Gly Leu Gly Val Glu Ala Leu Glu His
                245                 250                 255

Leu Ser Pro Gly Glu Gln Leu Arg Gly Asp Cys Met Tyr Ala Pro Leu
        260                 265                 270

Leu Gly Val Pro Pro Ala Val Arg Pro Thr Pro Cys Ala Pro Leu Ala
        275                 280                 285

Glu Cys Lys Gly Ser Leu Leu Asp Asp Ser Ala Gly Lys Ser Thr Glu
        290                 295                 300

Asp Thr Ala Glu Tyr Ser Pro Phe Lys Gly Gly Tyr Thr Lys Gly Leu
305                 310                 315                 320

Glu Gly Glu Ser Leu Gly Cys Ser Gly Ser Ala Ala Gly Ser Ser
                325                 330                 335

Gly Thr Leu Glu Leu Pro Ser Thr Leu Ser Leu Tyr Lys Ser Gly Ala
        340                 345                 350

Leu Asp Glu Ala Ala Ala Tyr Gln Ser Arg Asp Tyr Tyr Asn Phe Pro
        355                 360                 365

Leu Ala Leu Ala Gly Pro Pro Pro Pro Pro Pro His Pro His
        370                 375                 380

Ala Arg Ile Lys Leu Glu Asn Pro Leu Asp Tyr Gly Ser Ala Trp Ala
385                 390                 395                 400

Ala Ala Ala Ala Gln Cys Arg Tyr Gly Asp Leu Ala Ser Leu His Gly
                405                 410                 415

Ala Gly Ala Ala Gly Pro Gly Ser Gly Ser Pro Ser Ala Ala Ala Ser
        420                 425                 430

Ser Ser Trp His Thr Leu Phe Thr Ala Glu Glu Gly Gln Leu Tyr Gly
        435                 440                 445

Pro Cys Gly Gly Gly Gly Gly Gly Gly Gly Gly Gly Gly Gly
        450                 455                 460

Gly Gly Gly Gly Gly Gly Gly Gly Glu Ala Gly Ala Val Ala Pro
465                 470                 475                 480

Tyr Gly Tyr Thr Arg Pro Pro Gln Gly Leu Ala Gly Gln Glu Ser Asp
                485                 490                 495

Phe Thr Ala Pro Asp Val Trp Tyr Pro Gly Gly Met Val Ser Arg Val
        500                 505                 510

Pro Tyr Pro Ser Pro Thr Cys Val Lys Ser Glu Met Gly Pro Trp Met
        515                 520                 525

Asp Ser Tyr Ser Gly Pro Tyr Gly Asp Met Arg Leu Glu Thr Ala Arg
        530                 535                 540

Asp His Val Leu Pro Ile Asp Tyr Tyr Phe Pro Pro Gln Lys Thr Cys
545                 550                 555                 560

Leu Ile Cys Gly Asp Glu Ala Ser Gly Cys His Tyr Gly Ala Leu Thr
                565                 570                 575

Cys Gly Ser Cys Lys Val Phe Phe Lys Arg Ala Ala Glu Gly Lys Gln
        580                 585                 590
```

Lys Tyr Leu Cys Ala Ser Arg Asn Asp Cys Thr Ile Asp Lys Phe Arg
            595                 600                 605

Arg Lys Asn Cys Pro Ser Cys Arg Leu Arg Lys Cys Tyr Glu Ala Gly
            610                 615                 620

Met Thr Leu Gly Ala Arg Lys Leu Lys Lys Leu Gly Asn Leu Lys Leu
625                 630                 635                 640

Gln Glu Glu Gly Glu Ala Ser Ser Thr Thr Ser Pro Thr Glu Glu Thr
            645                 650                 655

Thr Gln Lys Leu Thr Val Ser His Ile Glu Gly Tyr Glu Cys Gln Pro
            660                 665                 670

Ile Phe Leu Asn Val Leu Glu Ala Ile Glu Pro Gly Val Val Cys Ala
            675                 680                 685

Gly His Asp Asn Asn Gln Pro Asp Ser Phe Ala Ala Leu Leu Ser Ser
            690                 695                 700

Leu Asn Glu Leu Gly Glu Arg Gln Leu Val His Val Val Lys Trp Ala
705                 710                 715                 720

Lys Ala Leu Pro Gly Phe Arg Asn Leu His Val Asp Asp Gln Met Ala
            725                 730                 735

Val Ile Gln Tyr Ser Trp Met Gly Leu Met Val Phe Ala Met Gly Trp
            740                 745                 750

Arg Ser Phe Thr Asn Val Asn Ser Arg Met Leu Tyr Phe Ala Pro Asp
            755                 760                 765

Leu Val Phe Asn Glu Tyr Arg Met His Lys Ser Arg Met Tyr Ser Gln
            770                 775                 780

Cys Val Arg Met Arg His Leu Ser Gln Glu Phe Gly Trp Leu Gln Ile
785                 790                 795                 800

Thr Pro Gln Glu Phe Leu Cys Met Lys Ala Leu Leu Leu Phe Ser Ile
            805                 810                 815

Ile Pro Val Asp Gly Leu Lys Asn Gln Lys Phe Phe Asp Glu Leu Arg
            820                 825                 830

Met Asn Tyr Ile Lys Glu Leu Asp Arg Ile Ile Ala Cys Lys Arg Lys
            835                 840                 845

Asn Pro Thr Ser Cys Ser Arg Arg Phe Tyr Gln Leu Thr Lys Leu Leu
            850                 855                 860

Asp Ser Val Gln Pro Ile Ala Arg Glu Leu His Gln Phe Thr Phe Asp
865                 870                 875                 880

Leu Leu Ile Lys Ser His Met Val Ser Val Asp Phe Pro Glu Met Met
            885                 890                 895

Ala Glu Ile Ile Ser Val Gln Val Pro Lys Ile Leu Ser Gly Lys Val
            900                 905                 910

Lys Pro Ile Tyr Phe His Thr Gln
            915                 920

<210> SEQ ID NO 7
<211> LENGTH: 759
<212> TYPE: PRT
<213> ORGANISM: Artificial Sequence
<220> FEATURE:
<223> OTHER INFORMATION: Polypeptide sequence of an AR variant

<400> SEQUENCE: 7

Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

```
Val Ile Gln Asn Pro Gly Pro Arg His Pro Glu Ala Ala Ser Ala Ala
         35                  40                  45

Pro Pro Arg Glu Ala Ser Gly Ala Pro Thr Ser Ser Lys Asp Asn Tyr
     50                  55                  60

Leu Gly Gly Thr Ser Thr Ile Ser Asp Asn Ala Lys Glu Leu Cys Lys
65                  70                  75                  80

Ala Val Ser Val Ser Met Gly Leu Gly Val Glu Ala Leu Glu His Leu
                 85                  90                  95

Ser Pro Gly Glu Gln Leu Arg Gly Asp Cys Met Tyr Ala Pro Leu Leu
                100                 105                 110

Gly Val Pro Pro Ala Val Arg Pro Thr Pro Cys Ala Pro Leu Ala Glu
                115                 120                 125

Cys Lys Gly Ser Leu Leu Asp Asp Ser Ala Gly Lys Ser Thr Glu Asp
            130                 135                 140

Thr Ala Glu Tyr Ser Pro Phe Lys Gly Gly Tyr Thr Lys Gly Leu Glu
145                 150                 155                 160

Gly Glu Ser Leu Gly Cys Ser Gly Ser Ala Ala Gly Ser Ser Gly
                165                 170                 175

Thr Leu Glu Leu Pro Ser Thr Leu Ser Leu Tyr Lys Ser Gly Ala Leu
                180                 185                 190

Asp Glu Ala Ala Ala Tyr Gln Ser Arg Asp Tyr Tyr Asn Phe Pro Leu
                195                 200                 205

Ala Leu Ala Gly Pro Pro Pro Pro Pro Pro Pro His Pro His Ala
            210                 215                 220

Arg Ile Lys Leu Glu Asn Pro Leu Asp Tyr Gly Ser Ala Trp Ala Ala
225                 230                 235                 240

Ala Ala Ala Gln Cys Arg Tyr Gly Asp Leu Ala Ser Leu His Gly Ala
                245                 250                 255

Gly Ala Ala Gly Pro Gly Ser Gly Ser Pro Ser Ala Ala Ala Ser Ser
            260                 265                 270

Ser Trp His Thr Leu Phe Thr Ala Glu Glu Gly Gln Leu Tyr Gly Pro
        275                 280                 285

Cys Gly Gly Gly Gly Gly Gly Gly Gly Gly Gly Gly Gly
        290                 295                 300

Gly Gly Gly Gly Gly Gly Gly Glu Ala Gly Ala Val Ala Pro Tyr
305                 310                 315                 320

Gly Tyr Thr Arg Pro Pro Gln Gly Leu Ala Gly Gln Glu Ser Asp Phe
                325                 330                 335

Thr Ala Pro Asp Val Trp Tyr Pro Gly Gly Met Val Ser Arg Val Pro
                340                 345                 350

Tyr Pro Ser Pro Thr Cys Val Lys Ser Glu Met Gly Pro Trp Met Asp
            355                 360                 365

Ser Tyr Ser Gly Pro Tyr Gly Asp Met Arg Leu Glu Thr Ala Arg Asp
370                 375                 380

His Val Leu Pro Ile Asp Tyr Tyr Phe Pro Pro Gln Lys Thr Cys Leu
385                 390                 395                 400

Ile Cys Gly Asp Glu Ala Ser Gly Cys His Tyr Gly Ala Leu Thr Cys
                405                 410                 415

Gly Ser Cys Lys Val Phe Phe Lys Arg Ala Ala Glu Gly Lys Gln Lys
            420                 425                 430

Tyr Leu Cys Ala Ser Arg Asn Asp Cys Thr Ile Asp Lys Phe Arg Arg
                435                 440                 445
```

```
Lys Asn Cys Pro Ser Cys Arg Leu Arg Lys Cys Tyr Glu Ala Gly Met
    450                 455                 460

Thr Leu Gly Ala Arg Lys Leu Lys Lys Leu Gly Asn Leu Lys Leu Gln
465                 470                 475                 480

Glu Glu Gly Glu Ala Ser Ser Thr Thr Ser Pro Thr Glu Glu Thr Thr
                485                 490                 495

Gln Lys Leu Thr Val Ser His Ile Glu Gly Tyr Glu Cys Gln Pro Ile
                500                 505                 510

Phe Leu Asn Val Leu Glu Ala Ile Glu Pro Gly Val Val Cys Ala Gly
                515                 520                 525

His Asp Asn Asn Gln Pro Asp Ser Phe Ala Ala Leu Leu Ser Ser Leu
    530                 535                 540

Asn Glu Leu Gly Glu Arg Gln Leu Val His Val Val Lys Trp Ala Lys
545                 550                 555                 560

Ala Leu Pro Gly Phe Arg Asn Leu His Val Asp Asp Gln Met Ala Val
                565                 570                 575

Ile Gln Tyr Ser Trp Met Gly Leu Met Val Phe Ala Met Gly Trp Arg
                580                 585                 590

Ser Phe Thr Asn Val Asn Ser Arg Met Leu Tyr Phe Ala Pro Asp Leu
    595                 600                 605

Val Phe Asn Glu Tyr Arg Met His Lys Ser Arg Met Tyr Ser Gln Cys
610                 615                 620

Val Arg Met Arg His Leu Ser Gln Glu Phe Gly Trp Leu Gln Ile Thr
625                 630                 635                 640

Pro Gln Glu Phe Leu Cys Met Lys Ala Leu Leu Leu Phe Ser Ile Ile
                645                 650                 655

Pro Val Asp Gly Leu Lys Asn Gln Lys Phe Phe Asp Glu Leu Arg Met
                660                 665                 670

Asn Tyr Ile Lys Glu Leu Asp Arg Ile Ile Ala Cys Lys Arg Lys Asn
    675                 680                 685

Pro Thr Ser Cys Ser Arg Arg Phe Tyr Gln Leu Thr Lys Leu Leu Asp
690                 695                 700

Ser Val Gln Pro Ile Ala Arg Glu Leu His Gln Phe Thr Phe Asp Leu
705                 710                 715                 720

Leu Ile Lys Ser His Met Val Ser Val Asp Phe Pro Glu Met Met Ala
                725                 730                 735

Glu Ile Ile Ser Val Gln Val Pro Lys Ile Leu Ser Gly Lys Val Lys
                740                 745                 750

Pro Ile Tyr Phe His Thr Gln
        755

<210> SEQ ID NO 8
<211> LENGTH: 709
<212> TYPE: PRT
<213> ORGANISM: Artificial Sequence
<220> FEATURE:
<223> OTHER INFORMATION: Polypeptide sequence of an AR variant

<400> SEQUENCE: 8

Arg Glu Ala Ser Gly Ala Pro Thr Ser Ser Lys Asp Asn Tyr Leu Gly
1               5                   10                  15

Gly Thr Ser Thr Ile Ser Asp Asn Ala Lys Glu Leu Cys Lys Ala Val
                20                  25                  30

Ser Val Ser Met Gly Leu Gly Val Glu Ala Leu Glu His Leu Ser Pro
            35                  40                  45
```

```
Gly Glu Gln Leu Arg Gly Asp Cys Met Tyr Ala Pro Leu Leu Gly Val
 50              55                  60
Pro Pro Ala Val Arg Pro Thr Pro Cys Ala Pro Leu Ala Glu Cys Lys
 65              70                  75                  80
Gly Ser Leu Leu Asp Asp Ser Ala Gly Lys Ser Thr Glu Asp Thr Ala
                 85                  90                  95
Glu Tyr Ser Pro Phe Lys Gly Tyr Thr Lys Gly Leu Glu Gly Glu
                100             105                 110
Ser Leu Gly Cys Ser Gly Ser Ala Ala Gly Ser Ser Gly Thr Leu
            115             120             125
Glu Leu Pro Ser Thr Leu Ser Leu Tyr Lys Ser Gly Ala Leu Asp Glu
130                 135                 140
Ala Ala Ala Tyr Gln Ser Arg Asp Tyr Tyr Asn Phe Pro Leu Ala Leu
145                 150                 155                 160
Ala Gly Pro Pro Pro Pro Pro Pro Pro His Pro His Ala Arg Ile
                165             170             175
Lys Leu Glu Asn Pro Leu Asp Tyr Gly Ser Ala Trp Ala Ala Ala
                180             185             190
Ala Gln Cys Arg Tyr Gly Asp Leu Ala Ser Leu His Gly Ala Gly Ala
    195             200             205
Ala Gly Pro Gly Ser Gly Ser Pro Ser Ala Ala Ser Ser Ser Trp
210             215             220
His Thr Leu Phe Thr Ala Glu Glu Gly Gln Leu Tyr Gly Pro Cys Gly
225             230             235             240
Gly Gly Gly Gly Gly Gly Gly Gly Gly Gly Gly Gly Gly Gly Gly
                245             250             255
Gly Gly Gly Gly Gly Gly Glu Ala Gly Ala Val Ala Pro Tyr Gly Tyr
            260             265             270
Thr Arg Pro Pro Gln Gly Leu Ala Gly Gln Glu Ser Asp Phe Thr Ala
    275             280             285
Pro Asp Val Trp Tyr Pro Gly Gly Met Val Ser Arg Val Pro Tyr Pro
290             295             300
Ser Pro Thr Cys Val Lys Ser Glu Met Gly Pro Trp Met Asp Ser Tyr
305             310             315             320
Ser Gly Pro Tyr Gly Asp Met Arg Leu Glu Thr Ala Arg Asp His Val
                325             330             335
Leu Pro Ile Asp Tyr Tyr Phe Pro Pro Gln Lys Thr Cys Leu Ile Cys
            340             345             350
Gly Asp Glu Ala Ser Gly Cys His Tyr Gly Ala Leu Thr Cys Gly Ser
    355             360             365
Cys Lys Val Phe Phe Lys Arg Ala Ala Glu Gly Lys Gln Lys Tyr Leu
370             375             380
Cys Ala Ser Arg Asn Asp Cys Thr Ile Asp Lys Phe Arg Arg Lys Asn
385             390             395             400
Cys Pro Ser Cys Arg Leu Arg Lys Cys Tyr Glu Ala Gly Met Thr Leu
                405             410             415
Gly Ala Arg Lys Leu Lys Lys Leu Gly Asn Leu Lys Leu Gln Glu Glu
                420             425             430
Gly Glu Ala Ser Ser Thr Thr Ser Pro Thr Glu Glu Thr Gln Lys
            435             440             445
Leu Thr Val Ser His Ile Glu Gly Tyr Glu Cys Gln Pro Ile Phe Leu
450                 455             460
Asn Val Leu Glu Ala Ile Glu Pro Gly Val Val Cys Ala Gly His Asp
```

-continued

```
             465                 470                 475                 480

Asn Asn Gln Pro Asp Ser Phe Ala Ala Leu Leu Ser Ser Leu Asn Glu
                    485                 490                 495

Leu Gly Glu Arg Gln Leu Val His Val Val Lys Trp Ala Lys Ala Leu
                    500                 505                 510

Pro Gly Phe Arg Asn Leu His Val Asp Asp Gln Met Ala Val Ile Gln
                    515                 520                 525

Tyr Ser Trp Met Gly Leu Met Val Phe Ala Met Gly Trp Arg Ser Phe
                    530                 535                 540

Thr Asn Val Asn Ser Arg Met Leu Tyr Phe Ala Pro Asp Leu Val Phe
    545                 550                 555                 560

Asn Glu Tyr Arg Met His Lys Ser Arg Met Tyr Ser Gln Cys Val Arg
                    565                 570                 575

Met Arg His Leu Ser Gln Glu Phe Gly Trp Leu Gln Ile Thr Pro Gln
                    580                 585                 590

Glu Phe Leu Cys Met Lys Ala Leu Leu Leu Phe Ser Ile Ile Pro Val
                    595                 600                 605

Asp Gly Leu Lys Asn Gln Lys Phe Phe Asp Glu Leu Arg Met Asn Tyr
                    610                 615                 620

Ile Lys Glu Leu Asp Arg Ile Ile Ala Cys Lys Arg Lys Asn Pro Thr
    625                 630                 635                 640

Ser Cys Ser Arg Arg Phe Tyr Gln Leu Thr Lys Leu Leu Asp Ser Val
                    645                 650                 655

Gln Pro Ile Ala Arg Glu Leu His Gln Phe Thr Phe Asp Leu Leu Ile
                    660                 665                 670

Lys Ser His Met Val Ser Val Asp Phe Pro Glu Met Met Ala Glu Ile
                    675                 680                 685

Ile Ser Val Gln Val Pro Lys Ile Leu Ser Gly Lys Val Lys Pro Ile
                    690                 695                 700

Tyr Phe His Thr Gln
    705

<210> SEQ ID NO 9
<211> LENGTH: 20
<212> TYPE: RNA
<213> ORGANISM: Artificial Sequence
<220> FEATURE:
<223> OTHER INFORMATION: siRNA SBMA-1 antisense strand
<220> FEATURE:
<221> NAME/KEY: misc_feature
<222> LOCATION: (1)..(1)
<223> OTHER INFORMATION: 5' phosphate
<220> FEATURE:
<221> NAME/KEY: modified_base
<222> LOCATION: (1)..(1)
<223> OTHER INFORMATION: 2'OMe
<220> FEATURE:
<221> NAME/KEY: modified_base
<222> LOCATION: (2)..(2)
<223> OTHER INFORMATION: 2'F
<220> FEATURE:
<221> NAME/KEY: modified_base
<222> LOCATION: (3)..(3)
<223> OTHER INFORMATION: 2'OMe
<220> FEATURE:
<221> NAME/KEY: modified_base
<222> LOCATION: (4)..(4)
<223> OTHER INFORMATION: 2'F
<220> FEATURE:
<221> NAME/KEY: modified_base
<222> LOCATION: (5)..(5)
<223> OTHER INFORMATION: 2'OMe
<220> FEATURE:
```

```
<221> NAME/KEY: modified_base
<222> LOCATION: (6)..(6)
<223> OTHER INFORMATION: 2'F
<220> FEATURE:
<221> NAME/KEY: modified_base
<222> LOCATION: (7)..(7)
<223> OTHER INFORMATION: 2'OMe
<220> FEATURE:
<221> NAME/KEY: modified_base
<222> LOCATION: (8)..(8)
<223> OTHER INFORMATION: 2'F
<220> FEATURE:
<221> NAME/KEY: modified_base
<222> LOCATION: (9)..(9)
<223> OTHER INFORMATION: 2'OMe
<220> FEATURE:
<221> NAME/KEY: modified_base
<222> LOCATION: (10)..(10)
<223> OTHER INFORMATION: 2'F
<220> FEATURE:
<221> NAME/KEY: modified_base
<222> LOCATION: (11)..(11)
<223> OTHER INFORMATION: 2'OMe
<220> FEATURE:
<221> NAME/KEY: modified_base
<222> LOCATION: (12)..(12)
<223> OTHER INFORMATION: 2'F
<220> FEATURE:
<221> NAME/KEY: modified_base
<222> LOCATION: (13)..(13)
<223> OTHER INFORMATION: 2'OMe
<220> FEATURE:
<221> NAME/KEY: modified_base
<222> LOCATION: (14)..(14)
<223> OTHER INFORMATION: 2'F
<220> FEATURE:
<221> NAME/KEY: modified_base
<222> LOCATION: (15)..(15)
<223> OTHER INFORMATION: 2'OMe
<220> FEATURE:
<221> NAME/KEY: modified_base
<222> LOCATION: (16)..(16)
<223> OTHER INFORMATION: 2'F
<220> FEATURE:
<221> NAME/KEY: modified_base
<222> LOCATION: (17)..(17)
<223> OTHER INFORMATION: 2'OMe
<220> FEATURE:
<221> NAME/KEY: modified_base
<222> LOCATION: (18)..(18)
<223> OTHER INFORMATION: 2'F
<220> FEATURE:
<221> NAME/KEY: modified_base
<222> LOCATION: (19)..(19)
<223> OTHER INFORMATION: 2'OMe
<220> FEATURE:
<221> NAME/KEY: modified_base
<222> LOCATION: (20)..(20)
<223> OTHER INFORMATION: 2'F

<400> SEQUENCE: 9
ccaaacugug aagccagagu                                                   20

<210> SEQ ID NO 10
<211> LENGTH: 15
<212> TYPE: RNA
<213> ORGANISM: Artificial Sequence
<220> FEATURE:
<223> OTHER INFORMATION: siRNA SBMA-1 sense strand
<220> FEATURE:
<221> NAME/KEY: modified_base
<222> LOCATION: (1)..(1)
<223> OTHER INFORMATION: 2'F
<220> FEATURE:
<221> NAME/KEY: modified_base
<222> LOCATION: (2)..(2)
<223> OTHER INFORMATION: 2'OMe
```

```
<220> FEATURE:
<221> NAME/KEY: modified_base
<222> LOCATION: (3)..(3)
<223> OTHER INFORMATION: 2'F
<220> FEATURE:
<221> NAME/KEY: modified_base
<222> LOCATION: (4)..(4)
<223> OTHER INFORMATION: 2'OMe
<220> FEATURE:
<221> NAME/KEY: modified_base
<222> LOCATION: (5)..(5)
<223> OTHER INFORMATION: 2'F
<220> FEATURE:
<221> NAME/KEY: modified_base
<222> LOCATION: (6)..(6)
<223> OTHER INFORMATION: 2'OMe
<220> FEATURE:
<221> NAME/KEY: modified_base
<222> LOCATION: (7)..(7)
<223> OTHER INFORMATION: 2'F
<220> FEATURE:
<221> NAME/KEY: modified_base
<222> LOCATION: (8)..(8)
<223> OTHER INFORMATION: 2'OMe
<220> FEATURE:
<221> NAME/KEY: modified_base
<222> LOCATION: (9)..(9)
<223> OTHER INFORMATION: 2'F
<220> FEATURE:
<221> NAME/KEY: modified_base
<222> LOCATION: (10)..(10)
<223> OTHER INFORMATION: 2'OMe
<220> FEATURE:
<221> NAME/KEY: modified_base
<222> LOCATION: (11)..(11)
<223> OTHER INFORMATION: 2'F
<220> FEATURE:
<221> NAME/KEY: modified_base
<222> LOCATION: (12)..(12)
<223> OTHER INFORMATION: 2'OMe
<220> FEATURE:
<221> NAME/KEY: modified_base
<222> LOCATION: (13)..(13)
<223> OTHER INFORMATION: 2'F
<220> FEATURE:
<221> NAME/KEY: modified_base
<222> LOCATION: (14)..(14)
<223> OTHER INFORMATION: 2'OMe
<220> FEATURE:
<221> NAME/KEY: misc_feature
<222> LOCATION: (15)..(15)
<223> OTHER INFORMATION: 3' chol
<220> FEATURE:
<221> NAME/KEY: modified_base
<222> LOCATION: (15)..(15)
<223> OTHER INFORMATION: 2'F

<400> SEQUENCE: 10
ggcuucacag uuugg                                             15

<210> SEQ ID NO 11
<211> LENGTH: 20
<212> TYPE: RNA
<213> ORGANISM: Artificial Sequence
<220> FEATURE:
<223> OTHER INFORMATION: siRNA SBMA-2 antisense strand
<220> FEATURE:
<221> NAME/KEY: misc_feature
<222> LOCATION: (1)..(1)
<223> OTHER INFORMATION: 5' phosphate
<220> FEATURE:
<221> NAME/KEY: modified_base
<222> LOCATION: (1)..(1)
<223> OTHER INFORMATION: 2'OMe
<220> FEATURE:
<221> NAME/KEY: modified_base
<222> LOCATION: (2)..(2)
```

```
<223> OTHER INFORMATION: 2'F
<220> FEATURE:
<221> NAME/KEY: modified_base
<222> LOCATION: (3)..(3)
<223> OTHER INFORMATION: 2'OMe
<220> FEATURE:
<221> NAME/KEY: modified_base
<222> LOCATION: (4)..(4)
<223> OTHER INFORMATION: 2'F
<220> FEATURE:
<221> NAME/KEY: modified_base
<222> LOCATION: (5)..(5)
<223> OTHER INFORMATION: 2'OMe
<220> FEATURE:
<221> NAME/KEY: modified_base
<222> LOCATION: (6)..(6)
<223> OTHER INFORMATION: 2'F
<220> FEATURE:
<221> NAME/KEY: modified_base
<222> LOCATION: (7)..(7)
<223> OTHER INFORMATION: 2'OMe
<220> FEATURE:
<221> NAME/KEY: modified_base
<222> LOCATION: (8)..(8)
<223> OTHER INFORMATION: 2'F
<220> FEATURE:
<221> NAME/KEY: modified_base
<222> LOCATION: (9)..(9)
<223> OTHER INFORMATION: 2'OMe
<220> FEATURE:
<221> NAME/KEY: modified_base
<222> LOCATION: (10)..(10)
<223> OTHER INFORMATION: 2'F
<220> FEATURE:
<221> NAME/KEY: modified_base
<222> LOCATION: (11)..(11)
<223> OTHER INFORMATION: 2'OMe
<220> FEATURE:
<221> NAME/KEY: modified_base
<222> LOCATION: (12)..(12)
<223> OTHER INFORMATION: 2'F
<220> FEATURE:
<221> NAME/KEY: modified_base
<222> LOCATION: (13)..(13)
<223> OTHER INFORMATION: 2'OMe
<220> FEATURE:
<221> NAME/KEY: modified_base
<222> LOCATION: (14)..(14)
<223> OTHER INFORMATION: 2'F
<220> FEATURE:
<221> NAME/KEY: modified_base
<222> LOCATION: (15)..(15)
<223> OTHER INFORMATION: 2'OMe
<220> FEATURE:
<221> NAME/KEY: modified_base
<222> LOCATION: (16)..(16)
<223> OTHER INFORMATION: 2'F
<220> FEATURE:
<221> NAME/KEY: modified_base
<222> LOCATION: (17)..(17)
<223> OTHER INFORMATION: 2'OMe
<220> FEATURE:
<221> NAME/KEY: modified_base
<222> LOCATION: (18)..(18)
<223> OTHER INFORMATION: 2'F
<220> FEATURE:
<221> NAME/KEY: modified_base
<222> LOCATION: (19)..(19)
<223> OTHER INFORMATION: 2'OMe
<220> FEATURE:
<221> NAME/KEY: modified_base
<222> LOCATION: (20)..(20)
<223> OTHER INFORMATION: 2'F

<400> SEQUENCE: 11
uccaaacugu gaagccagag                                               20
```

```
<210> SEQ ID NO 12
<211> LENGTH: 15
<212> TYPE: RNA
<213> ORGANISM: Artificial Sequence
<220> FEATURE:
<223> OTHER INFORMATION: siRNA SBMA-2 sense strand
<220> FEATURE:
<221> NAME/KEY: modified_base
<222> LOCATION: (1)..(1)
<223> OTHER INFORMATION: 2'F
<220> FEATURE:
<221> NAME/KEY: modified_base
<222> LOCATION: (2)..(2)
<223> OTHER INFORMATION: 2'OMe
<220> FEATURE:
<221> NAME/KEY: modified_base
<222> LOCATION: (3)..(3)
<223> OTHER INFORMATION: 2'F
<220> FEATURE:
<221> NAME/KEY: modified_base
<222> LOCATION: (4)..(4)
<223> OTHER INFORMATION: 2'OMe
<220> FEATURE:
<221> NAME/KEY: modified_base
<222> LOCATION: (5)..(5)
<223> OTHER INFORMATION: 2'F
<220> FEATURE:
<221> NAME/KEY: modified_base
<222> LOCATION: (6)..(6)
<223> OTHER INFORMATION: 2'OMe
<220> FEATURE:
<221> NAME/KEY: modified_base
<222> LOCATION: (7)..(7)
<223> OTHER INFORMATION: 2'F
<220> FEATURE:
<221> NAME/KEY: modified_base
<222> LOCATION: (8)..(8)
<223> OTHER INFORMATION: 2'OMe
<220> FEATURE:
<221> NAME/KEY: modified_base
<222> LOCATION: (9)..(9)
<223> OTHER INFORMATION: 2'F
<220> FEATURE:
<221> NAME/KEY: modified_base
<222> LOCATION: (10)..(10)
<223> OTHER INFORMATION: 2'OMe
<220> FEATURE:
<221> NAME/KEY: modified_base
<222> LOCATION: (11)..(11)
<223> OTHER INFORMATION: 2'F
<220> FEATURE:
<221> NAME/KEY: modified_base
<222> LOCATION: (12)..(12)
<223> OTHER INFORMATION: 2'OMe
<220> FEATURE:
<221> NAME/KEY: modified_base
<222> LOCATION: (13)..(13)
<223> OTHER INFORMATION: 2'F
<220> FEATURE:
<221> NAME/KEY: modified_base
<222> LOCATION: (14)..(14)
<223> OTHER INFORMATION: 2'OMe
<220> FEATURE:
<221> NAME/KEY: misc_feature
<222> LOCATION: (15)..(15)
<223> OTHER INFORMATION: 3' chol
<220> FEATURE:
<221> NAME/KEY: modified_base
<222> LOCATION: (15)..(15)
<223> OTHER INFORMATION: 2'F

<400> SEQUENCE: 12
gcuucacagu uugga                                                   15

<210> SEQ ID NO 13
<211> LENGTH: 20
<212> TYPE: RNA
```

```
<213> ORGANISM: Artificial Sequence
<220> FEATURE:
<223> OTHER INFORMATION: siRNA SBMA-3 antisense strand
<220> FEATURE:
<221> NAME/KEY: misc_feature
<222> LOCATION: (1)..(1)
<223> OTHER INFORMATION: 5' phosphate
<220> FEATURE:
<221> NAME/KEY: modified_base
<222> LOCATION: (1)..(1)
<223> OTHER INFORMATION: 2'OMe
<220> FEATURE:
<221> NAME/KEY: modified_base
<222> LOCATION: (2)..(2)
<223> OTHER INFORMATION: 2'F
<220> FEATURE:
<221> NAME/KEY: modified_base
<222> LOCATION: (3)..(3)
<223> OTHER INFORMATION: 2'OMe
<220> FEATURE:
<221> NAME/KEY: modified_base
<222> LOCATION: (4)..(4)
<223> OTHER INFORMATION: 2'F
<220> FEATURE:
<221> NAME/KEY: modified_base
<222> LOCATION: (5)..(5)
<223> OTHER INFORMATION: 2'OMe
<220> FEATURE:
<221> NAME/KEY: modified_base
<222> LOCATION: (6)..(6)
<223> OTHER INFORMATION: 2'F
<220> FEATURE:
<221> NAME/KEY: modified_base
<222> LOCATION: (7)..(7)
<223> OTHER INFORMATION: 2'OMe
<220> FEATURE:
<221> NAME/KEY: modified_base
<222> LOCATION: (8)..(8)
<223> OTHER INFORMATION: 2'F
<220> FEATURE:
<221> NAME/KEY: modified_base
<222> LOCATION: (9)..(9)
<223> OTHER INFORMATION: 2'OMe
<220> FEATURE:
<221> NAME/KEY: modified_base
<222> LOCATION: (10)..(10)
<223> OTHER INFORMATION: 2'F
<220> FEATURE:
<221> NAME/KEY: modified_base
<222> LOCATION: (11)..(11)
<223> OTHER INFORMATION: 2'OMe
<220> FEATURE:
<221> NAME/KEY: modified_base
<222> LOCATION: (12)..(12)
<223> OTHER INFORMATION: 2'F
<220> FEATURE:
<221> NAME/KEY: modified_base
<222> LOCATION: (13)..(13)
<223> OTHER INFORMATION: 2'OMe
<220> FEATURE:
<221> NAME/KEY: modified_base
<222> LOCATION: (14)..(14)
<223> OTHER INFORMATION: 2'F
<220> FEATURE:
<221> NAME/KEY: modified_base
<222> LOCATION: (15)..(15)
<223> OTHER INFORMATION: 2'OMe
<220> FEATURE:
<221> NAME/KEY: modified_base
<222> LOCATION: (16)..(16)
<223> OTHER INFORMATION: 2'F
<220> FEATURE:
<221> NAME/KEY: modified_base
<222> LOCATION: (17)..(17)
<223> OTHER INFORMATION: 2'OMe
<220> FEATURE:
<221> NAME/KEY: modified_base
<222> LOCATION: (18)..(18)
<223> OTHER INFORMATION: 2'F
```

```
<220> FEATURE:
<221> NAME/KEY: modified_base
<222> LOCATION: (19)..(19)
<223> OTHER INFORMATION: 2'OMe
<220> FEATURE:
<221> NAME/KEY: modified_base
<222> LOCATION: (20)..(20)
<223> OTHER INFORMATION: 2'F

<400> SEQUENCE: 13
cuccaaacug ugaagccaga                                                     20

<210> SEQ ID NO 14
<211> LENGTH: 15
<212> TYPE: RNA
<213> ORGANISM: Artificial Sequence
<220> FEATURE:
<223> OTHER INFORMATION: siRNA SBMA-3 sense strand
<220> FEATURE:
<221> NAME/KEY: modified_base
<222> LOCATION: (1)..(1)
<223> OTHER INFORMATION: 2'F
<220> FEATURE:
<221> NAME/KEY: modified_base
<222> LOCATION: (2)..(2)
<223> OTHER INFORMATION: 2'OMe
<220> FEATURE:
<221> NAME/KEY: modified_base
<222> LOCATION: (3)..(3)
<223> OTHER INFORMATION: 2'F
<220> FEATURE:
<221> NAME/KEY: modified_base
<222> LOCATION: (4)..(4)
<223> OTHER INFORMATION: 2'OMe
<220> FEATURE:
<221> NAME/KEY: modified_base
<222> LOCATION: (5)..(5)
<223> OTHER INFORMATION: 2'F
<220> FEATURE:
<221> NAME/KEY: modified_base
<222> LOCATION: (6)..(6)
<223> OTHER INFORMATION: 2'OMe
<220> FEATURE:
<221> NAME/KEY: modified_base
<222> LOCATION: (7)..(7)
<223> OTHER INFORMATION: 2'F
<220> FEATURE:
<221> NAME/KEY: modified_base
<222> LOCATION: (8)..(8)
<223> OTHER INFORMATION: 2'OMe
<220> FEATURE:
<221> NAME/KEY: modified_base
<222> LOCATION: (9)..(9)
<223> OTHER INFORMATION: 2'F
<220> FEATURE:
<221> NAME/KEY: modified_base
<222> LOCATION: (10)..(10)
<223> OTHER INFORMATION: 2'OMe
<220> FEATURE:
<221> NAME/KEY: modified_base
<222> LOCATION: (11)..(11)
<223> OTHER INFORMATION: 2'F
<220> FEATURE:
<221> NAME/KEY: modified_base
<222> LOCATION: (12)..(12)
<223> OTHER INFORMATION: 2'OMe
<220> FEATURE:
<221> NAME/KEY: modified_base
<222> LOCATION: (13)..(13)
<223> OTHER INFORMATION: 2'F
<220> FEATURE:
<221> NAME/KEY: modified_base
<222> LOCATION: (14)..(14)
<223> OTHER INFORMATION: 2'OMe
<220> FEATURE:
<221> NAME/KEY: misc_feature
<222> LOCATION: (15)..(15)
```

```
<223> OTHER INFORMATION: 3' chol
<220> FEATURE:
<221> NAME/KEY: modified_base
<222> LOCATION: (15)..(15)
<223> OTHER INFORMATION: 2'F

<400> SEQUENCE: 14
cuucacaguu uggag                                                        15

<210> SEQ ID NO 15
<211> LENGTH: 20
<212> TYPE: RNA
<213> ORGANISM: Artificial Sequence
<220> FEATURE:
<223> OTHER INFORMATION: siRNA SBMA-4 antisense strand
<220> FEATURE:
<221> NAME/KEY: misc_feature
<222> LOCATION: (1)..(1)
<223> OTHER INFORMATION: 5' phosphate
<220> FEATURE:
<221> NAME/KEY: modified_base
<222> LOCATION: (1)..(1)
<223> OTHER INFORMATION: 2'OMe
<220> FEATURE:
<221> NAME/KEY: modified_base
<222> LOCATION: (2)..(2)
<223> OTHER INFORMATION: 2'F
<220> FEATURE:
<221> NAME/KEY: modified_base
<222> LOCATION: (3)..(3)
<223> OTHER INFORMATION: 2'OMe
<220> FEATURE:
<221> NAME/KEY: modified_base
<222> LOCATION: (4)..(4)
<223> OTHER INFORMATION: 2'F
<220> FEATURE:
<221> NAME/KEY: modified_base
<222> LOCATION: (5)..(5)
<223> OTHER INFORMATION: 2'OMe
<220> FEATURE:
<221> NAME/KEY: modified_base
<222> LOCATION: (6)..(6)
<223> OTHER INFORMATION: 2'F
<220> FEATURE:
<221> NAME/KEY: modified_base
<222> LOCATION: (7)..(7)
<223> OTHER INFORMATION: 2'OMe
<220> FEATURE:
<221> NAME/KEY: modified_base
<222> LOCATION: (8)..(8)
<223> OTHER INFORMATION: 2'F
<220> FEATURE:
<221> NAME/KEY: modified_base
<222> LOCATION: (9)..(9)
<223> OTHER INFORMATION: 2'OMe
<220> FEATURE:
<221> NAME/KEY: modified_base
<222> LOCATION: (10)..(10)
<223> OTHER INFORMATION: 2'F
<220> FEATURE:
<221> NAME/KEY: modified_base
<222> LOCATION: (11)..(11)
<223> OTHER INFORMATION: 2'OMe
<220> FEATURE:
<221> NAME/KEY: modified_base
<222> LOCATION: (12)..(12)
<223> OTHER INFORMATION: 2'F
<220> FEATURE:
<221> NAME/KEY: modified_base
<222> LOCATION: (13)..(13)
<223> OTHER INFORMATION: 2'OMe
<220> FEATURE:
<221> NAME/KEY: modified_base
<222> LOCATION: (14)..(14)
<223> OTHER INFORMATION: 2'F
<220> FEATURE:
<221> NAME/KEY: modified_base
```

```
<222> LOCATION: (15)..(15)
<223> OTHER INFORMATION: 2'OMe
<220> FEATURE:
<221> NAME/KEY: modified_base
<222> LOCATION: (16)..(16)
<223> OTHER INFORMATION: 2'F
<220> FEATURE:
<221> NAME/KEY: modified_base
<222> LOCATION: (17)..(17)
<223> OTHER INFORMATION: 2'OMe
<220> FEATURE:
<221> NAME/KEY: modified_base
<222> LOCATION: (18)..(18)
<223> OTHER INFORMATION: 2'F
<220> FEATURE:
<221> NAME/KEY: modified_base
<222> LOCATION: (19)..(19)
<223> OTHER INFORMATION: 2'OMe
<220> FEATURE:
<221> NAME/KEY: modified_base
<222> LOCATION: (20)..(20)
<223> OTHER INFORMATION: 2'F

<400> SEQUENCE: 15
ucuccaaacu gugaagccag                                              20

<210> SEQ ID NO 16
<211> LENGTH: 15
<212> TYPE: RNA
<213> ORGANISM: Artificial Sequence
<220> FEATURE:
<223> OTHER INFORMATION: siRNA SBMA-4 sense strand
<220> FEATURE:
<221> NAME/KEY: modified_base
<222> LOCATION: (1)..(1)
<223> OTHER INFORMATION: 2'F
<220> FEATURE:
<221> NAME/KEY: modified_base
<222> LOCATION: (2)..(2)
<223> OTHER INFORMATION: 2'OMe
<220> FEATURE:
<221> NAME/KEY: modified_base
<222> LOCATION: (3)..(3)
<223> OTHER INFORMATION: 2'F
<220> FEATURE:
<221> NAME/KEY: modified_base
<222> LOCATION: (4)..(4)
<223> OTHER INFORMATION: 2'OMe
<220> FEATURE:
<221> NAME/KEY: modified_base
<222> LOCATION: (5)..(5)
<223> OTHER INFORMATION: 2'F
<220> FEATURE:
<221> NAME/KEY: modified_base
<222> LOCATION: (6)..(6)
<223> OTHER INFORMATION: 2'OMe
<220> FEATURE:
<221> NAME/KEY: modified_base
<222> LOCATION: (7)..(7)
<223> OTHER INFORMATION: 2'F
<220> FEATURE:
<221> NAME/KEY: modified_base
<222> LOCATION: (8)..(8)
<223> OTHER INFORMATION: 2'OMe
<220> FEATURE:
<221> NAME/KEY: modified_base
<222> LOCATION: (9)..(9)
<223> OTHER INFORMATION: 2'F
<220> FEATURE:
<221> NAME/KEY: modified_base
<222> LOCATION: (10)..(10)
<223> OTHER INFORMATION: 2'OMe
<220> FEATURE:
<221> NAME/KEY: modified_base
<222> LOCATION: (11)..(11)
<223> OTHER INFORMATION: 2'F
<220> FEATURE:
```

<221> NAME/KEY: modified_base
<222> LOCATION: (12)..(12)
<223> OTHER INFORMATION: 2'OMe
<220> FEATURE:
<221> NAME/KEY: modified_base
<222> LOCATION: (13)..(13)
<223> OTHER INFORMATION: 2'F
<220> FEATURE:
<221> NAME/KEY: modified_base
<222> LOCATION: (14)..(14)
<223> OTHER INFORMATION: 2'OMe
<220> FEATURE:
<221> NAME/KEY: misc_feature
<222> LOCATION: (15)..(15)
<223> OTHER INFORMATION: 3' chol
<220> FEATURE:
<221> NAME/KEY: modified_base
<222> LOCATION: (15)..(15)
<223> OTHER INFORMATION: 2'F

<400> SEQUENCE: 16
uucacaguuu ggaga                                                    15

<210> SEQ ID NO 17
<211> LENGTH: 20
<212> TYPE: RNA
<213> ORGANISM: Artificial Sequence
<220> FEATURE:
<223> OTHER INFORMATION: siRNA SBMA-5 antisense strand
<220> FEATURE:
<221> NAME/KEY: misc_feature
<222> LOCATION: (1)..(1)
<223> OTHER INFORMATION: 5' phosphate
<220> FEATURE:
<221> NAME/KEY: modified_base
<222> LOCATION: (1)..(1)
<223> OTHER INFORMATION: 2'OMe
<220> FEATURE:
<221> NAME/KEY: modified_base
<222> LOCATION: (2)..(2)
<223> OTHER INFORMATION: 2'F
<220> FEATURE:
<221> NAME/KEY: modified_base
<222> LOCATION: (3)..(3)
<223> OTHER INFORMATION: 2'OMe
<220> FEATURE:
<221> NAME/KEY: modified_base
<222> LOCATION: (4)..(4)
<223> OTHER INFORMATION: 2'F
<220> FEATURE:
<221> NAME/KEY: modified_base
<222> LOCATION: (5)..(5)
<223> OTHER INFORMATION: 2'OMe
<220> FEATURE:
<221> NAME/KEY: modified_base
<222> LOCATION: (6)..(6)
<223> OTHER INFORMATION: 2'F
<220> FEATURE:
<221> NAME/KEY: modified_base
<222> LOCATION: (7)..(7)
<223> OTHER INFORMATION: 2'OMe
<220> FEATURE:
<221> NAME/KEY: modified_base
<222> LOCATION: (8)..(8)
<223> OTHER INFORMATION: 2'F
<220> FEATURE:
<221> NAME/KEY: modified_base
<222> LOCATION: (9)..(9)
<223> OTHER INFORMATION: 2'OMe
<220> FEATURE:
<221> NAME/KEY: modified_base
<222> LOCATION: (10)..(10)
<223> OTHER INFORMATION: 2'F
<220> FEATURE:
<221> NAME/KEY: modified_base
<222> LOCATION: (11)..(11)
<223> OTHER INFORMATION: 2'OMe

```
<220> FEATURE:
<221> NAME/KEY: modified_base
<222> LOCATION: (12)..(12)
<223> OTHER INFORMATION: 2'F
<220> FEATURE:
<221> NAME/KEY: modified_base
<222> LOCATION: (13)..(13)
<223> OTHER INFORMATION: 2'OMe
<220> FEATURE:
<221> NAME/KEY: modified_base
<222> LOCATION: (14)..(14)
<223> OTHER INFORMATION: 2'F
<220> FEATURE:
<221> NAME/KEY: modified_base
<222> LOCATION: (15)..(15)
<223> OTHER INFORMATION: 2'OMe
<220> FEATURE:
<221> NAME/KEY: modified_base
<222> LOCATION: (16)..(16)
<223> OTHER INFORMATION: 2'F
<220> FEATURE:
<221> NAME/KEY: modified_base
<222> LOCATION: (17)..(17)
<223> OTHER INFORMATION: 2'OMe
<220> FEATURE:
<221> NAME/KEY: modified_base
<222> LOCATION: (18)..(18)
<223> OTHER INFORMATION: 2'F
<220> FEATURE:
<221> NAME/KEY: modified_base
<222> LOCATION: (19)..(19)
<223> OTHER INFORMATION: 2'OMe
<220> FEATURE:
<221> NAME/KEY: modified_base
<222> LOCATION: (20)..(20)
<223> OTHER INFORMATION: 2'F

<400> SEQUENCE: 17
gucuccaaac ugugaagcca                                                  20

<210> SEQ ID NO 18
<211> LENGTH: 15
<212> TYPE: RNA
<213> ORGANISM: Artificial Sequence
<220> FEATURE:
<223> OTHER INFORMATION: siRNA SBMA-5 sense strand
<220> FEATURE:
<221> NAME/KEY: modified_base
<222> LOCATION: (1)..(1)
<223> OTHER INFORMATION: 2'F
<220> FEATURE:
<221> NAME/KEY: modified_base
<222> LOCATION: (2)..(2)
<223> OTHER INFORMATION: 2'OMe
<220> FEATURE:
<221> NAME/KEY: modified_base
<222> LOCATION: (3)..(3)
<223> OTHER INFORMATION: 2'F
<220> FEATURE:
<221> NAME/KEY: modified_base
<222> LOCATION: (4)..(4)
<223> OTHER INFORMATION: 2'OMe
<220> FEATURE:
<221> NAME/KEY: modified_base
<222> LOCATION: (5)..(5)
<223> OTHER INFORMATION: 2'F
<220> FEATURE:
<221> NAME/KEY: modified_base
<222> LOCATION: (6)..(6)
<223> OTHER INFORMATION: 2'OMe
<220> FEATURE:
<221> NAME/KEY: modified_base
<222> LOCATION: (7)..(7)
<223> OTHER INFORMATION: 2'F
<220> FEATURE:
<221> NAME/KEY: modified_base
<222> LOCATION: (8)..(8)
```

```
<223> OTHER INFORMATION: 2'OMe
<220> FEATURE:
<221> NAME/KEY: modified_base
<222> LOCATION: (9)..(9)
<223> OTHER INFORMATION: 2'F
<220> FEATURE:
<221> NAME/KEY: modified_base
<222> LOCATION: (10)..(10)
<223> OTHER INFORMATION: 2'OMe
<220> FEATURE:
<221> NAME/KEY: modified_base
<222> LOCATION: (11)..(11)
<223> OTHER INFORMATION: 2'F
<220> FEATURE:
<221> NAME/KEY: modified_base
<222> LOCATION: (12)..(12)
<223> OTHER INFORMATION: 2'OMe
<220> FEATURE:
<221> NAME/KEY: modified_base
<222> LOCATION: (13)..(13)
<223> OTHER INFORMATION: 2'F
<220> FEATURE:
<221> NAME/KEY: modified_base
<222> LOCATION: (14)..(14)
<223> OTHER INFORMATION: 2'OMe
<220> FEATURE:
<221> NAME/KEY: misc_feature
<222> LOCATION: (15)..(15)
<223> OTHER INFORMATION: 3' chol
<220> FEATURE:
<221> NAME/KEY: modified_base
<222> LOCATION: (15)..(15)
<223> OTHER INFORMATION: 2'F

<400> SEQUENCE: 18
ucacaguuug gagac                                                    15

<210> SEQ ID NO 19
<211> LENGTH: 20
<212> TYPE: RNA
<213> ORGANISM: Artificial Sequence
<220> FEATURE:
<223> OTHER INFORMATION: siRNA SBMA-6 antisense strand
<220> FEATURE:
<221> NAME/KEY: misc_feature
<222> LOCATION: (1)..(1)
<223> OTHER INFORMATION: 5' phosphate
<220> FEATURE:
<221> NAME/KEY: modified_base
<222> LOCATION: (1)..(1)
<223> OTHER INFORMATION: 2'OMe
<220> FEATURE:
<221> NAME/KEY: modified_base
<222> LOCATION: (2)..(2)
<223> OTHER INFORMATION: 2'F
<220> FEATURE:
<221> NAME/KEY: modified_base
<222> LOCATION: (3)..(3)
<223> OTHER INFORMATION: 2'OMe
<220> FEATURE:
<221> NAME/KEY: modified_base
<222> LOCATION: (4)..(4)
<223> OTHER INFORMATION: 2'F
<220> FEATURE:
<221> NAME/KEY: modified_base
<222> LOCATION: (5)..(5)
<223> OTHER INFORMATION: 2'OMe
<220> FEATURE:
<221> NAME/KEY: modified_base
<222> LOCATION: (6)..(6)
<223> OTHER INFORMATION: 2'F
<220> FEATURE:
<221> NAME/KEY: modified_base
<222> LOCATION: (7)..(7)
<223> OTHER INFORMATION: 2'OMe
<220> FEATURE:
<221> NAME/KEY: modified_base
```

<222> LOCATION: (8)..(8)
<223> OTHER INFORMATION: 2'F
<220> FEATURE:
<221> NAME/KEY: modified_base
<222> LOCATION: (9)..(9)
<223> OTHER INFORMATION: 2'OMe
<220> FEATURE:
<221> NAME/KEY: modified_base
<222> LOCATION: (10)..(10)
<223> OTHER INFORMATION: 2'F
<220> FEATURE:
<221> NAME/KEY: modified_base
<222> LOCATION: (11)..(11)
<223> OTHER INFORMATION: 2'OMe
<220> FEATURE:
<221> NAME/KEY: modified_base
<222> LOCATION: (12)..(12)
<223> OTHER INFORMATION: 2'F
<220> FEATURE:
<221> NAME/KEY: modified_base
<222> LOCATION: (13)..(13)
<223> OTHER INFORMATION: 2'OMe
<220> FEATURE:
<221> NAME/KEY: modified_base
<222> LOCATION: (14)..(14)
<223> OTHER INFORMATION: 2'F
<220> FEATURE:
<221> NAME/KEY: modified_base
<222> LOCATION: (15)..(15)
<223> OTHER INFORMATION: 2'OMe
<220> FEATURE:
<221> NAME/KEY: modified_base
<222> LOCATION: (16)..(16)
<223> OTHER INFORMATION: 2'F
<220> FEATURE:
<221> NAME/KEY: modified_base
<222> LOCATION: (17)..(17)
<223> OTHER INFORMATION: 2'OMe
<220> FEATURE:
<221> NAME/KEY: modified_base
<222> LOCATION: (18)..(18)
<223> OTHER INFORMATION: 2'F
<220> FEATURE:
<221> NAME/KEY: modified_base
<222> LOCATION: (19)..(19)
<223> OTHER INFORMATION: 2'OMe
<220> FEATURE:
<221> NAME/KEY: modified_base
<222> LOCATION: (20)..(20)
<223> OTHER INFORMATION: 2'F

<400> SEQUENCE: 19
agucuccaaa cugugaagcc                                              20

<210> SEQ ID NO 20
<211> LENGTH: 15
<212> TYPE: RNA
<213> ORGANISM: Artificial Sequence
<220> FEATURE:
<223> OTHER INFORMATION: siRNA SBMA-6 sense strand
<220> FEATURE:
<221> NAME/KEY: modified_base
<222> LOCATION: (1)..(1)
<223> OTHER INFORMATION: 2'F
<220> FEATURE:
<221> NAME/KEY: modified_base
<222> LOCATION: (2)..(2)
<223> OTHER INFORMATION: 2'OMe
<220> FEATURE:
<221> NAME/KEY: modified_base
<222> LOCATION: (3)..(3)
<223> OTHER INFORMATION: 2'F
<220> FEATURE:
<221> NAME/KEY: modified_base
<222> LOCATION: (4)..(4)
<223> OTHER INFORMATION: 2'OMe
<220> FEATURE:

```
<221> NAME/KEY: modified_base
<222> LOCATION: (5)..(5)
<223> OTHER INFORMATION: 2'F
<220> FEATURE:
<221> NAME/KEY: modified_base
<222> LOCATION: (6)..(6)
<223> OTHER INFORMATION: 2'OMe
<220> FEATURE:
<221> NAME/KEY: modified_base
<222> LOCATION: (7)..(7)
<223> OTHER INFORMATION: 2'F
<220> FEATURE:
<221> NAME/KEY: modified_base
<222> LOCATION: (8)..(8)
<223> OTHER INFORMATION: 2'OMe
<220> FEATURE:
<221> NAME/KEY: modified_base
<222> LOCATION: (9)..(9)
<223> OTHER INFORMATION: 2'F
<220> FEATURE:
<221> NAME/KEY: modified_base
<222> LOCATION: (10)..(10)
<223> OTHER INFORMATION: 2'OMe
<220> FEATURE:
<221> NAME/KEY: modified_base
<222> LOCATION: (11)..(11)
<223> OTHER INFORMATION: 2'F
<220> FEATURE:
<221> NAME/KEY: modified_base
<222> LOCATION: (12)..(12)
<223> OTHER INFORMATION: 2'OMe
<220> FEATURE:
<221> NAME/KEY: modified_base
<222> LOCATION: (13)..(13)
<223> OTHER INFORMATION: 2'F
<220> FEATURE:
<221> NAME/KEY: modified_base
<222> LOCATION: (14)..(14)
<223> OTHER INFORMATION: 2'OMe
<220> FEATURE:
<221> NAME/KEY: misc_feature
<222> LOCATION: (15)..(15)
<223> OTHER INFORMATION: 3' chol
<220> FEATURE:
<221> NAME/KEY: modified_base
<222> LOCATION: (15)..(15)
<223> OTHER INFORMATION: 2'F

<400> SEQUENCE: 20
cacaguuugg agacu                                                    15

<210> SEQ ID NO 21
<211> LENGTH: 20
<212> TYPE: RNA
<213> ORGANISM: Artificial Sequence
<220> FEATURE:
<223> OTHER INFORMATION: siRNA SBMA-7 antisense strand
<220> FEATURE:
<221> NAME/KEY: misc_feature
<222> LOCATION: (1)..(1)
<223> OTHER INFORMATION: 5' phosphate
<220> FEATURE:
<221> NAME/KEY: misc_feature
<222> LOCATION: (1)..(1)
<223> OTHER INFORMATION: 2'OMe
<220> FEATURE:
<221> NAME/KEY: misc_feature
<222> LOCATION: (2)..(2)
<223> OTHER INFORMATION: 2'F
<220> FEATURE:
<221> NAME/KEY: misc_feature
<222> LOCATION: (3)..(3)
<223> OTHER INFORMATION: 2'OMe
<220> FEATURE:
<221> NAME/KEY: misc_feature
<222> LOCATION: (4)..(4)
<223> OTHER INFORMATION: 2'F
```

-continued

```
<220> FEATURE:
<221> NAME/KEY: misc_feature
<222> LOCATION: (5)..(5)
<223> OTHER INFORMATION: 2'OMe
<220> FEATURE:
<221> NAME/KEY: misc_feature
<222> LOCATION: (6)..(6)
<223> OTHER INFORMATION: 2'F
<220> FEATURE:
<221> NAME/KEY: misc_feature
<222> LOCATION: (7)..(7)
<223> OTHER INFORMATION: 2'OMe
<220> FEATURE:
<221> NAME/KEY: misc_feature
<222> LOCATION: (8)..(8)
<223> OTHER INFORMATION: 2'F
<220> FEATURE:
<221> NAME/KEY: misc_feature
<222> LOCATION: (9)..(9)
<223> OTHER INFORMATION: 2'OMe
<220> FEATURE:
<221> NAME/KEY: misc_feature
<222> LOCATION: (10)..(10)
<223> OTHER INFORMATION: 2'F
<220> FEATURE:
<221> NAME/KEY: misc_feature
<222> LOCATION: (11)..(11)
<223> OTHER INFORMATION: 2'OMe
<220> FEATURE:
<221> NAME/KEY: misc_feature
<222> LOCATION: (12)..(12)
<223> OTHER INFORMATION: 2'F
<220> FEATURE:
<221> NAME/KEY: misc_feature
<222> LOCATION: (13)..(13)
<223> OTHER INFORMATION: 2'OMe
<220> FEATURE:
<221> NAME/KEY: misc_feature
<222> LOCATION: (14)..(14)
<223> OTHER INFORMATION: 2'F
<220> FEATURE:
<221> NAME/KEY: misc_feature
<222> LOCATION: (15)..(15)
<223> OTHER INFORMATION: 2'OMe
<220> FEATURE:
<221> NAME/KEY: misc_feature
<222> LOCATION: (16)..(16)
<223> OTHER INFORMATION: 2'F
<220> FEATURE:
<221> NAME/KEY: misc_feature
<222> LOCATION: (17)..(17)
<223> OTHER INFORMATION: 2'OMe
<220> FEATURE:
<221> NAME/KEY: misc_feature
<222> LOCATION: (18)..(18)
<223> OTHER INFORMATION: 2'F
<220> FEATURE:
<221> NAME/KEY: misc_feature
<222> LOCATION: (19)..(19)
<223> OTHER INFORMATION: 2'OMe
<220> FEATURE:
<221> NAME/KEY: misc_feature
<222> LOCATION: (20)..(20)
<223> OTHER INFORMATION: 2'F

<400> SEQUENCE: 21
cagucuccaa acugugaagc                                              20

<210> SEQ ID NO 22
<211> LENGTH: 15
<212> TYPE: RNA
<213> ORGANISM: Artificial Sequence
<220> FEATURE:
<223> OTHER INFORMATION: siRNA SBMA-7 sense strand
<220> FEATURE:
<221> NAME/KEY: modified_base
<222> LOCATION: (1)..(1)
```

```
<223> OTHER INFORMATION: 2'F
<220> FEATURE:
<221> NAME/KEY: modified_base
<222> LOCATION: (2)..(2)
<223> OTHER INFORMATION: 2'OMe
<220> FEATURE:
<221> NAME/KEY: modified_base
<222> LOCATION: (3)..(3)
<223> OTHER INFORMATION: 2'F
<220> FEATURE:
<221> NAME/KEY: modified_base
<222> LOCATION: (4)..(4)
<223> OTHER INFORMATION: 2'OMe
<220> FEATURE:
<221> NAME/KEY: modified_base
<222> LOCATION: (5)..(5)
<223> OTHER INFORMATION: 2'F
<220> FEATURE:
<221> NAME/KEY: modified_base
<222> LOCATION: (6)..(6)
<223> OTHER INFORMATION: 2'OMe
<220> FEATURE:
<221> NAME/KEY: modified_base
<222> LOCATION: (7)..(7)
<223> OTHER INFORMATION: 2'F
<220> FEATURE:
<221> NAME/KEY: modified_base
<222> LOCATION: (8)..(8)
<223> OTHER INFORMATION: 2'OMe
<220> FEATURE:
<221> NAME/KEY: modified_base
<222> LOCATION: (9)..(9)
<223> OTHER INFORMATION: 2'F
<220> FEATURE:
<221> NAME/KEY: modified_base
<222> LOCATION: (10)..(10)
<223> OTHER INFORMATION: 2'OMe
<220> FEATURE:
<221> NAME/KEY: modified_base
<222> LOCATION: (11)..(11)
<223> OTHER INFORMATION: 2'F
<220> FEATURE:
<221> NAME/KEY: modified_base
<222> LOCATION: (12)..(12)
<223> OTHER INFORMATION: 2'OMe
<220> FEATURE:
<221> NAME/KEY: modified_base
<222> LOCATION: (13)..(13)
<223> OTHER INFORMATION: 2'F
<220> FEATURE:
<221> NAME/KEY: modified_base
<222> LOCATION: (14)..(14)
<223> OTHER INFORMATION: 2'OMe
<220> FEATURE:
<221> NAME/KEY: misc_feature
<222> LOCATION: (15)..(15)
<223> OTHER INFORMATION: 3' chol
<220> FEATURE:
<221> NAME/KEY: modified_base
<222> LOCATION: (15)..(15)
<223> OTHER INFORMATION: 2'F

<400> SEQUENCE: 22
acaguuugga gacug                                                15

<210> SEQ ID NO 23
<211> LENGTH: 20
<212> TYPE: RNA
<213> ORGANISM: Artificial Sequence
<220> FEATURE:
<223> OTHER INFORMATION: siRNA SBMA-8 antisense strand
<220> FEATURE:
<221> NAME/KEY: misc_feature
<222> LOCATION: (1)..(1)
<223> OTHER INFORMATION: 5' phosphate
<220> FEATURE:
<221> NAME/KEY: modified_base
```

```
<222> LOCATION: (1)..(1)
<223> OTHER INFORMATION: 2'OMe
<220> FEATURE:
<221> NAME/KEY: modified_base
<222> LOCATION: (2)..(2)
<223> OTHER INFORMATION: 2'F
<220> FEATURE:
<221> NAME/KEY: modified_base
<222> LOCATION: (3)..(3)
<223> OTHER INFORMATION: 2'OMe
<220> FEATURE:
<221> NAME/KEY: modified_base
<222> LOCATION: (4)..(4)
<223> OTHER INFORMATION: 2'F
<220> FEATURE:
<221> NAME/KEY: modified_base
<222> LOCATION: (5)..(5)
<223> OTHER INFORMATION: 2'OMe
<220> FEATURE:
<221> NAME/KEY: modified_base
<222> LOCATION: (6)..(6)
<223> OTHER INFORMATION: 2'F
<220> FEATURE:
<221> NAME/KEY: modified_base
<222> LOCATION: (7)..(7)
<223> OTHER INFORMATION: 2'OMe
<220> FEATURE:
<221> NAME/KEY: modified_base
<222> LOCATION: (8)..(8)
<223> OTHER INFORMATION: 2'F
<220> FEATURE:
<221> NAME/KEY: modified_base
<222> LOCATION: (9)..(9)
<223> OTHER INFORMATION: 2'OMe
<220> FEATURE:
<221> NAME/KEY: modified_base
<222> LOCATION: (10)..(10)
<223> OTHER INFORMATION: 2'F
<220> FEATURE:
<221> NAME/KEY: modified_base
<222> LOCATION: (11)..(11)
<223> OTHER INFORMATION: 2'OMe
<220> FEATURE:
<221> NAME/KEY: modified_base
<222> LOCATION: (12)..(12)
<223> OTHER INFORMATION: 2'F
<220> FEATURE:
<221> NAME/KEY: modified_base
<222> LOCATION: (13)..(13)
<223> OTHER INFORMATION: 2'OMe
<220> FEATURE:
<221> NAME/KEY: modified_base
<222> LOCATION: (14)..(14)
<223> OTHER INFORMATION: 2'F
<220> FEATURE:
<221> NAME/KEY: modified_base
<222> LOCATION: (15)..(15)
<223> OTHER INFORMATION: 2'OMe
<220> FEATURE:
<221> NAME/KEY: modified_base
<222> LOCATION: (16)..(16)
<223> OTHER INFORMATION: 2'F
<220> FEATURE:
<221> NAME/KEY: modified_base
<222> LOCATION: (17)..(17)
<223> OTHER INFORMATION: 2'OMe
<220> FEATURE:
<221> NAME/KEY: modified_base
<222> LOCATION: (18)..(18)
<223> OTHER INFORMATION: 2'F
<220> FEATURE:
<221> NAME/KEY: modified_base
<222> LOCATION: (19)..(19)
<223> OTHER INFORMATION: 2'OMe
<220> FEATURE:
<221> NAME/KEY: modified_base
<222> LOCATION: (20)..(20)
<223> OTHER INFORMATION: 2'F
```

-continued

```
<400> SEQUENCE: 23
gcagucucca aacugugaag                                           20

<210> SEQ ID NO 24
<211> LENGTH: 15
<212> TYPE: RNA
<213> ORGANISM: Artificial Sequence
<220> FEATURE:
<223> OTHER INFORMATION: siRNA SBMA-8 sense strand
<220> FEATURE:
<221> NAME/KEY: modified_base
<222> LOCATION: (1)..(1)
<223> OTHER INFORMATION: 2'F
<220> FEATURE:
<221> NAME/KEY: modified_base
<222> LOCATION: (2)..(2)
<223> OTHER INFORMATION: 2'OMe
<220> FEATURE:
<221> NAME/KEY: modified_base
<222> LOCATION: (3)..(3)
<223> OTHER INFORMATION: 2'F
<220> FEATURE:
<221> NAME/KEY: modified_base
<222> LOCATION: (4)..(4)
<223> OTHER INFORMATION: 2'OMe
<220> FEATURE:
<221> NAME/KEY: modified_base
<222> LOCATION: (5)..(5)
<223> OTHER INFORMATION: 2'F
<220> FEATURE:
<221> NAME/KEY: modified_base
<222> LOCATION: (6)..(6)
<223> OTHER INFORMATION: 2'OMe
<220> FEATURE:
<221> NAME/KEY: modified_base
<222> LOCATION: (7)..(7)
<223> OTHER INFORMATION: 2'F
<220> FEATURE:
<221> NAME/KEY: modified_base
<222> LOCATION: (8)..(8)
<223> OTHER INFORMATION: 2'OMe
<220> FEATURE:
<221> NAME/KEY: modified_base
<222> LOCATION: (9)..(9)
<223> OTHER INFORMATION: 2'F
<220> FEATURE:
<221> NAME/KEY: modified_base
<222> LOCATION: (10)..(10)
<223> OTHER INFORMATION: 2'OMe
<220> FEATURE:
<221> NAME/KEY: modified_base
<222> LOCATION: (11)..(11)
<223> OTHER INFORMATION: 2'F
<220> FEATURE:
<221> NAME/KEY: modified_base
<222> LOCATION: (12)..(12)
<223> OTHER INFORMATION: 2'OMe
<220> FEATURE:
<221> NAME/KEY: modified_base
<222> LOCATION: (13)..(13)
<223> OTHER INFORMATION: 2'F
<220> FEATURE:
<221> NAME/KEY: modified_base
<222> LOCATION: (14)..(14)
<223> OTHER INFORMATION: 2'OMe
<220> FEATURE:
<221> NAME/KEY: misc_feature
<222> LOCATION: (15)..(15)
<223> OTHER INFORMATION: 3' chol
<220> FEATURE:
<221> NAME/KEY: modified_base
<222> LOCATION: (15)..(15)
<223> OTHER INFORMATION: 2'F

<400> SEQUENCE: 24
caguuuggag acugc                                                15
```

```
<210> SEQ ID NO 25
<211> LENGTH: 20
<212> TYPE: RNA
<213> ORGANISM: Artificial Sequence
<220> FEATURE:
<223> OTHER INFORMATION: siRNA SBMA-9 antisense strand
<220> FEATURE:
<221> NAME/KEY: misc_feature
<222> LOCATION: (1)..(1)
<223> OTHER INFORMATION: 5' phosphate
<220> FEATURE:
<221> NAME/KEY: modified_base
<222> LOCATION: (1)..(1)
<223> OTHER INFORMATION: 2'OMe
<220> FEATURE:
<221> NAME/KEY: modified_base
<222> LOCATION: (2)..(2)
<223> OTHER INFORMATION: 2'F
<220> FEATURE:
<221> NAME/KEY: modified_base
<222> LOCATION: (3)..(3)
<223> OTHER INFORMATION: 2'OMe
<220> FEATURE:
<221> NAME/KEY: modified_base
<222> LOCATION: (4)..(4)
<223> OTHER INFORMATION: 2'F
<220> FEATURE:
<221> NAME/KEY: modified_base
<222> LOCATION: (5)..(5)
<223> OTHER INFORMATION: 2'OMe
<220> FEATURE:
<221> NAME/KEY: modified_base
<222> LOCATION: (6)..(6)
<223> OTHER INFORMATION: 2'F
<220> FEATURE:
<221> NAME/KEY: modified_base
<222> LOCATION: (7)..(7)
<223> OTHER INFORMATION: 2'OMe
<220> FEATURE:
<221> NAME/KEY: modified_base
<222> LOCATION: (8)..(8)
<223> OTHER INFORMATION: 2'F
<220> FEATURE:
<221> NAME/KEY: modified_base
<222> LOCATION: (9)..(9)
<223> OTHER INFORMATION: 2'OMe
<220> FEATURE:
<221> NAME/KEY: modified_base
<222> LOCATION: (10)..(10)
<223> OTHER INFORMATION: 2'F
<220> FEATURE:
<221> NAME/KEY: modified_base
<222> LOCATION: (11)..(11)
<223> OTHER INFORMATION: 2'OMe
<220> FEATURE:
<221> NAME/KEY: modified_base
<222> LOCATION: (12)..(12)
<223> OTHER INFORMATION: 2'F
<220> FEATURE:
<221> NAME/KEY: modified_base
<222> LOCATION: (13)..(13)
<223> OTHER INFORMATION: 2'OMe
<220> FEATURE:
<221> NAME/KEY: modified_base
<222> LOCATION: (14)..(14)
<223> OTHER INFORMATION: 2'F
<220> FEATURE:
<221> NAME/KEY: modified_base
<222> LOCATION: (15)..(15)
<223> OTHER INFORMATION: 2'OMe
<220> FEATURE:
<221> NAME/KEY: modified_base
<222> LOCATION: (16)..(16)
<223> OTHER INFORMATION: 2'F
<220> FEATURE:
<221> NAME/KEY: modified_base
<222> LOCATION: (17)..(17)
```

```
<223> OTHER INFORMATION: 2'OMe
<220> FEATURE:
<221> NAME/KEY: modified_base
<222> LOCATION: (18)..(18)
<223> OTHER INFORMATION: 2'F
<220> FEATURE:
<221> NAME/KEY: modified_base
<222> LOCATION: (19)..(19)
<223> OTHER INFORMATION: 2'OMe
<220> FEATURE:
<221> NAME/KEY: modified_base
<222> LOCATION: (20)..(20)
<223> OTHER INFORMATION: 2'F

<400> SEQUENCE: 25
ggcagucucc aaacugugaa                                              20

<210> SEQ ID NO 26
<211> LENGTH: 15
<212> TYPE: RNA
<213> ORGANISM: Artificial Sequence
<220> FEATURE:
<223> OTHER INFORMATION: siRNA SBMA-9 sense strand
<220> FEATURE:
<221> NAME/KEY: modified_base
<222> LOCATION: (1)..(1)
<223> OTHER INFORMATION: 2'F
<220> FEATURE:
<221> NAME/KEY: modified_base
<222> LOCATION: (2)..(2)
<223> OTHER INFORMATION: 2'OMe
<220> FEATURE:
<221> NAME/KEY: modified_base
<222> LOCATION: (3)..(3)
<223> OTHER INFORMATION: 2'F
<220> FEATURE:
<221> NAME/KEY: modified_base
<222> LOCATION: (4)..(4)
<223> OTHER INFORMATION: 2'OMe
<220> FEATURE:
<221> NAME/KEY: modified_base
<222> LOCATION: (5)..(5)
<223> OTHER INFORMATION: 2'F
<220> FEATURE:
<221> NAME/KEY: modified_base
<222> LOCATION: (6)..(6)
<223> OTHER INFORMATION: 2'OMe
<220> FEATURE:
<221> NAME/KEY: modified_base
<222> LOCATION: (7)..(7)
<223> OTHER INFORMATION: 2'F
<220> FEATURE:
<221> NAME/KEY: modified_base
<222> LOCATION: (8)..(8)
<223> OTHER INFORMATION: 2'OMe
<220> FEATURE:
<221> NAME/KEY: modified_base
<222> LOCATION: (9)..(9)
<223> OTHER INFORMATION: 2'F
<220> FEATURE:
<221> NAME/KEY: modified_base
<222> LOCATION: (10)..(10)
<223> OTHER INFORMATION: 2'OMe
<220> FEATURE:
<221> NAME/KEY: modified_base
<222> LOCATION: (11)..(11)
<223> OTHER INFORMATION: 2'F
<220> FEATURE:
<221> NAME/KEY: modified_base
<222> LOCATION: (12)..(12)
<223> OTHER INFORMATION: 2'OMe
<220> FEATURE:
<221> NAME/KEY: modified_base
<222> LOCATION: (13)..(13)
<223> OTHER INFORMATION: 2'F
<220> FEATURE:
<221> NAME/KEY: modified_base
```

-continued

```
<222> LOCATION: (14)..(14)
<223> OTHER INFORMATION: 2'OMe
<220> FEATURE:
<221> NAME/KEY: misc_feature
<222> LOCATION: (15)..(15)
<223> OTHER INFORMATION: 3' chol
<220> FEATURE:
<221> NAME/KEY: modified_base
<222> LOCATION: (15)..(15)
<223> OTHER INFORMATION: 2'F

<400> SEQUENCE: 26
aguuuggaga cugcc                                                      15

<210> SEQ ID NO 27
<211> LENGTH: 20
<212> TYPE: RNA
<213> ORGANISM: Artificial Sequence
<220> FEATURE:
<223> OTHER INFORMATION: siRNA SBMA-10 antisense strand
<220> FEATURE:
<221> NAME/KEY: misc_feature
<222> LOCATION: (1)..(1)
<223> OTHER INFORMATION: 5' phosphate
<220> FEATURE:
<221> NAME/KEY: modified_base
<222> LOCATION: (1)..(1)
<223> OTHER INFORMATION: 2'OMe
<220> FEATURE:
<221> NAME/KEY: modified_base
<222> LOCATION: (2)..(2)
<223> OTHER INFORMATION: 2'F
<220> FEATURE:
<221> NAME/KEY: modified_base
<222> LOCATION: (3)..(3)
<223> OTHER INFORMATION: 2'OMe
<220> FEATURE:
<221> NAME/KEY: modified_base
<222> LOCATION: (4)..(4)
<223> OTHER INFORMATION: 2'F
<220> FEATURE:
<221> NAME/KEY: modified_base
<222> LOCATION: (5)..(5)
<223> OTHER INFORMATION: 2'OMe
<220> FEATURE:
<221> NAME/KEY: modified_base
<222> LOCATION: (6)..(6)
<223> OTHER INFORMATION: 2'F
<220> FEATURE:
<221> NAME/KEY: modified_base
<222> LOCATION: (7)..(7)
<223> OTHER INFORMATION: 2'OMe
<220> FEATURE:
<221> NAME/KEY: modified_base
<222> LOCATION: (8)..(8)
<223> OTHER INFORMATION: 2'F
<220> FEATURE:
<221> NAME/KEY: modified_base
<222> LOCATION: (9)..(9)
<223> OTHER INFORMATION: 2'OMe
<220> FEATURE:
<221> NAME/KEY: modified_base
<222> LOCATION: (10)..(10)
<223> OTHER INFORMATION: 2'F
<220> FEATURE:
<221> NAME/KEY: modified_base
<222> LOCATION: (11)..(11)
<223> OTHER INFORMATION: 2'OMe
<220> FEATURE:
<221> NAME/KEY: modified_base
<222> LOCATION: (12)..(12)
<223> OTHER INFORMATION: 2'F
<220> FEATURE:
<221> NAME/KEY: modified_base
<222> LOCATION: (13)..(13)
<223> OTHER INFORMATION: 2'OMe
<220> FEATURE:
```

```
<221> NAME/KEY: modified_base
<222> LOCATION: (14)..(14)
<223> OTHER INFORMATION: 2'F
<220> FEATURE:
<221> NAME/KEY: modified_base
<222> LOCATION: (15)..(15)
<223> OTHER INFORMATION: 2'OMe
<220> FEATURE:
<221> NAME/KEY: modified_base
<222> LOCATION: (16)..(16)
<223> OTHER INFORMATION: 2'F
<220> FEATURE:
<221> NAME/KEY: modified_base
<222> LOCATION: (17)..(17)
<223> OTHER INFORMATION: 2'OMe
<220> FEATURE:
<221> NAME/KEY: modified_base
<222> LOCATION: (18)..(18)
<223> OTHER INFORMATION: 2'F
<220> FEATURE:
<221> NAME/KEY: modified_base
<222> LOCATION: (19)..(19)
<223> OTHER INFORMATION: 2'OMe
<220> FEATURE:
<221> NAME/KEY: modified_base
<222> LOCATION: (20)..(20)
<223> OTHER INFORMATION: 2'F

<400> SEQUENCE: 27
uggcagucuc caaacuguga                                               20

<210> SEQ ID NO 28
<211> LENGTH: 15
<212> TYPE: RNA
<213> ORGANISM: Artificial Sequence
<220> FEATURE:
<223> OTHER INFORMATION: siRNA SBMA-10 sense strand
<220> FEATURE:
<221> NAME/KEY: modified_base
<222> LOCATION: (1)..(1)
<223> OTHER INFORMATION: 2'F
<220> FEATURE:
<221> NAME/KEY: modified_base
<222> LOCATION: (2)..(2)
<223> OTHER INFORMATION: 2'OMe
<220> FEATURE:
<221> NAME/KEY: modified_base
<222> LOCATION: (3)..(3)
<223> OTHER INFORMATION: 2'F
<220> FEATURE:
<221> NAME/KEY: modified_base
<222> LOCATION: (4)..(4)
<223> OTHER INFORMATION: 2'OMe
<220> FEATURE:
<221> NAME/KEY: modified_base
<222> LOCATION: (5)..(5)
<223> OTHER INFORMATION: 2'F
<220> FEATURE:
<221> NAME/KEY: modified_base
<222> LOCATION: (6)..(6)
<223> OTHER INFORMATION: 2'OMe
<220> FEATURE:
<221> NAME/KEY: modified_base
<222> LOCATION: (7)..(7)
<223> OTHER INFORMATION: 2'F
<220> FEATURE:
<221> NAME/KEY: modified_base
<222> LOCATION: (8)..(8)
<223> OTHER INFORMATION: 2'OMe
<220> FEATURE:
<221> NAME/KEY: modified_base
<222> LOCATION: (9)..(9)
<223> OTHER INFORMATION: 2'F
<220> FEATURE:
<221> NAME/KEY: modified_base
<222> LOCATION: (10)..(10)
<223> OTHER INFORMATION: 2'OMe
```

```
<220> FEATURE:
<221> NAME/KEY: modified_base
<222> LOCATION: (11)..(11)
<223> OTHER INFORMATION: 2'F
<220> FEATURE:
<221> NAME/KEY: modified_base
<222> LOCATION: (12)..(12)
<223> OTHER INFORMATION: 2'OMe
<220> FEATURE:
<221> NAME/KEY: modified_base
<222> LOCATION: (13)..(13)
<223> OTHER INFORMATION: 2'F
<220> FEATURE:
<221> NAME/KEY: modified_base
<222> LOCATION: (14)..(14)
<223> OTHER INFORMATION: 2'OMe
<220> FEATURE:
<221> NAME/KEY: misc_feature
<222> LOCATION: (15)..(15)
<223> OTHER INFORMATION: 3' chol
<220> FEATURE:
<221> NAME/KEY: modified_base
<222> LOCATION: (15)..(15)
<223> OTHER INFORMATION: 2'F

<400> SEQUENCE: 28
guuuggagac ugcca                                                      15

<210> SEQ ID NO 29
<211> LENGTH: 20
<212> TYPE: RNA
<213> ORGANISM: Artificial Sequence
<220> FEATURE:
<223> OTHER INFORMATION: siRNA SBMA-11 antisense strand
<220> FEATURE:
<221> NAME/KEY: misc_feature
<222> LOCATION: (1)..(1)
<223> OTHER INFORMATION: 5' phosphate
<220> FEATURE:
<221> NAME/KEY: modified_base
<222> LOCATION: (1)..(1)
<223> OTHER INFORMATION: 2'OMe
<220> FEATURE:
<221> NAME/KEY: modified_base
<222> LOCATION: (2)..(2)
<223> OTHER INFORMATION: 2'F
<220> FEATURE:
<221> NAME/KEY: modified_base
<222> LOCATION: (3)..(3)
<223> OTHER INFORMATION: 2'OMe
<220> FEATURE:
<221> NAME/KEY: modified_base
<222> LOCATION: (4)..(4)
<223> OTHER INFORMATION: 2'F
<220> FEATURE:
<221> NAME/KEY: modified_base
<222> LOCATION: (5)..(5)
<223> OTHER INFORMATION: 2'OMe
<220> FEATURE:
<221> NAME/KEY: modified_base
<222> LOCATION: (6)..(6)
<223> OTHER INFORMATION: 2'F
<220> FEATURE:
<221> NAME/KEY: modified_base
<222> LOCATION: (7)..(7)
<223> OTHER INFORMATION: 2'OMe
<220> FEATURE:
<221> NAME/KEY: modified_base
<222> LOCATION: (8)..(8)
<223> OTHER INFORMATION: 2'F
<220> FEATURE:
<221> NAME/KEY: modified_base
<222> LOCATION: (9)..(9)
<223> OTHER INFORMATION: 2'OMe
<220> FEATURE:
<221> NAME/KEY: modified_base
<222> LOCATION: (10)..(10)
```

```
<223> OTHER INFORMATION: 2'F
<220> FEATURE:
<221> NAME/KEY: modified_base
<222> LOCATION: (11)..(11)
<223> OTHER INFORMATION: 2'OMe
<220> FEATURE:
<221> NAME/KEY: modified_base
<222> LOCATION: (12)..(12)
<223> OTHER INFORMATION: 2'F
<220> FEATURE:
<221> NAME/KEY: modified_base
<222> LOCATION: (13)..(13)
<223> OTHER INFORMATION: 2'OMe
<220> FEATURE:
<221> NAME/KEY: modified_base
<222> LOCATION: (14)..(14)
<223> OTHER INFORMATION: 2'F
<220> FEATURE:
<221> NAME/KEY: modified_base
<222> LOCATION: (15)..(15)
<223> OTHER INFORMATION: 2'OMe
<220> FEATURE:
<221> NAME/KEY: modified_base
<222> LOCATION: (16)..(16)
<223> OTHER INFORMATION: 2'F
<220> FEATURE:
<221> NAME/KEY: modified_base
<222> LOCATION: (17)..(17)
<223> OTHER INFORMATION: 2'OMe
<220> FEATURE:
<221> NAME/KEY: modified_base
<222> LOCATION: (18)..(18)
<223> OTHER INFORMATION: 2'F
<220> FEATURE:
<221> NAME/KEY: modified_base
<222> LOCATION: (19)..(19)
<223> OTHER INFORMATION: 2'OMe
<220> FEATURE:
<221> NAME/KEY: modified_base
<222> LOCATION: (20)..(20)
<223> OTHER INFORMATION: 2'F

<400> SEQUENCE: 29
cuggcagucu ccaaacugug                                               20

<210> SEQ ID NO 30
<211> LENGTH: 15
<212> TYPE: RNA
<213> ORGANISM: Artificial Sequence
<220> FEATURE:
<223> OTHER INFORMATION: siRNA SBMA-11 sense strand
<220> FEATURE:
<221> NAME/KEY: modified_base
<222> LOCATION: (1)..(1)
<223> OTHER INFORMATION: 2'F
<220> FEATURE:
<221> NAME/KEY: modified_base
<222> LOCATION: (2)..(2)
<223> OTHER INFORMATION: 2'OMe
<220> FEATURE:
<221> NAME/KEY: modified_base
<222> LOCATION: (3)..(3)
<223> OTHER INFORMATION: 2'F
<220> FEATURE:
<221> NAME/KEY: modified_base
<222> LOCATION: (4)..(4)
<223> OTHER INFORMATION: 2'OMe
<220> FEATURE:
<221> NAME/KEY: modified_base
<222> LOCATION: (5)..(5)
<223> OTHER INFORMATION: 2'F
<220> FEATURE:
<221> NAME/KEY: modified_base
<222> LOCATION: (6)..(6)
<223> OTHER INFORMATION: 2'OMe
<220> FEATURE:
<221> NAME/KEY: modified_base
```

```
<222> LOCATION: (7)..(7)
<223> OTHER INFORMATION: 2'F
<220> FEATURE:
<221> NAME/KEY: modified_base
<222> LOCATION: (8)..(8)
<223> OTHER INFORMATION: 2'OMe
<220> FEATURE:
<221> NAME/KEY: modified_base
<222> LOCATION: (9)..(9)
<223> OTHER INFORMATION: 2'F
<220> FEATURE:
<221> NAME/KEY: modified_base
<222> LOCATION: (10)..(10)
<223> OTHER INFORMATION: 2'OMe
<220> FEATURE:
<221> NAME/KEY: modified_base
<222> LOCATION: (11)..(11)
<223> OTHER INFORMATION: 2'F
<220> FEATURE:
<221> NAME/KEY: modified_base
<222> LOCATION: (12)..(12)
<223> OTHER INFORMATION: 2'OMe
<220> FEATURE:
<221> NAME/KEY: modified_base
<222> LOCATION: (13)..(13)
<223> OTHER INFORMATION: 2'F
<220> FEATURE:
<221> NAME/KEY: modified_base
<222> LOCATION: (14)..(14)
<223> OTHER INFORMATION: 2'OMe
<220> FEATURE:
<221> NAME/KEY: misc_feature
<222> LOCATION: (15)..(15)
<223> OTHER INFORMATION: 3' chol
<220> FEATURE:
<221> NAME/KEY: modified_base
<222> LOCATION: (15)..(15)
<223> OTHER INFORMATION: 2'F

<400> SEQUENCE: 30
uuuggagacu gccag                                              15

<210> SEQ ID NO 31
<211> LENGTH: 15
<212> TYPE: RNA
<213> ORGANISM: Artificial Sequence
<220> FEATURE:
<223> OTHER INFORMATION: siRNA AR-2 sense strand
<220> FEATURE:
<221> NAME/KEY: modified_base
<222> LOCATION: (1)..(1)
<223> OTHER INFORMATION: 2'F
<220> FEATURE:
<221> NAME/KEY: modified_base
<222> LOCATION: (2)..(2)
<223> OTHER INFORMATION: 2'OMe
<220> FEATURE:
<221> NAME/KEY: modified_base
<222> LOCATION: (3)..(3)
<223> OTHER INFORMATION: 2'F
<220> FEATURE:
<221> NAME/KEY: modified_base
<222> LOCATION: (4)..(4)
<223> OTHER INFORMATION: 2'OMe
<220> FEATURE:
<221> NAME/KEY: modified_base
<222> LOCATION: (5)..(5)
<223> OTHER INFORMATION: 2'F
<220> FEATURE:
<221> NAME/KEY: modified_base
<222> LOCATION: (6)..(6)
<223> OTHER INFORMATION: 2'OMe
<220> FEATURE:
<221> NAME/KEY: modified_base
<222> LOCATION: (7)..(7)
<223> OTHER INFORMATION: 2'F
<220> FEATURE:
```

```
<221> NAME/KEY: modified_base
<222> LOCATION: (8)..(8)
<223> OTHER INFORMATION: 2'OMe
<220> FEATURE:
<221> NAME/KEY: modified_base
<222> LOCATION: (9)..(9)
<223> OTHER INFORMATION: 2'F
<220> FEATURE:
<221> NAME/KEY: modified_base
<222> LOCATION: (10)..(10)
<223> OTHER INFORMATION: 2'OMe
<220> FEATURE:
<221> NAME/KEY: modified_base
<222> LOCATION: (11)..(11)
<223> OTHER INFORMATION: 2'F
<220> FEATURE:
<221> NAME/KEY: modified_base
<222> LOCATION: (12)..(12)
<223> OTHER INFORMATION: 2'OMe
<220> FEATURE:
<221> NAME/KEY: modified_base
<222> LOCATION: (13)..(13)
<223> OTHER INFORMATION: 2'F
<220> FEATURE:
<221> NAME/KEY: modified_base
<222> LOCATION: (14)..(14)
<223> OTHER INFORMATION: 2'OMe
<220> FEATURE:
<221> NAME/KEY: misc_feature
<222> LOCATION: (15)..(15)
<223> OTHER INFORMATION: 3' PC-DCA (Phosphocholine Docosanoic Acid)
<220> FEATURE:
<221> NAME/KEY: modified_base
<222> LOCATION: (15)..(15)
<223> OTHER INFORMATION: 2'F

<400> SEQUENCE: 31
ggcuucacag uuugg                                                    15

<210> SEQ ID NO 32
<211> LENGTH: 20
<212> TYPE: RNA
<213> ORGANISM: Artificial Sequence
<220> FEATURE:
<223> OTHER INFORMATION: siRNA AR-2 antisense strand
<220> FEATURE:
<221> NAME/KEY: misc_feature
<222> LOCATION: (1)..(1)
<223> OTHER INFORMATION: 5' VP (Vinylphosphonate)
<220> FEATURE:
<221> NAME/KEY: modified_base
<222> LOCATION: (1)..(1)
<223> OTHER INFORMATION: 2'OMe
<220> FEATURE:
<221> NAME/KEY: modified_base
<222> LOCATION: (2)..(2)
<223> OTHER INFORMATION: 2'F
<220> FEATURE:
<221> NAME/KEY: modified_base
<222> LOCATION: (3)..(3)
<223> OTHER INFORMATION: 2'OMe
<220> FEATURE:
<221> NAME/KEY: modified_base
<222> LOCATION: (4)..(4)
<223> OTHER INFORMATION: 2'F
<220> FEATURE:
<221> NAME/KEY: modified_base
<222> LOCATION: (5)..(5)
<223> OTHER INFORMATION: 2'OMe
<220> FEATURE:
<221> NAME/KEY: modified_base
<222> LOCATION: (6)..(6)
<223> OTHER INFORMATION: 2'F
<220> FEATURE:
<221> NAME/KEY: modified_base
<222> LOCATION: (7)..(7)
<223> OTHER INFORMATION: 2'OMe
```

```
-continued

<220> FEATURE:
<221> NAME/KEY: modified_base
<222> LOCATION: (8)..(8)
<223> OTHER INFORMATION: 2'F
<220> FEATURE:
<221> NAME/KEY: modified_base
<222> LOCATION: (9)..(9)
<223> OTHER INFORMATION: 2'OMe
<220> FEATURE:
<221> NAME/KEY: modified_base
<222> LOCATION: (10)..(10)
<223> OTHER INFORMATION: 2'F
<220> FEATURE:
<221> NAME/KEY: modified_base
<222> LOCATION: (11)..(11)
<223> OTHER INFORMATION: 2'OMe
<220> FEATURE:
<221> NAME/KEY: modified_base
<222> LOCATION: (12)..(12)
<223> OTHER INFORMATION: 2'F
<220> FEATURE:
<221> NAME/KEY: modified_base
<222> LOCATION: (13)..(13)
<223> OTHER INFORMATION: 2'OMe
<220> FEATURE:
<221> NAME/KEY: modified_base
<222> LOCATION: (14)..(14)
<223> OTHER INFORMATION: 2'F
<220> FEATURE:
<221> NAME/KEY: modified_base
<222> LOCATION: (15)..(15)
<223> OTHER INFORMATION: 2'OMe
<220> FEATURE:
<221> NAME/KEY: modified_base
<222> LOCATION: (16)..(16)
<223> OTHER INFORMATION: 2'F
<220> FEATURE:
<221> NAME/KEY: modified_base
<222> LOCATION: (17)..(17)
<223> OTHER INFORMATION: 2'OMe
<220> FEATURE:
<221> NAME/KEY: modified_base
<222> LOCATION: (18)..(18)
<223> OTHER INFORMATION: 2'F
<220> FEATURE:
<221> NAME/KEY: modified_base
<222> LOCATION: (19)..(19)
<223> OTHER INFORMATION: 2'OMe
<220> FEATURE:
<221> NAME/KEY: modified_base
<222> LOCATION: (20)..(20)
<223> OTHER INFORMATION: 2'F

<400> SEQUENCE: 32
ucaaacugug aagccagagu                                                    20

<210> SEQ ID NO 33
<211> LENGTH: 15
<212> TYPE: RNA
<213> ORGANISM: Artificial Sequence
<220> FEATURE:
<223> OTHER INFORMATION: Mock sense strand
<220> FEATURE:
<221> NAME/KEY: modified_base
<222> LOCATION: (1)..(1)
<223> OTHER INFORMATION: 2'F
<220> FEATURE:
<221> NAME/KEY: modified_base
<222> LOCATION: (2)..(2)
<223> OTHER INFORMATION: 2'OMe
<220> FEATURE:
<221> NAME/KEY: modified_base
<222> LOCATION: (3)..(3)
<223> OTHER INFORMATION: 2'F
<220> FEATURE:
<221> NAME/KEY: modified_base
<222> LOCATION: (4)..(4)
```

```
<223> OTHER INFORMATION: 2'OMe
<220> FEATURE:
<221> NAME/KEY: modified_base
<222> LOCATION: (5)..(5)
<223> OTHER INFORMATION: 2'F
<220> FEATURE:
<221> NAME/KEY: modified_base
<222> LOCATION: (6)..(6)
<223> OTHER INFORMATION: 2'OMe
<220> FEATURE:
<221> NAME/KEY: modified_base
<222> LOCATION: (7)..(7)
<223> OTHER INFORMATION: 2'F
<220> FEATURE:
<221> NAME/KEY: modified_base
<222> LOCATION: (8)..(8)
<223> OTHER INFORMATION: 2'OMe
<220> FEATURE:
<221> NAME/KEY: modified_base
<222> LOCATION: (9)..(9)
<223> OTHER INFORMATION: 2'F
<220> FEATURE:
<221> NAME/KEY: modified_base
<222> LOCATION: (10)..(10)
<223> OTHER INFORMATION: 2'OMe
<220> FEATURE:
<221> NAME/KEY: modified_base
<222> LOCATION: (11)..(11)
<223> OTHER INFORMATION: 2'F
<220> FEATURE:
<221> NAME/KEY: modified_base
<222> LOCATION: (12)..(12)
<223> OTHER INFORMATION: 2'OMe
<220> FEATURE:
<221> NAME/KEY: modified_base
<222> LOCATION: (13)..(13)
<223> OTHER INFORMATION: 2'F
<220> FEATURE:
<221> NAME/KEY: modified_base
<222> LOCATION: (14)..(14)
<223> OTHER INFORMATION: 2'OMe
<220> FEATURE:
<221> NAME/KEY: misc_feature
<222> LOCATION: (15)..(15)
<223> OTHER INFORMATION: 3' PC-DCA (Phosphocholine Docosanoic Acid)
<220> FEATURE:
<221> NAME/KEY: modified_base
<222> LOCATION: (15)..(15)
<223> OTHER INFORMATION: 2'F

<400> SEQUENCE: 33
caguaaagag auuaa                                                    15

<210> SEQ ID NO 34
<211> LENGTH: 20
<212> TYPE: RNA
<213> ORGANISM: Artificial Sequence
<220> FEATURE:
<223> OTHER INFORMATION: Mock antisense strand
<220> FEATURE:
<221> NAME/KEY: misc_feature
<222> LOCATION: (1)..(1)
<223> OTHER INFORMATION: 5' VP (Vinylphosphonate)
<220> FEATURE:
<221> NAME/KEY: modified_base
<222> LOCATION: (1)..(1)
<223> OTHER INFORMATION: 2'OMe
<220> FEATURE:
<221> NAME/KEY: modified_base
<222> LOCATION: (2)..(2)
<223> OTHER INFORMATION: 2'F
<220> FEATURE:
<221> NAME/KEY: modified_base
<222> LOCATION: (3)..(3)
<223> OTHER INFORMATION: 2'OMe
<220> FEATURE:
<221> NAME/KEY: modified_base
```

```
<222> LOCATION: (4)..(4)
<223> OTHER INFORMATION: 2'F
<220> FEATURE:
<221> NAME/KEY: modified_base
<222> LOCATION: (5)..(5)
<223> OTHER INFORMATION: 2'OMe
<220> FEATURE:
<221> NAME/KEY: modified_base
<222> LOCATION: (6)..(6)
<223> OTHER INFORMATION: 2'F
<220> FEATURE:
<221> NAME/KEY: modified_base
<222> LOCATION: (7)..(7)
<223> OTHER INFORMATION: 2'OMe
<220> FEATURE:
<221> NAME/KEY: modified_base
<222> LOCATION: (8)..(8)
<223> OTHER INFORMATION: 2'F
<220> FEATURE:
<221> NAME/KEY: modified_base
<222> LOCATION: (9)..(9)
<223> OTHER INFORMATION: 2'OMe
<220> FEATURE:
<221> NAME/KEY: modified_base
<222> LOCATION: (10)..(10)
<223> OTHER INFORMATION: 2'F
<220> FEATURE:
<221> NAME/KEY: modified_base
<222> LOCATION: (11)..(11)
<223> OTHER INFORMATION: 2'OMe
<220> FEATURE:
<221> NAME/KEY: modified_base
<222> LOCATION: (12)..(12)
<223> OTHER INFORMATION: 2'F
<220> FEATURE:
<221> NAME/KEY: modified_base
<222> LOCATION: (13)..(13)
<223> OTHER INFORMATION: 2'OMe
<220> FEATURE:
<221> NAME/KEY: modified_base
<222> LOCATION: (14)..(14)
<223> OTHER INFORMATION: 2'F
<220> FEATURE:
<221> NAME/KEY: modified_base
<222> LOCATION: (15)..(15)
<223> OTHER INFORMATION: 2'OMe
<220> FEATURE:
<221> NAME/KEY: modified_base
<222> LOCATION: (16)..(16)
<223> OTHER INFORMATION: 2'F
<220> FEATURE:
<221> NAME/KEY: modified_base
<222> LOCATION: (17)..(17)
<223> OTHER INFORMATION: 2'OMe
<220> FEATURE:
<221> NAME/KEY: modified_base
<222> LOCATION: (18)..(18)
<223> OTHER INFORMATION: 2'F
<220> FEATURE:
<221> NAME/KEY: modified_base
<222> LOCATION: (19)..(19)
<223> OTHER INFORMATION: 2'OMe
<220> FEATURE:
<221> NAME/KEY: modified_base
<222> LOCATION: (20)..(20)
<223> OTHER INFORMATION: 2'F

<400> SEQUENCE: 34
uuaaucucuu uacugauaua                                                 20

<210> SEQ ID NO 35
<211> LENGTH: 7
<212> TYPE: PRT
<213> ORGANISM: Artificial Sequence
<220> FEATURE:
<223> OTHER INFORMATION: Polypeptide sequence at the N-terminus of AR2
      resulting from the alternative exon 1b
```

```
<400> SEQUENCE: 35

Met Ile Leu Trp Leu His Ser
1               5
```

TREATMENT OF SPINAL AND BULBAR MUSCULAR ATROPHY

CROSS-REFERENCE TO RELATED APPLICATIONS

This application is the National Stage of International Application No. PCT/GB2020/052435, filed Oct. 2, 2020, which claims priority to GB 1914296.7, filed Oct. 3, 2019, which are entirely incorporated herein by reference.

FIELD OF INVENTION

The invention relates to androgen receptor splice variants and treatments of androgen receptor-related disorders.

BACKGROUND OF THE INVENTION

The androgen receptor (AR) is a member of the type I nuclear receptor superfamily, a class of transcription factors that are activated by steroid hormones. The AR, located on the X chromosome, is expressed in a diverse range of tissues, especially the sexual organs in males as well as in motor neurons and muscle cells. The AR signaling pathway plays a key role in the proper development and function of male reproductive organs, such as the prostate and epididymis, as well as musculoskeletal, cardiovascular, immune, neural and haemopoietic systems.

Given the widely varied and important physiological functions of AR, its abnormalities have been identified in various diseases. For example, male sexual differentiation fails to occur in the absence of androgens or a functioning AR. A complete loss of AR function in males results in complete androgen insensitivity syndrome. AR activity is also intimately linked to prostate cancer, which is the most prevalent non-skin cancer in the US, affecting one in every six men and is the second leading cause of cancer-related deaths in males. The polymorphic polyglutamine repeats in the N terminus domain (NTD) of AR, resulting in a toxic gain-of-function AR mutant, has been associated with spinal and Bulbar muscular atrophy (SBMA), also known as Kennedy's Disease, a progressive neurodegenerative condition. There are also an increasing number of studies relating the action of AR to breast, larynx, liver, and testicular cancers.

No disease-modifying treatment is currently available for the AR-related disorders. So far, strategies to treat the AR-related disorders have been ineffective mainly due to severe side-effects and drug resistance. These strategies include androgen deprivation (e.g. chemical castration), gene silencing (e.g. via antisense oligonucleotides or AAV-delivered miRNAs), or modulation of AR function (e.g. by targeting disease-specific post-translational modifications or interaction with cofactors). For example, the clinical trial using an IGF-1 mimetic aimed at increasing phosphorylation and subsequent degradation of AR in SBMA patients has not been successful because of high immunogenicity and failure to improve muscle strength or function (1).

Thus, it is an object of the invention to identify further and improved ways of treating AR-related disorders.

SUMMARY OF THE INVENTION

The inventors discovered that a splice variant of AR, AR2, which occurs naturally in normal tissues, is capable of repressing the activity of AR. The inventors also identified that certain properties of AR2, including the ability to form a heterodimer with AR and being incapable of transactivation on its own, are particularly useful for repressing AR activity. The inventors tested AR2 overexpression in a mouse model representative of an AR-related disease, SBMA. SBMA mice express the human AR transgene with an expanded CAG stretch, encoding for 100 glutamines (AR100Q). When these mice were treated with AR2, they showed improved survival, and increased body weight and locomotor function. Interestingly, the inventors found that male mice harbouring the entire AR gene, and hence endogenously expressing AR2, treated with siRNA targeted to AR2 resulted in a worsening of the neuromuscular phenotype. Therefore, AR variants that are capable of forming a heterodimer with AR and incapable of transactivation on its own, such as AR2, are useful therapeutics for AR-related disorders.

Whilst not wishing to be bound by theory, the inventors speculate that, in normal cells, AR2 may act as a decoy by forming heterocomplexes with AR, thereby acting as a transcriptional repressor repressing the activity of AR, possibly at the level of the androgen response elements (ARE) of the target genes. Thus, AR2 may act to fine-tune AR activity thereby restoring the homeostatic state of AR activity in normal cells.

For disorders that are associated with increased AR activity, such as those caused by toxic gain-of-function AR mutants, AR2 may act to repress the activity of the disorder-associated AR mutants. In these disorders, therefore, an enhanced activity of AR2, e.g. by gene delivery techniques, may be beneficial.

For disorders associated with decreased AR activity, inhibiting the expression of endogenously expressed AR2, e.g. by gene silencing techniques, may be beneficial.

The therapeutic strategies based on AR2 are superior to the current strategies for treating AR-related disorders because the current strategies often involve changing the AR protein level (e.g. antisense oligonucleotides targeted to AR) or hormone levels (e.g. chemical castration), or targeting post-translational modification machineries or co-factors, all of which are either disrupting the genomic and non-genomic activity of AR or are not specific to AR and therefore are typically associated with undesirable side-effects. Furthermore, these strategies are often hampered by the potential of exacerbation of signs and symptoms related to the loss of androgen function, especially since most of the affected patients are males, who only have one copy of the AR gene. In contrast, the invention relates to treatments based on the naturally occurring AR2, and so these AR variants mimic the natural activity of AR to a certain degree, for example, they would be regulated in a similar way and have similar target genes. Thus, the AR2-based therapeutics according to the invention are able to modulate the activity of AR with minimal disturbance to the intricate network that regulates AR, its transcriptional output and signalling pathways.

Accordingly, an aspect of the invention provides an expression construct encoding an AR variant for use in a method for treatment of the human or animal body by therapy, the AR variant comprises a polypeptide sequence having ≥70% (i.e. 70% or more), ≥80%, ≥90%, ≥95% ≥99% or 100% identity with the androgen receptor splice variant 2 (AR2).

The invention also provides a host cell comprising or producing an expression construct for use in a method for treatment of the human or animal body by therapy, wherein the expression construct encodes an AR variant, wherein the AR variant comprises a polypeptide sequence having ≥70%, ≥80%, ≥90%, ≥95% ≥99% or 100% identity with AR2.

The invention also provides a pharmaceutical composition for use in a method for treatment of the human or animal body by therapy, wherein the pharmaceutical composition comprises a pharmaceutically acceptable carrier and: (a) an expression construct encoding an AR variant for use in a method for treatment of the human or animal body by therapy, wherein the AR variant comprises a polypeptide sequence having ≥70%, ≥80%, ≥90%, ≥95% ≥99% or 100% identity with AR2, or (b) a host cell comprising or producing the expression construct.

The invention also provides a method of treating an AR-related disorder in a patient in need thereof, comprising administering a therapeutically effective amount of: (a) an expression construct encoding an AR variant for use in a method for treatment of the human or animal body by therapy, wherein the AR variant comprises a polypeptide sequence having ≥70%, ≥80%, ≥90%, ≥95% ≥99% or 100% identity with AR2, (b) a host cell comprising or producing the expression construct, and/or (c) a pharmaceutical composition comprising (a) or (b) and a pharmaceutically acceptable carrier.

In another aspect, the invention provides an agent capable of modulating (e.g. inhibiting) the expression and/or activity of AR2. The invention also provides a pharmaceutical composition comprising the agent. The invention also provides the agent or the pharmaceutical composition for use in a method for treating an AR-related disorder. The invention also provides a method for treating an AR-related disorder in a patient in need thereof, comprising administering to the patient an effective amount of the agent or the pharmaceutical composition.

In a further aspect, the invention provides an AR variant comprising a polypeptide sequence having ≥70%, ≥80%, ≥90%, ≥95% ≥99% or 100% identity with SEQ ID NO: 1; wherein the AR variant is capable of forming a heterodimer with AR, the AR variant alone is incapable of transactivation, and the AR variant is not SEQ ID NO: 3. The invention also provides an expression construct encoding the AR variant, and a host cell comprising or producing the expression construct. The invention also provides a pharmaceutical composition comprising the expression construct or the host cell. The invention also provides the AR variant, expression construct, the host cell or the pharmaceutical composition for use in a method for treating an AR-related disorder. The invention also provides a method for treating an AR-related disorder in a patient in need thereof, comprising administering to the patient a therapeutically effective amount of the AR variant, expression construct, the host cell or the pharmaceutical composition. The invention further provides the use of the AR variant, expression construct, the host cell or the pharmaceutical composition in the manufacture of a medicament in a method of treating an AR-related disorder.

BRIEF DESCRIPTION OF THE SEQUENCES

SEQ ID NO: 1 shows the polypeptide sequence of an AR variant.
SEQ ID NO: 2 shows the polynucleotide sequence encoding the AR variant of SEQ ID NO: 1.
SEQ ID NO: 3 shows the polypeptide sequence of human AR2.
SEQ ID NO: 4 shows the cDNA sequence of human AR2.
SEQ ID NO: 5 shows the polypeptide sequence of the NTD of human AR.
SEQ ID NO: 6 shows the polypeptide sequence of human AR.
SEQ ID NO: 7 shows the polypeptide sequence of an AR variant.
SEQ ID NO: 8 shows the polypeptide sequence of an AR variant.
SEQ ID NOs: 9-34 shows the siRNA sequences (sense and antisense) used in the examples.
SEQ ID NO: 35 shows the polypeptide sequence at the N-terminus of AR2 resulting from the alternative exon 1b.

DETAILED DESCRIPTION OF THE INVENTION

AR Variants

The invention relates to AR variants, in particular the splice variant 2 of AR (AR2). AR2 from any animals may be used with the invention, in particular, human AR2 (ENST00000396043, ENSP00000379358). The polypeptide sequence of human AR2 is provided in SEQ ID NO: 3 and the corresponding cDNA is provided in SEQ ID NO: 4.

Figure 1A:
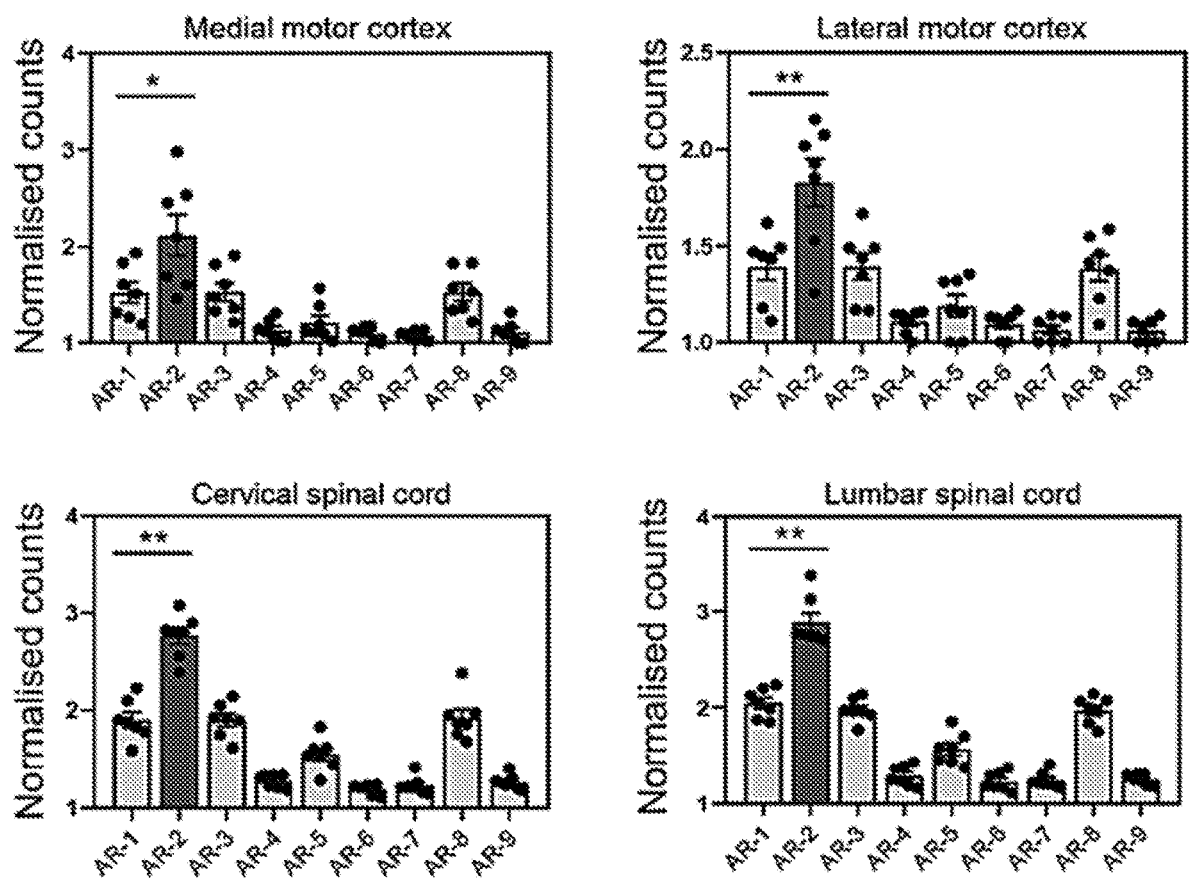
FIG. 1 shows that AR2 is highly expressed in human tissues. a) RNA-seq of human brain tissues using the Illumina HiSeq 4000 platform. AR splice variants expression levels from the indicated human brain tissues are shown. Expression values are represented as log-normalised counts. Data are mean±s.e.m. Each dot represents one replicate (n=7). *P<0.05; **P<0.01. b) Heatmap indicating relative AR2 levels in 38 different human tissues. c) Relative mRNA expression levels of AR2 compared to AR1 in human myoblasts. Data are mean±s.e.m. Each dot represents one replicate (n=6). d) Schematic representation of different human mRNA AR splice variants is shown. Empty and full squares represents the UTRs and exons, respectively. e) ChIP-qPCR on exon 1b of AR gene as compared to a downstream sequence on intron 1 showing increased RNA Pol II occupancy. Data are mean±s.e.m. Each dot represents one replicate (n=3). f) Inclusion of the alternative exon 1b results in different N-terminal amino acid sequence (NTD) in AR2 (MILWLHS; SEQ ID NO: 35) compared to AR1. AR1 and AR2 share the same remaining sequence (left). AR1 and AR2 splice variants were expressed in HEK293T cells. Whole cell extracts were resolved by SDS PAGE followed by immunoblotting by using a C-terminal AR antibody. Molecular size is indicated (right).

AR2 is one of nine naturally occurring splice variants in normal tissues. AR2 was originally identified via rapid amplification of cDNA ends (RACE) with RNA isolated from human placenta tissue (17). AR2 mRNA was found to arise from inclusion of an alternative exon 1 (exon 1b) situated 22.1 kb downstream of exon 1 (FIG. 1d). The encoded protein contains a unique N-terminal sequence in place of the canonical NTD and has a molecular mass of 45 kDa, hence AR2 is also known in the literature as AR45 (FIG. 1f). However, to date very little is known about its function. The inventors have now identified AR2 as the most highly expressed splice variant in healthy human brain tissues, motor neurons and skeletal muscles. The inventors also showed beneficial effects of SBMA mice treated with AR2 overexpression, and worsening effects of SBMA mice treated with AR2 knock down.

The invention also refers to sequence variants. These variants include polypeptides having ≥70% (i.e. 70% or more), ≥75%, ≥80%, ≥85%, ≥90%, ≥95% or 99% sequence identity to AR2, e.g. human AR2 (SEQ ID NO: 3).

Further AR variants useful with the invention may comprise a polypeptide sequence having ≥70% (i.e. 70% or greater) identity with SEQ ID NO: 1. For example, the AR variant may comprise or consist of a polypeptide sequence having ≥80%, ≥90%, ≥95% ≥99% or 100% identity with SEQ ID NO: 1. In some embodiments of the invention, the AR variant is not AR2, e.g. the AR variant is not SEQ ID NO: 3.

The cDNA corresponding to SEQ ID NO: 1 is provided in SEQ ID NO: 2. The AR variant may comprise or consist of a polynucleotide sequence having ≥80%, ≥90%, ≥95% or ≥99% identity with SEQ ID NO: 2.

SEQ ID NO: 1 corresponds to amino acids 556-920 of SEQ ID NO: 6. SEQ ID NO: 6 is the polypeptide sequence of human androgen receptor (AR; ENST00000374690), also referred to as AR1 herein. Human AR is composed of three main domains: (i) exon 1 encodes the highly variable amino-terminal domain (NTD) (amino acids 1-555; provided as SEQ ID NO: 5), with potent transcriptional activator capability, (ii) exons 2 and 3 encode a central two zinc finger motifs DNA-binding domain (DBD) and the hinge region (amino acids 556-670), and (iii) exons 4-8 encode a well-conserved carboxy-terminal ligand-binding domain (LBD; amino acids 671-920) responsible for interacting with the transcriptional machinery.

An AR variant according to the invention is capable of forming a heterodimer with AR. Whilst not wishing to be bound by theory, the AR variants according to the invention may act as a decoy by forming heterocomplexes with the disease-associated AR mutants, thereby modulating the activity of the disease-associated AR mutants, possibly at the level of the androgen response elements (ARE) of the target genes. In the AR, dimerization is mediated mainly through N/C-terminal interactions via the FXXLF motif and DBD/DBD interactions via the dimerization box (D-box). Thus, an AR variant according to the invention may contain the DBD and LBD domains of AR, i.e. SEQ ID NO: 1, which corresponds to amino acids 556-920 of SEQ ID NO: 6.

Methods to determine whether AR dimerization are known in the art and described in the examples herein, e.g. bioluminescence resonance energy transfer (BRET) assays which allows real-time detection of complex formation, or co-immunoprecipitation assays.

An AR variant according to the invention is incapable of transactivation alone, even in presence of the ligand. A region having transactivation function is the activating function 1 (AF-1) subdomain in the NTD of AR, which spans amino acids 51-211. Thus, an AR variant according to the invention may partially lack the NTD, such as lacking the AF-1 subdomain. For example, an AR variant according to the invention may be SEQ ID NO: 7, which lacks amino acids 51-211 of SEQ ID NO: 6. An AR variant according to the invention may be SEQ ID NO: 8, which lacks amino acids 1-211 of SEQ ID NO: 6. In other embodiments, the AR variant may lack the entire NTD, e.g. the AR variant does not comprise SEQ ID NO: 5.

An AR variant may be encoded by a mRNA partially lacking the canonical exon 1. The AR variant may be encoded by a mRNA that lacks the entire canonical exon 1 of AR.

Methods to determine whether a AR variant is capable of activating transcription alone are known in the art and described in the examples herein, e.g. in vitro reporter expression assays such as luciferase assay.

Furthermore, the NTD contains the polyglutamine tract (5-36 residues) (amino acids 59-89 of SEQ ID NO: 6) and the size of this polyglutamine tract affects AR function, with longer tracts associated with lower AR activity. For example, expansion of this polyglutamine tract (e.g. 38-68 residues) causes SBMA. Thus, an AR variant according to the invention may lack the region corresponding to the polyglutamine tract.

An AR variant according to the invention may contain modifications relative to any of SEQ ID NOs: 1, 3, 7 and 8, such as amino acid substitutions, additions or deletions. For example, the AR variant may comprise 1, 2, 3, 4, 5, 6, 7, 8, 9, 10 or more amino acid residues that are substituted, deleted or added, in any combination.

For example, the variants may have additions, deletions or substitutions of amino acid residues which do not substantially alter the biological activity of AR2. Those individual sites or regions of AR2, which can be altered without affecting biological activity can be determined by examination of the structure of the AR2 domains, for example. Alternatively, the regions which would tolerate amino acid substitutions may be determined by alanine scanning mutagenesis (2). In this method, selected amino acid residues are individually substituted with a neutral amino acid (e.g. alanine) in order to determine the effects on biological activity.

An AR variant may contain conservative amino acid changes which are least likely to perturb the structure and/or function of a polypeptide. For example, the variant may comprise one or more conservative amino acid changes within any of SEQ ID NOs: 1, 3, 7 and 8. Conservative amino acid changes generally involve substitution of one amino acid with another that is similar in structure and/or function (e.g. amino acids with side chains similar in size, charge and shape). Amino acid residues having similar side chains are known in the art. These include amino acids with basic side, chains (e.g. lysine, arginine, histidine), acidic side chains (e.g. aspartic acid, glutamic acid), uncharged polar side chains (e.g. glycine, asparagine, glutamine, serine, threonine, tyrosine, cysteine, tryptophan), nonpolar side chains (e.g. alanine, valine, leucine, isoleucine, proline, phenylalanine, methionine), beta-branched side chains (e.g. threonine, valine, isoleucine) and aromatic side chains (e.g. tyrosine, phenylalanine, tryptophan, histidine). Thus, one or more amino acid residue within AR2 can be replaced with other amino acid residues having similar side chains and the altered protein can be tested for retained function using the functional assays described herein. Modifications can be introduced by standard techniques known in the art, such as site-specific mutagenesis (3) and PCR-mediated mutagenesis, provided that activity, e.g., the ability to form heterodimerisation with AR, is retained.

An AR variant may be codon optimized to increase expression levels of the respective protein in host cells as compared to if the unaltered sequence. Methods for codon optimisation are known in the art, e.g. GeneScript OptimumGene™ algorithm can be used.

The invention refers to a polynucleotide encoding AR2, e.g. human AR2 (SEQ ID NO: 4). The invention also refers to polynucleotide encoding AR variants. The polynucleotide may differ from the polynucleotide sequence shown in SEQ ID NO: 4 due to degeneracy of the genetic code and thus encode the same protein as that encoded by the polynucleotide sequence shown in SEQ ID NO: 4.

For example, the polynucleotide may have ≥70% (i.e. 70% or more), ≥75%, ≥80%, ≥85%, ≥90%, ≥95% or 100% sequence identity to SEQ ID NO: 4.

The polynucleotide may encode any AR variant protein described herein.

Expression Constructs

The invention further provides expression constructs encoding AR variants according to the invention for use in therapy. Any expression constructs suitable to be expressed in humans and animals can be used with the invention. For example, the expression construct may be a non-viral plasmid-based vector or a viral vector.

The viral vector may be one derived from adenoviruses, adeno-associated viruses (AAV), or retroviruses, including lentiviruses such as the human immunodeficiency (HIV) virus. The expression construct may be prepared by standard means known in the art for provision of expression constructs for gene therapy. Thus, well established public domain transfection and/or transduction, packaging and purification methods can be used to prepare a suitable vector preparations, and suitable viral particles.

The expression construct may also comprise regulatory sequences allowing expression and, preferably, secretion of the encoded protein, such as e.g., a promoter, enhancer, polyadenylation signal, internal ribosome entry sites (IRES), sequences encoding protein transduction domains (PTD).

The expression construct may comprise a polynucleotide comprising a promoter region, operably linked to AR2, to cause or improve expression of the therapeutic protein in infected host cells. The promoter may be ubiquitous, tissue-specific, strong, weak, regulated or chimeric. The promoter is typically selected to allow efficient and suitable production of the protein in the infected tissue. The promoter may be of mammalian (e.g. human or murine) origin, or of other origin, including cellular, viral, fungal, plant or synthetic promoters. The promoter may be functional in nervous cells, e.g. motor cells, and muscle cells, particularly in human cells.

Examples of a regulated promoter useful with the invention include Tet on/off element-containing promoters, rapamycin-inducible promoters and metallothionein promoters.

The promoter may be tissue-specific, such as a muscle-specific promoter. A muscle-specific promoter useful with the invention may be the mammalian muscle creatine kinase (MCK) promoter, the mammalian desmin (DES), or an artificial promoter based on MCK (e.g. enh358MCK, see reference 4) or DES.

Another tissue-specific promoter useful with the invention may be a motor neuron-specific promoter. Examples of promoters specific for the motor neurons include the promoter of the Choline Acetyl Transferase (ChAT). Other promoters functional in motor neurons include the promoters of the Calcitonin Gene-Related Peptide (CGRP) (a known motor neuron-derived factor), Neuron Specific Enolase (NSE), Synapsin, or ubiquitous promoters including Neuron Specific Silencer Elements (NRSE).

Alternatively, the promoter may be a constitutively active promoter selected from the group consisting of the cytomegalovirus (CMV) promoter, the phosphoglycerate kinase (PGK) promoter, the simian virus 40 (SV40) promoter, the Ubiquitin C (UbC) promoter, the CAG promoter, the ubiquitous chromatin opening element (UCOE) promoter, the CD11b promoter, the Wiskott-Aldrich syndrome (WAS) promoter and the Glyceraldehyde 3-phosphate dehydrogenase (GAPDH) promoter.

An expression construct useful with the invention comprises the enh358MCK promoter. The enh358MCK promoter is known in the art is constructed by ligating the ~200 bp enhancer with the 358 bp proximal promoter of the murine MCK gene. Thus, the AR variant according to the invention is expressed from the enh358MCK promoter.

An expression construct useful with the invention comprises the Choline Acetyl Transferase (ChAT). Thus, the AR variant according to the invention is expressed from the ChAT promoter.

Gene Delivery

AR variants, polynucleotides and expression constructs described herein may be administered to treat AR2-related disorders by way of gene therapy, such that the expression construct produces its encoded protein for mediating a therapeutic effect in the host.

Any of the methods for gene therapy available in the art can be used, e.g. those reviewed in references 5, 6, 7, 8, 9 and 10. Methods involving recombinant DNA technology are known in the art (11,12).

An in vivo gene therapy approach may be used with the invention. Hence, the treatment according to the invention may include a step of delivering the expression construct directly into a patient or cell. Hence, the expression construct may be directly administered in vivo, where it is expressed to produce the encoded product. This can be accomplished by any of numerous methods known in the art, e.g., by infection using defective or attenuated retrovirals or other viral vectors, or by direct injection of naked DNA, or by use of microparticle bombardment (e.g. a gene gun; Biolistic, Dupont), or coating with lipids or cell-surface receptors or transfecting agents, encapsulation in liposomes, microparticles, microcapsules, nanoparticles, or nanocapsules, or by administering them in linkage to a peptide which is known to enter the nucleus, by administering it in linkage to a ligand subject to receptor-mediated endocytosis, e.g. see reference 13, which can be used to target cell types specifically expressing the receptors. In addition, the expression construct can be targeted in vivo for cell specific uptake and expression, by targeting a specific receptor, e.g. see reference14. In certain embodiments, the expression construct may be introduced intracellularly and incorporated within host cell DNA for expression, by homologous recombination, e.g. see references 15 and 16.

An ex vivo gene therapy approach may be used with the invention. Hence, the treatment according to the invention may include transforming host cells with the expression constructs in vitro, followed by transplantation of the host cells into the patient. Methods of introducing expression constructs to cells in tissue culture are well known in the art, including transfection, electroporation, microinjection, infection with a viral or bacteriophage vector containing the nucleic acid sequences, cell fusion, chromosome-mediated gene transfer, microcell-mediated gene transfer, spheropiast fusion. The technique typically provides for the stable transfer of the expression construct to the host cell, so that the expression construct is expressible by the host cell and can be heritable and expressible by its cell progeny. The method of introducing expression constructs may further include introducing a selectable marker to the host cells, and placing the host cells under selection, and isolating the host cells that have taken up and are expressing the transferred gene. The resulting recombinant cells can be delivered to a patient by various methods known in the art.

The invention also provides host cells comprising or producing the expression constructs according to the invention. Host cells into which an expression construct can be introduced for purposes of gene therapy encompass any desired, available cell type. For example, stem or progenitor cells can be used. Any stem and/or progenitor cells which can be isolated and maintained in vitro can potentially be used, e.g. such as those described in references 17, 18, 19, 20. For example, in the case where the host cells are blood cells, the recombinant blood cells (e.g. hematopoietic stem or progenitor cells) may be administered intravenously. The amount of host cells for use depends on various factors, such as the desired effect and the patient state, and can be routinely determined by one skilled in the art.

Modulation of AR2 Activity

The invention involves using agents that are capable of modulating the activity of AR2. The agent may be an agent which downregulates the transcriptional level and/or protein level of AR2, an agent which modulate the interaction between AR2 with their co-factors, such as coactivator proteins or DNA response elements, and agents which modulate posttranslational modification of AR2.

The agent may be capable of specifically modulating AR2 activity, without affecting the activity of AR and the other endogenously expressed splice variants of AR. The agent may have ≥50% (i.e. 50% or more), ≥60%, ≥70%, ≥80%, ≥90% or 100% selectivity for AR2 compared to AR or any of the other endogenously expressed splice variants of AR, i.e. AR1, AR3, AR4, AR5, AR6, AR7, AR8 or AR9.

The agent may be an inhibitor of transcription of AR2, an inhibitor of translation of AR2, or an antagonist of AR2. The agent may inhibit expression of the AR2 mRNA. For example, it may be antisense oligonucleotide, RNA interference oligonucleotide (RNAi), ribozyme, an agent that degrades transcription factors required for AR2 transcription, or an antibody that binds to AR2. For example, the agent may reduce the level of mRNA expression of AR2 by ≥50% (i.e. 50% or more), ≥60%, ≥70%, ≥80% ≥90% or 100% compared to when the agent is not administered.

The agent may inhibit the function of AR2. For example, the activity of AR2 may be reduced by ≥50% (i.e. 50% or more), ≥60%, ≥70%, ≥80% ≥90% or 100% compared to when the agent is not administered.

RNAi techniques may be used to knock down AR2 in cells. For example, the agent may be in the form of dsRNA (double stranded RNA) or shRNA (short hairpin RNA) molecules which are digested in vivo to 21-23 nt fragment small interfering RNAs (siRNAs) that mediate the RNAi effect. The siRNA may be encoded by nucleotide sequences within polynucleotide sequences of AR2 (e.g. SEQ ID NO:4). The siRNA may be about 20-50 nucleotides in length, e.g. about 21-23 nucleotides in length. The siRNA may have ≥70% (i.e. 70% or more), ≥80%, ≥90%, ≥95%, ≥99% or 100% sequence identity to AR2 (e.g. SEQ ID NO: 4). For example, the siRNA may comprises the sequences listed in any of SEQ ID NOs: 9-32. The siRNA may comprise the sequences listed SEQ ID NOs: 31 and 32.

The siRNA may be composed of conventional nucleotides A, G, T, C, or U, or unusual or modified nucleotides such as inosinic acid, 1-methyl inosinic acid, 1-methyl guanylic acid, NN-dimethyl guanylic acid, pseudouridylic acid, ribothymidylic acid, 5-hydroxymethylcytosine, and 5-hydroxymethyluridine.

The siRNAs or vectors encoding the same may be delivered to cells by techniques known in the art, such as in vivo or ex vivo gene therapy approaches as described above. The siRNAs may be prepared by any methods that are known in the art, including, but not limited to, oligonucleotide synthesis, in vitro transcription, ribonuclease digestion, or generation of siRNAs in vivo.

Antisense techniques may also be used according to the invention. An antisense oligonucleotide useful according to the invention may be RNA or DNA that is complementary to AR2 (e.g. SEQ ID NO: 4) and is capable of hybridising to and inhibiting the expression of AR2. The antisense oligonucleotide may have ≥70% (i.e. 70% or more), ≥80%, ≥90%, ≥95%, ≥99% or 100% complementarity to AR2. The antisense oligonucleotide may be 15 to 30 bp in length. Other criteria that are known in the art may be used to select the antisense oligonucleotides, varying the length or the annealing position in the targeted sequence. The antisense oligonucleotide may include derivatives such as S-oligonucleotides (phosphorothioate derivatives or S-oligos). The antisense oligonucleotide is coadministered with an agent which enhances the uptake of the antisense molecule by the cells, e.g. a lipophilic cationic compound which may be in the form of liposomes. The antisense oligonucleotide may be combined with a lipophilic carrier such as sterols, e.g. cholesterol, cholate and deoxycholic acid. The antisense oligonucleotide may be conjugated to a peptide that is ingested by cells, e.g. peptide hormones, antigens or antibodies or peptide toxins.

Ribozymes may also be useful in the invention. For example, antisense RNA/ribozyme fusions which comprise antisense RNA targeted to AR2 and a ribozyme which cleaves RNA can be used. The ribozyme molecule may be based upon the chloramphenicol acetyltransferase ribozyme or hairpin ribozymes.

Treatment and Medical Uses

The invention further relates to the AR variants, expression constructs, host cells, AR2 modulation agents, or pharmaceutical compositions described herein for use in a method for treatment of the human or animal body by therapy. The invention further relates to the use of the AR variants, expression constructs, host cells, AR2 modulation agents, or pharmaceutical compositions described herein in a method for treatment of the human or animal body by therapy. The invention further relates to the use of the AR variants, expression constructs, host cells, AR2 modulation agents, or pharmaceutical compositions described herein in the manufacture of a medicament for a method for treatment of the human or animal body by therapy. The invention also relates to methods of treatments using the AR variants, expression constructs, host cells, AR2 modulation agents, or pharmaceutical compositions described herein.

In particular, the invention relates to methods of treating AR-related disorders. For example, the methods and uses of the invention may comprise inhibiting the disease state, e.g. arresting its development; and/or relieving the disease state, e.g. causing regression of the disease-state until a desired endpoint is reached. The methods and uses of the invention may comprise the amelioration of a symptom of the AR-related disorder (e.g. lessen the pain or discomfort), and such amelioration may or may not be directly affecting the disease. The methods and uses of the invention may comprise preventing the AR-disorder from occurring in a mammal (e.g. humans), in particular, when such mammal is predisposed to the AR-disorder but has not yet been diagnosed as having it. The methods and uses of the invention may comprise restoring AR activity and/or AR signalling in patients to normal levels for a healthy subject.

An AR disorder is a disorder that is associated with aberrant activity of AR. The disorder may be caused in part or exacerbated by increased AR activity, e.g. as a result of a toxic-gain-of-function AR mutant (e.g. in SMBA). For example, the AR activity in these disorders may be increased by ≥50% (i.e. 50% or more), ≥60%, ≥70%, ≥80%, ≥90%, ≥100% or ≥200% compared to the AR activity in healthy subjects. In this case, repressing AR activity by AR variants described herein may be beneficial.

The disorder may be caused in part or exacerbated by decreased AR activity, e.g. as a result of a loss-of-function AR mutant (e.g. in androgen-insensitivity syndrome). For example, the AR activity in these disorders may be decreased by ≥50% (i.e. 50% or more), ≥60%, ≥70%, ≥80%, ≥90% or ≥100% compared to the AR activity in healthy subjects. In this case, increasing AR activity by alleviating its repression, e.g. by inhibiting AR2 expression using the AR2 modulating agents described herein, may be beneficial.

The methods and uses of the invention may include a step of determining the expression and/or activity levels of AR and disorder-associated AR mutants in a sample from the patient. Methods of determining the expression and/or activity levels of AR and disorder-associated AR mutants are known in the art and exemplified in the Examples described herein (e.g. see FIGS. 2a and 2b). For example, the level of AR expression may be assayed by detecting and measuring AR transcription. AR transactivation activity can be measured by reporter assays, such as luciferase assays, which involves transfecting into the cells a reporter vector with an insertion of an androgen responsive element (ARE) upstream of the reporter gene, followed by measuring the expression level or the reporter gene. RNA from a sample may be isolated and tested by hybridisation or PCR techniques as known in the art. Alternatively, AR2 expression assays can be performed in situ, i.e. directly upon tissue sections (fixed and/or frozen) of patient tissue obtained from biopsies or resections, such that no nuclei acid purification is necessary Immunoassays may also be used.

The methods and uses of the invention may include a step of identifying patients that have an AR-related disorder. Methods for identifying patients that have an AR-related disorder are known in the art. For example, clinical testing of repeat numbers (e.g. CAG polyglutamine and/or GGN polyglycine repeats) or mutations in the AR gene can be carried out. It has been shown that a short CAG repeat causes increase AR transactivation (e.g. in benign prostatic hyperplasia), whereas a longer CAG stretch results in reduced activity (e.g. in SBMA). Furthermore, their effects in altering AR transcriptional activity has been considered to cumulatively contribute to cancer risk and age of diagnosis, e.g. in prostate cancer.

The patient may be male or female. The patient is typically male.

The patient may be suffering from the AR-related disorder or may be at risk of an AR-related disorder. The patient may be identified as being at risk of, or having, an AR-related disorder. The patient may be asymptomatic. The patient may have a predisposition to the AR-related disorder. The method or use may comprise a step of identifying whether or not a patient is at risk of developing, or has an AR-related disorder.

Examples of the AR-related disorders include SBMA, androgen-insensitivity syndrome, bone and/or metabolic conditions, prostate cancer, androgen deficiency, hypogonadism, benign prostatic hyperplasia (BPH). AR-related disorders are known in the art, e.g. reviewed in Davey and Grossmann (21) and Shukla et al (22).

Spinal Bulbar Muscular Atrophy

The invention relates to treating spinal and bulbar muscular atrophy (SBMA).

Spinal and bulbar muscular atrophy, also known as Kennedy's disease, is an X-linked disease caused by CAG repeat expansions in the AR gene, characterized by motor neuron degeneration and primary muscle atrophy. The degenerating motor neurons are located primarily at the anterior horns of the spinal cord and in the bulbar region. The polymorphic CAG repeat usually consists of 9-36 repeats; expansion beyond 40 repeats causes neurotoxicity. SBMA only affects males, its prevalence is 1/50:000.

In SBMA patients, neuromuscular symptoms generally first appear as muscle spasms and weakness in the extremities, mouth, and throat, which progress to muscle wasting due to loss of motor neurons. There is currently no known cure for SBMA, and treatment is symptomatic, usually entailing physical therapy and rehabilitation. Patients with SBMA frequently become confined to a wheelchair later in life and require assistance with common daily tasks, such as eating. AR silencing has long been sought after as an attractive therapeutic strategy, although it is hampered by the direct and indirect effects associated with AR loss of function.

Methods and uses of the invention may include alleviating one or more symptoms associated with SBMA, including preventing, delaying or reducing: loss of muscle mass, loss of mobility, and loss of physical strength. The invention may also relate to reversing the signs of androgen insensitivity in the subject.

For SBMA, repressing AR activity by AR variants described herein may be beneficial. Thus, the invention provides AR variants, expression constructs, host cells and pharmaceutical compositions described herein for use in a method for treatment of SBMA. The invention further provides the use of AR variants, expression constructs, host cells and pharmaceutical compositions described herein in a method for treatment of SBMA. The invention further provides the use of AR variants, expression constructs, host cells and pharmaceutical compositions described herein in the manufacture of a medicament for a method for treatment of SBMA. The invention also provides a method for treatment of SBMA using the AR variants, expression constructs, host cells and pharmaceutical compositions described herein.

Androgen Insensitivity Syndrome

The invention relates to treating androgen-insensitivity syndrome, such as complete (CAIS) or partial (PAIS) androgen insensitivity.

Missense and nonsense mutations in the AR gene resulting in loss-of-function AR mutants cause a wide spectrum of abnormalities in male development. Such abnormalities range from mild virilisation defects to complete male-to-female phenotypic sex reversal; these mutations lead to either complete (CAIS) or partial (PAIS) androgen insensitivity.

For AIS, increasing AR activity by alleviating its repression, e.g. by inhibiting AR2 expression using the AR2 modulating agents or pharmaceutical compositions comprising AR2 modulating agents, as described herein, may be beneficial. Thus, the invention provides AR2 modulating agents and pharmaceutical compositions comprising AR2 modulating agents, as described herein, for use in a method for treatment of AIS. The invention further provides the use of AR2 modulating agents and pharmaceutical compositions comprising AR2 modulating agents, as described herein, in a method for treatment of AIS. The invention further provides the use of AR2 modulating agents and pharmaceutical compositions comprising AR2 modulating agents, as described herein, in the manufacture of a medicament for a method for treatment of AIS. The invention also provides a method for treatment of AIS using AR2 modulating agents and pharmaceutical compositions comprising AR2 modulating agents, as described herein.

Bone/Metabolic Conditions

The invention relates to treating bone or metabolic conditions and typically these conditions are caused in part or exacerbated by decreased AR activity, e.g. caused by loss-of-function AR mutants.

Bone or metabolic conditions useful with the invention include osteoporosis (such as age-related osteoporosis), osteopenia, glucocorticoid-induced osteoporosis, periodontal disease, HIN-wasting, cancer cachexia, bone fracture, bone damage following bone reconstructive surgery, muscular dystrophies, sarcopenia, frailty (e.g. decreased bone mass, reduced muscle mass, and lower strength.), aging skin, male hypogonadism, post-menopausal symptoms in women, female sexual dysfunction, premature ovarian failure, autoimmune disease, atherosclerosis, hypercholesterolemia, hyperlipidemia, aplastic anaemia and other hematopoietic disorders, arthritis and joint repair.

For these bone or metabolic conditions, increasing AR activity by alleviating its repression, e.g. by inhibiting AR2 expression using the AR2 modulating agents or pharmaceutical compositions comprising AR2 modulating agents, as described herein, may be beneficial. Thus, the invention provides AR2 modulating agents and pharmaceutical compositions comprising AR2 modulating agents, as described herein, for use in a method for treatment of a bone or metabolic condition. The invention further provides the use of AR2 modulating agents and pharmaceutical compositions comprising AR2 modulating agents, as described herein, in a method for treatment of a bone or metabolic condition. The invention further provides the use of AR2 modulating agents and pharmaceutical compositions comprising AR2 modulating agents, as described herein, in the manufacture of a medicament for a method for treatment of a bone or metabolic condition. The invention also provides a method for treatment of a bone or metabolic condition using AR2 modulating agents and pharmaceutical compositions comprising AR2 modulating agents, as described herein.

Prostate Cancer

The invention relates to treating prostate cancer.

Prostate development and prostate cancer are critically dependent on androgen signalling. In fact, androgen deprivation therapy remains the most widely used treatment for patients with advanced prostate cancer. However, although androgen deprivation initially results in prostate tumour regression, the tumours eventually re-emerge, and the resulting hormone-refractory (androgen independent) state is invariably fatal. Even after acquiring castration resistance, prostate tumours rely on AR signalling.

Methods of assessing tumour regression are known in the art. For example, the level of prostate specific antigen (PSA) increases with progression of prostate cancer. Thus, the invention may include a step of determining PSA levels in the patients to evaluate the regression of prostate cancer in a patient.

The invention provides AR variants, expression constructs, host cells, AR2 modulating agents and pharmaceutical compositions described herein for use in a method for treatment of prostate cancer. The invention further provides the use of AR variants, expression constructs, host cells, AR2 modulating agents and pharmaceutical compositions described herein in a method for treatment of prostate cancer. The invention further provides the use of AR variants, expression constructs, host cells AR2 modulating agents and pharmaceutical compositions described herein in the manufacture of a medicament for a method for treatment of prostate cancer. The invention also provides a method for treatment of prostate cancer using the AR variants, expression constructs, host cells AR2 modulating agents and pharmaceutical compositions described herein.

Pharmaceutical Compositions and Dosages

The invention also provides a pharmaceutical composition comprising a AR variant, a polynucleotide, an expression construct, a host cell or a AR2 modulation agent described herein. A pharmaceutical composition of the invention may comprise a pharmaceutically acceptable excipient, carrier, buffer, stabiliser or other materials well known to those skilled in the art. Such materials are typically non-toxic and does not interfere with the efficacy of the active ingredient. The precise nature of the carrier or other material may be determined by the skilled person according to the route of administration.

The pharmaceutical composition is typically in liquid form. Liquid pharmaceutical compositions generally include a liquid carrier such as water, petroleum, animal or vegetable oils, mineral oil or synthetic oil. Physiological saline solution, magnesium chloride, dextrose or other saccharide solution or glycols such as ethylene glycol, propylene glycol or polyethylene glycol may be included. In some cases, a surfactant, such as pluronic acid (PF68) 0.001% may be used.

For injection at the site of affliction, the active ingredient will be in the form of an aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection, Hartmann's solution. Preservatives, stabilisers, buffers, antioxidants and/or other additives may be included, as required.

For delayed release, a vector may be included in a pharmaceutical composition which is formulated for slow release, such as in microcapsules formed from biocompatible polymers or in liposomal carrier systems according to methods known in the art.

Dosages and dosage regimes can be determined within the normal skill of the medical practitioner responsible for administration of the composition. For example, for treatment purposes, a therapeutically effective amount of the expression construct, host cell, AR2 modulation agent or pharmaceutical composition according to the invention would be administered to such a subject. A therapeutically effective amount is an amount which is effective to ameliorate one or more symptoms of the disorder.

The dosage may be determined according to various parameters, especially according to the age, weight and condition of the patient to be treated; the route of administration; and the required regimen. A physician will be able to determine the required route of administration and dosage for any particular patient. The dose may be provided as a single dose, but may be repeated or in cases where vector may not have targeted the correct region and/or tissue (such as surgical complication). The treatment is preferably a single permanent treatment, but repeat injections, for example in future years.

Administration may take place once the symptoms of the AR-related disorder have appeared in a subject, for example to treat existing symptoms of the disease.

Combination Therapies

The AR variants, polynucleotides, expression constructs, host cells, AR2 modulation agents and/or pharmaceutical compositions according to the invention can be used in combination, and/or in combination with any other therapy for the treatment of AR-related disorders.

Other

It is to be understood that the terminology used herein is for the purpose of describing particular embodiments of the invention only, and is not intended to be limiting.

In addition as used in this specification and the appended claims, the singular forms "a", "an", and "the" include plural references unless the content clearly dictates otherwise. Thus, for example, reference to "an expression construct" includes "expression constructs", i.e. including two or more expression constructs.

The term "about" or "approximately" means within an acceptable error range for the particular value as determined by one of ordinary skill in the art, which will depend in part on how the value is measured or determined, i.e. the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

An "AR variant" as used herein is a collective term referring to any polypeptide that differs from human AR (ENSP00000363822) (SEQ ID NO: 6), also referred to as AR1 herein, and has retained at least some of the biological activities of AR (e.g. capable of dimerization, capable of binding to an androgen, capable of binding to androgen responsive elements (AREs) and/or capable of transactivation). Hence, the term "AR variant" encompasses AR2 and variants thereof as described herein.

Furthermore, when referring to "≥x" herein, this means equal to or greater than x.

Sequence identity may be calculated using any suitable algorithm. For example the PILEUP and BLAST algorithms can be used to calculate identity or line up sequences (such as identifying equivalent or corresponding sequences (typically on their default settings), for example as described in Altschul (23; 24). Software for performing BLAST analyses is publicly available through the National Center for Biotechnology Information. This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (25) alignments (B) of 50, expectation (E) of 10, M=5, N=4, and a comparison of both strands.

The BLAST algorithm performs a statistical analysis of the similarity between two sequences; see e.g. reference 26. One measure of similarity provided by the BLAST algorithm is the smallest sum probability (P(N)), which provides an indication of the probability by which a match between two polynucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001. Alternatively, the UWGCG Package provides the BESTFIT program which can be used to calculate identity (for example used on its default settings) (27).

All publications, patents and patent applications cited herein, whether supra or infra, are hereby incorporated by reference in their entirety.

The invention will be further described in the following examples, which do not limit the scope of the invention described in the claims.

EXAMPLES

Example 1

Materials and Methods

Mice

Only male mice were used in the analyses.

AR100Q26 and BAC AR121Q131 transgenic animals were used.

To express AR2 in mice, dual promoter AAV vector plasmids were used (provided by SignaGen Laboratories (Rockville, MD)). These plasmids contain an expression cassette consisting of a human elongation factor-1α (EIF1α) promoter followed by AR2 cDNA or mock sequence and human cytomegalovirus (CMV) promoter followed by cDNA encoding GFP. A viral load of $10^{11}$ vector genomes (vg) was injected into the tail veins of SBMA AR100Q mice.

For the knock-down experiments BAC AR121Q mice were injected subcutaneously with 20 mg/kg siRNA suspended in PBS (100 µl). Body weight, rotarod, and grip strength using hanging wire and strength meter (Bioseb) were recorded weekly.

Cell Lines and Reagents

HEK293T cells (ATCC), MCF7 cells (ATCC), immortalised human myoblast cells (MRC CNMD Biobank London L954/1284M-I) were used.

Induced pluripotent stem cells were cultured and differentiated into motor neuron-like cells, according to published protocol (Grunseich C, 2014).

AR induction was performed by addition of dihydrotestosterone, DHT, (Sigma-Aldrich) to a final concentration of 10 nM in the respective cell culture medium. Equal volume of ethanol was added for the uninduced controls.

Cell lysates from control- and SBMA patient-derived primary myoblasts were analysed.

Human Samples

Anonymised brain tissues were used: CGND_HRA_00063, CGND_HRA_00218, CGND_HRA_00224, CGND_HRA_00035, CGND_HRA_00236, CGND_HRA_00399, CGND_HRA_00400, CGND_HRA_00402, CGND_HRA_00411, CGND_HRA_00412, CGND_HRA_00654, CGND_HRA_00655, CGND_HRA_00657, CGND_HRA_00091.

Plasmids Construction

To generate different constructs of AR FL (12Q), AR FL (55Q) and AR2, AR FL (12Q), AR FL (55Q) and AR2 cDNAs were amplified and cloned separately into a mammalian expression vector under cytomegalovirus promoter, with or without N-terminal FLAG epitope tag.

To generate NanoBRET fusion constructs, the PCR amplicons were cloned separately into pFN21A HaloTag CMV Flexi, pFC14K HaloTag CMV Flexi, pFN31K Nluc CMV-neo Flexi and pFC32K Nluc CMV-neo Flexi vectors (Promega). The mutant constructs with mutations at the FxxLF motif (F23,27A/L26A) or (G21E), at the D-box (A596T/S597T), or at the DNA binding domain (A574D) of AR were generated by site-directed mutagenesis.

Luciferase Report Assays

To determine the effect of AR2 on AR-dependent transcriptional activity, HEK293T cells were transiently transfected with 0.5 µg of pARE-E1b-luc (luciferase report vector with an insertion of an androgen responsive element (ARE) upstream of the luc2 gene), 0.5 µg of pRL-TK (Renilla Luciferae control) (Promega), and 0.5 µg AR FL and/or AR2 vector plasmids. Following 24 h of transfection, cells were washed and treated with DHT or equal volume ethanol as negative control. Cells were harvested after 24 h and firefly and Renilla luciferase substrates (Dual-Luciferase Reporter Assay, Promega) were added, and luciferase activity was measured using a microplate spectrophotometer according to the manufacturer's protocol. Renilla luciferase activity was used as the internal normalisation control.

NanoBRET Assay

To investigate the interaction between AR FL protein and AR2 protein, NanoBRET assay was performed (Promega NanoBRET™ Protein: Protein Interaction System). Briefly, HEK293T cells were co-transfected with a Nanoluc luciferase (Nluc) fusion plasmid and a HaloTag fusion plasmid with Lipofectamine 2000 reagent. Nluc-MDM2 and p53-HaloTag pair was included as the positive control, and Nluc-MDM2 and HaloTag-SMAD4 pair as negative control. At 24 h after transfection, cells were treated with or without 10 nM DHT. HaloTag NanoBRET 618 ligand or DMSO (no-ligand control) was added. At 24 h, NanoBRET Nano-Glo substrate was added and NanoBRET readings at 460 nm and 618 nm were obtained. Mean corrected NanoBRET ratio in milliBRET unit was calculated using the formula: Mean corrected Nanobret ratio, $$\text{milliBRET} = [(618 \text{ nmEM}/460 \text{ nmEM})\text{Experimental} - (618 \text{ nmEM}/460 \text{ nmEM})\text{No-ligand control}] \times 1000$$

Chromatin Immunoprecipitation (ChIP)

AR2 ChIP was conducted on MCF7 cells transiently transfected with FLAG-AR2 plasmids. Untransfected MCF7 cells were included as the negative controls. Cells were treated with 10 nM DHT 24 h post transfection. At 48 h, cells were crosslinked with 1% formaldehyde and harvested and lysed. The experiments were conducted as described (28) using 300 µg of chromatin and 14 µg of anti-FLAG antibody (Sigma Aldrich F1804) or anti rabbit IgG antibody (Cell Signaling Technology, 2729).

RNA Pol II ChIP was performed as described (29) on DHT-treated human myoblasts cells using Pol II antibody (Santa Cruz Biotechnology, sc-9001). Purified DNA samples were used for semi-quantitative real-time PCR.

RNA and cDNA Preparation and Real Time-Quantitative PCR (RT-qPCR)

10 mg of muscle or spinal cord tissues were homogenised. Total RNA was isolated. 1 µg of RNA was used for cDNA synthesis with the high-capacity cDNA reverse transcription kit (Applied Biosystems). RT-qPCR reactions were set up with fast SYBR green master mix or TaqMan gene expression master mix (Applied Biosystems) using 20-50 ng of DNA templates.

AR2 Overexpression and Knock-Down in Human Myoblasts

For AR2 overexpression experiments, human myoblasts were transiently transfected with 1 µg of FLAG-AR2 or empty vector and treated with or without DHT 24 h post transfection.

For AR2 knockdown experiments, human myoblasts were treated with 1 µM AR2 targeting siRNA (SBMA-1) or non-targeting siRNA control (NTT) for 48 h. 10 nM DHT was added to the cells 24 h post transfection. siRNAs were synthesised using modified (2'-F, 2'-OMe) phosphoramidite with standard protecting group and cholesterol conjugates as described in reference 30.

Generation of RNA Sequencing Libraries

For the human tissues, RNA-seq libraries were prepared from 500 ng of total RNA using the Illumina TruSeq Stranded Total RNA kit. Sequencing was paired-end (2×150 bp) for target depth of 40M read pairs per sample, using the Illumina HiSeq 4000 platform.

For the iPSC-derived motor neurons, RNA-seq libraries were prepared from 500 ng of total RNA using the RNA-Seq Stranded RiboZero Gold. Sequencing was paired-end (2×75 bp) for target depth of 100M read pairs per sample, using the Illumina HiSeq 4000 platform.

For the human myoblasts where AR2 was overexpressed or knocked-down, mRNA libraries were generated using 1.5 µg of total RNA and the NEBNext® Ultra™ II Directional RNA Library Prep Kit for Illumina.

Libraries were multiplexed, QC'ed and pair-end sequenced on the Illumina HiSeq 4000 platform.

RNA Seq Analysis Pipeline

For the brain and iPSC dataset, paired-end sequence files (.fastq) per sample were quality inspected using the FastQC tool then adaptor clipped (TruSeq3-PE-2.fa:2:30:10) and trimmed to remove 5' nucleotide bias (HEADCROP:12) and low quality calls (TRAILING:20 SLIDINGWINDOW:4:20 MINLEN:15) using the Trimmomatic tool. Surviving intact pairs of reads per sample were reference mapped against the current instance of the human genome (GRCh38.82). Expression per known annotated gene (Homo_sapiens.GRCh38.82.chr.gtf) in Transcripts Per Kilobase Million (TPM) units was pedestalled by 2 then Log2 transformed. Genes not having an expression value>1 post transformation for at least one sample were discarded as not detected while expression across samples for genes not discarded were quantile normalized. To assure quality of the data post normalization, exploratory inspection was performed using Tukey box plot, covariance-based PCA scatterplot and correlation-based heat map. To remove noise-biased expression values, locally weighted scatterplot smoothing (LOWESS) was applied across normalized expression for all genes by sample class (Coefficient of Variation~mean expression). LOWESS fits were then overplotted and inspected to identify the common low-end expression value where the relationship between mean expression (i.e. "signal") and Coefficient of Variation (i.e. "noise") grossly deviated from linearity. Expression values were then floored to equal this value if less, while expression for genes not observed greater than this value for at least one sample were discarded as noise-biased. For genes not discarded, expression differences across sample classes were tested for using the one-factor Analysis of Variance (ANOVA) test under Benjamini-Hochberg (BH) False Discovery Rate (FDR) Multiple Comparison Correction (MCC) condition using sample class as the factor. Genes having a Type III corrected P<0.05 by this test were then subset and the TukeyHSD post-hoc test used to generate mean differences and p-values for each possible pairwise comparison of classes. Genes having a post-hoc P<0.05 for a specific comparison and a linear difference of means>=1.5× for the same comparison were deemed to have expression significantly different between the compared classes respectively. Post testing, sample-to-sample relationships were investigated via covariance-based PCA scatterplot and Pearson correlation-based clustered heat map using the unique union of genes deemed to have a significant difference of expression between at least two classes.

For the human myoblasts data set, sequence reads were adapter and quality trimmed with Trim Galore! (v 0.4.1). Quality control on both raw and trimmed reads was done with FastQC (v 0.11.7) and MultiQC (v 0.9) (31). Trimmed reads were then aligned to the human reference transcriptome (Gencode v29) with Salmon (v 0.12) (32). The resulting quantification files were combined and read into R using the tximport package (v 1.12.3) (33), and differential expression analysis was performed with DESeq2 (v 1.24)38. Pathway analysis was performed on differentially expressed genes using the fgsea package (v 1.10.0) (34).

To narrow down from the 711 differentially regulated genes in human myoblasts with AR2 overexpression to a list of genes that are relevant to SBMA, these genes were overlapped with two publicly available murine SBMA muscle transcriptomic datasets 29,30. Only genes with fold change more than 1.5 from these two lists were included in the analysis. The resulting 57 genes were used to assess transcriptional changes in the AR100Q transgenic mice upon AAV9-AR2 treatment.

Cycloheximide Chase Assay

MCF7 cells were transfected with 1 μg of FLAG-AR2 plasmid. Eight hour post transfection, cells were treated with 10 nM DHT or equal volume ethanol. After 12 h, 100 μg of cycloheximide in DMSO (Sigma-Aldrich) was added to the cells (t=0) and cells were harvested at 0 and 24 h for protein expression analysis. Un-transfected MCF7 cells with cycloheximide treatment were included for comparisons.

Immunoblotting, ELISA

For western blot analysis, proteins were separated on NuPAGE 10% Bis-Tris gel (Invitrogen) and transferred onto PVDF membranes using Invitrogen Novex XCell SureLock mini-cell and XCell II blot module. Membranes were incubated overnight with primary antibody in 1:1000 dilution, anti-AR antibody (Santa Cruz, H-280 or Abcam, ab52615), anti-tubulin (Abcam, ab6160) or anti-vinculin (Sigma-Aldrich, hVIN-1) and for 1 h with secondary antibody in 1:10000 dilution, anti-mouse-HRP conjugated antibody (Invitrogen, 62-6520) or anti-rabbit-HRP conjugated antibody (Invitrogen, 31460).

For co-IP experiments, cells were lysed and centrifuged. The supernatant was incubated overnight at 4° C. with anti-FLAG M2-conjugated magnetic beads (Sigma-Aldrich, M8823), or untagged beads (Chromotek bab-20), as a control. Beads were washed three times with wash buffer [Tris-HCl 0.1 M, NaCl 0.3 M, Triton X-100 1% (v/v), pH 7.5], which was followed by elution with 1× sample buffer, separation on SDS-PAGE gels and analysis by western blotting following standard protocol.

Serum testosterone levels in AR2-versus mock-treated AR100Q mice at 11 weeks of age was measured using the Testosterone Parameter Assay Kit (R&D systems KGE010). according to the manufacturer's protocol.

Immunofluorescence and Immunohistochemistry

For immunofluorescence experiments cross-sections of spinal cord and quadriceps muscle were permeabilized in 0.1% Triton-X 100 and blocked in PBS with 4% BSA and 2% NGS. Sections were incubated overnight at 4° C. in 1:100 dilution with anti-NCAM (Proteintech, 14255-1-AP), anti-PSA-NCAM (EMD Millipore, 5324), or anti-ubiquitin (Abcam, ab7780) antibodies, followed by incubation for 1 h (20-25° C.) with the appropriate Alexa Fluor-conjugated secondary antibodies (ThermoFisher Scientific, 1:1000). To determine the number of inclusions, tissue sections were stained with 1C2 antibody (EMD Millipore, 5TF1-1C2, 1:5000) using the Mouse on Mouse Basic kit (Vector Laboratories BMK-2202).

For quantification, images from at least four contiguous sections were taken using the CaseViewer software and analysed by a blinded investigator to the treatment, using Fiji software40.

AR2 siRNA Screens

A panel of 11 siRNAs targeting all possible regions specific for AR2 transcript and one non-targeting control siRNA (NTT) was designed and synthesised as described (35). These siRNAs are provided in Table 1. The sense and antisense strands of each of these siRNAs correspond to the sequences in SEQ ID NOs: 9-30, respectively. 1 μM of siRNA-AR2 or siRNA-NTT was added to MCF7 cells. Total RNA was extracted from cells. cDNA was prepared and RT-qPCR was performed as described in the previous section using FAM-labelled TaqMan array Hs04272731_s1 specific for AR1, Hs04275959_m1 specific for AR2 and Hs99999905_m1 for GAPDH for normalisation.

TABLE 1 siRNAs targeted to AR2. AS = antisense; S = sense; m = 2'OMe; f = 2'F; P = phosphate; # = phosphothioate linkage

| siRNA | | Antisense (AS) and Sense (S) sequences |
|---|---|---|
| SBMA-1 | AS | 5'-P(mC)#(fC)#(mA)(fA)(mA)(fC)(mU)(fG)(mU)(fG)(mA)(fA)(mG)#(fC)#(mC)#(fA)#(mG)#(fA)#(mG)#(IU)-3' (SEQ ID NO: 9) |
| | S | 5'-(fG)#(mG)#(fC)(mU)(fU)(mC)(fA)(mC)(fA)(mG)(IU)(mU)(IU)#(mG)#(fG)-chol-3' (SEQ ID NO: 10) |
| SBMA-2 | AS | 5'-P(mU)#(fC)#(mC)(fA)(mA)(fA)(mC)(fU)(mG)(fU)(mG)(fA)(mA)#(fG)#(mC)#(fC)#(mA)#(fG)#(mA)#(fG)-3' (SEQ ID NO: 11) |
| | S | 5'-(fG)#(mC)#(fU)(mU)(fC)(mA)(fC)(mA)(fG)(mU)(fU)(mU)(fG)#(mG)#(fA)-chol-3' (SEQ ID NO: 12) |
| SBMA-3 | AS | 5'-P(mC)#(fU)#(mC)(fC)(mA)(fA)(mA)(fC)(mU)(fG)(mU)(fG)(mA)#(fA)#(mG)#(fC)#(mC)#(fA)#(mG)#(fA)-3' (SEQ ID NO: 13) |
| | S | 5'-(fC)#(mU)#(fU)(mC)(fA)(mC)(fA)(mG)(fU)(mU)(fU)(mG)(fG)#(mA)#(fG)-chol-3' (SEQ ID NO: 14) |
| SBMA-4 | AS | 5'-P(mU)#(fC)#(mU)(fC)(mC)(fA)(mA(fA)(mC)(fU)(mG)(fU)(mG)#(fA)#(mA)#(fG)#(mC)#(fC)#(mA)#(fG)-3' (SEQ ID NO: 15) |
| | S | 5'-(fU)#(mU)#(fC)(mA)(fC)(mA)(fG)(mU)(fU)(mU)(fG)(mG)(fA)#(mG)#(fA)-chol-3' (SEQ ID NO: 16) |
| SBMA-5 | AS | 5'-P(mG)#(fU)#(mC)(fU)(mC)(fC)(mA)(fA)(mA)(fC)(mU)(fG)(mU)#(fG)#(mA)#(fA)#(mG)#(fC)#(mC)#(fA)-3' (SEQ ID NO: 17) |
| | S | 5'-(fU)#(mC)#(fA)(mC)(fA)(mG)(fU)(mU)(fU)(mG)(fG)(mA)(fG)#(mA)#(fC)-chol-3' (SEQ ID NO: 18) |

TABLE 1-continued siRNAs targeted to AR2. AS = antisense; S = sense; m = 2'OMe; f = 2'F; P = phosphate; # = phosphothioate linkage

| siRNA | | Antisense (AS) and Sense (S) sequences |
|---|---|---|
| SBMA-6 | AS | 5'-P(mA)#(fG)#(mU)(fC)(mU)(fC)(mC)(fA)(mA)(fA)(mC)(fU)(mG)#(IU)#(mG)#(fA)#(mA)#(fG)#(mC)#(fC)-3' (SEQ ID NO: 19) |
| | S | 5'-(fC)#(mA)#(fC)(mA)(fG)(mU)(IU)(mU)(fG)(mG)(fA)(mG)(fA)#(mC)#(fU)-chol-3' (SEQ ID NO:20) |
| SBMA-7 | AS | 5'-P(mC)#(fA)#(mG)(fU)(mC)(fU)(mC)(fC)(mA)(fA)(mA)(fC)(mU)#(fG)#(mU)#(fG)#(mA)#(fA)#(mG)#(fC)-3' (SEQ ID NO:21) |
| | S | 5'-(fA)#(mC)#(fA)(mG)(fU)(mU)(fU)(mG)(fG)(mA)(fG)(mA)(fC)#(mU)#(fG)-chol-3' (SEQ ID NO: 22) |
| SBMA-8 | AS | 5'-P(mG)#(fC)#(mA)(fG)(mU)(fC)(mU)(fC)(mC)(fA)(mA)(fA)(mC)#(IU)#(mG)#(IU)#(mG)#(fA)#(mA)#(fG)-3' (SEQ ID NO: 23) |
| | S | 5'-(fC)#(mA)#(fG)(mU)(fU)(mU)(fG)(mG)(fA)(mG)(fA)(mC)(fU)#(mG)#(fC)-chol-3' (SEQ ID NO: 24) |
| SBMA-9 | AS | 5'-P(mG)#(fG)#(mC)(fA)(mG)(fU)(mC)(fU)(mC)(fC)(mA)(fA)(mA)#(fC)#(mU)#(fG)#(mU)#(fG)#(mA)#(fA)3' (SEQ ID NO: 25) |
| | S | 5'-(fA)#(mG)#(fU)(mU)(fU)(mG)(fG)(mA)(fG)(mA)(fC)(mU)(fG)#(mC)#(fC)-chol-3' (SEQ ID NO: 26) |
| SBMA-10 | AS | 5'-P(mU)#(fG)#(mG)(fC)(mA)(fG)(mU)(fC)(mU)(fC)(mC)(fA)(mA)#(fA)#(mC)#(IU)#(mG)#(fU)#(mG)#(fA)-3' (SEQ ID NO: 27) |
| | S | 5'-(fG)#(mU)#(fU)(mU)(fG)(mG)(fA)(mG)(fA)(mC)(fU)(mG)(fC)#(mC)#(fA)-chol-3' (SEQ ID NO: 28) |
| SBMA-11 | AS | 5'-P(mC)#(fU)#(mG)(fG)(mC)(fA)(mG)(fU)(mC)(fU)(mC)(fC)(mA)#(fA)#(mA)#(fC)#(mU)#(fG)#(mU)#(fG)-3' (SEQ ID NO:29) |
| | s | 5'-(IU)#(mU)#(IU)(mG)(fG)(mA)(fG)(mA)(fC)(mU)(fG)(mC)(fC)#(mA)#(fG)-chol-3' (SEQ ID NO:30) |

Statistical Analyses

Survival, time to disease onset, and latency to fall of SBMA mice was determined by Kaplan-Meier estimation, and comparisons were made with the log-rank test. A one-way ANOVA was conducted to compare the effect of the treatment on weights of the animals, using treatment as a between-subjects factor and time as a within-subjects factor. All other data were analysed by a two-tailed t-test analysis, or one-tailed, where indicated.

Expression of AR Variants in Human Brain

The physiological levels of AR variants expression in human brain were determined. By employing RNA-seq at high sequencing depth (>100 million per reads) using RNA from human medial and lateral motor cortex, cervical and lumbar spinal cord, and iPS-derived motor neurons, the inventors found that AR splice variant 2 (ENST00000396043; AR2) was the most highly expressed AR variant, also compared to the canonical splice variant 1 (ENST00000374690; AR1) (FIG. 1a). No difference was observed in motor neurons from SBMA patients compared to controls. Interestingly, AR2 was found to be particularly abundant in androgen responsive tissues, such as prostate and muscle, suggesting a role in AR regulation (FIG. 1b).

Figure 1C:
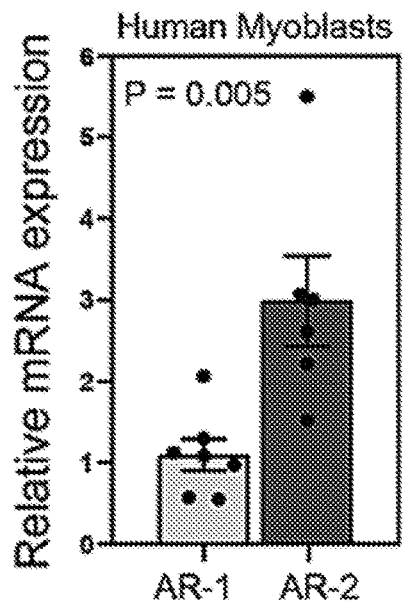
Figure 1D:
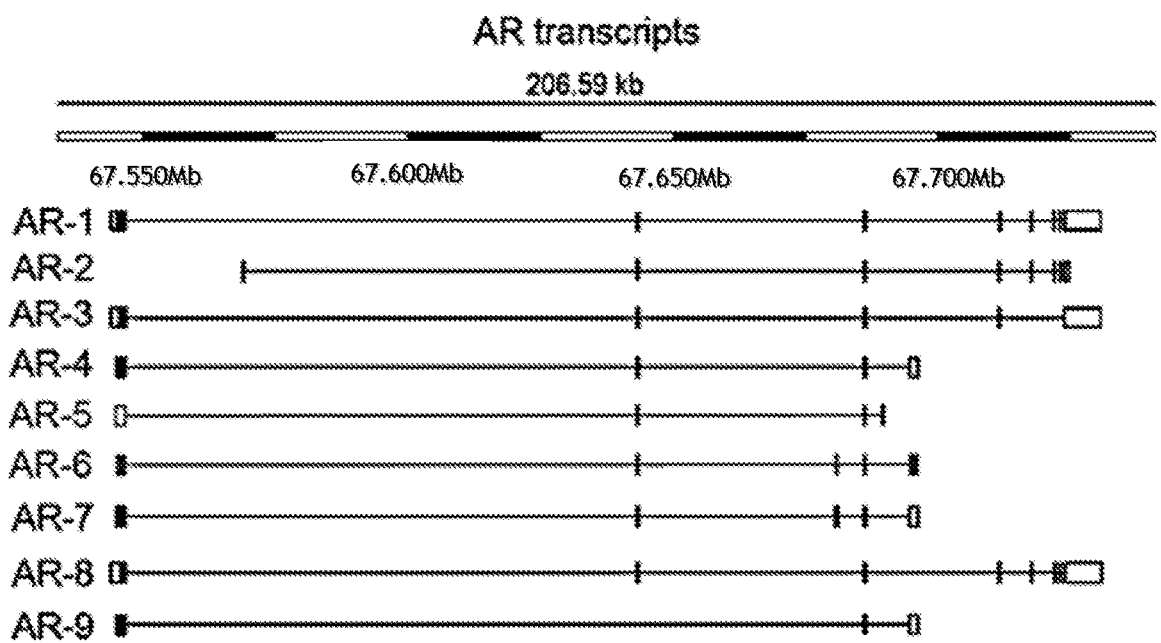
Figure 1E:
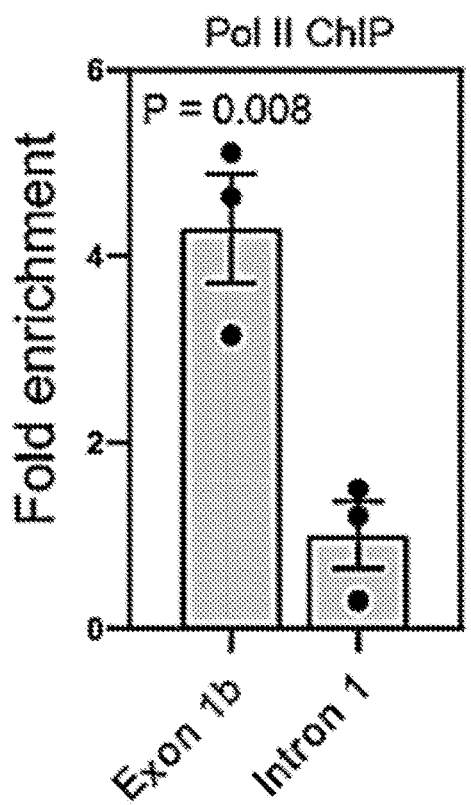
Figure 1F:
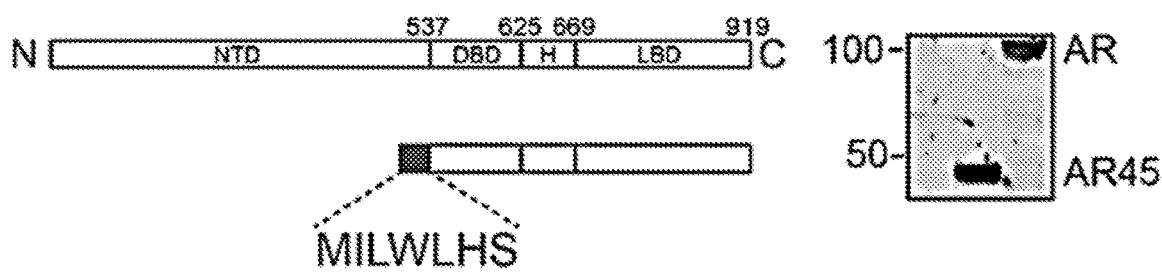

The inventors confirmed that its expression levels were higher compared to AR1 in human myoblasts both from controls and SBMA subjects (FIG. 1c). AR2 is a naturally occurring variant, originally identified via rapid amplification of cDNA ends (RACE) from human placenta tissue (17). AR2 mRNA was found to arise from inclusion of an alternative exon 1 (exon 1b) situated 22.1 kb downstream of exon 1 (FIG. 1d). This chromatin locus is functionally accessible and actively transcribed, as indicated by the DNase I hypersensitivity and ChIP-seq tracks and the quantification of Pol II occupancy on exon 1b by chromatin immunoprecipitation assay (FIG. 1e). Multiple sequence analysis of exon 1b and flanking regions suggest a close to 100% homology with Rhesus macaque and poor conservation in mouse and rat, where a stop codon downstream of the start codon infers that AR2 splice variant is not present in these species (18). The inventors confirmed no expression of AR2 in wild type animals. The encoded protein containing a unique N-terminal sequence in place of the canonical NTD has a molecular mass of 45 kDa, hence AR2 is also known as AR45(17) (FIG. 1f).

Role of AR2 on AR Biology

Figure 2A:
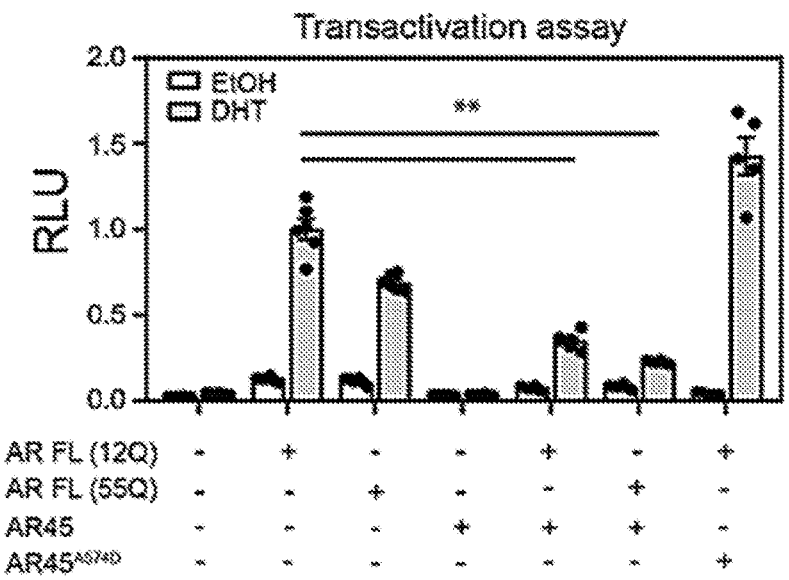
FIG. 2 shows that AR2 modulates full length AR transcriptional activity. a) HEK293T cells were transfected with the indicated vectors together with both the luciferase pARE-E1b-Luc and the β-galactosidase pCMVβ reporter constructs. AR transactivation was measured in the presence and absence of DHT by luciferase assay. Data are mean±s.e.m. Each dot represents one replicate (n=5). P<0.01. b) Luciferase assay was performed with increasing concentration of AR2 constructs, indicated in μg. c) Indicated fusion constructs were co-transfected into HEK293T cells and BRET signal was measured after the addition of the NanoBRET HaloTag 618 ligand. The corrected NanoBRET ratio is expressed as milliBRET units (mBU). Data are mean±s.e.m. Each dot represents one replicate (n=3). P<0.01. d) mRNA relative expression of AR1 and AR2 transcripts following 48 h treatment with multiple siRNAs targeting the unique N-terminal sequence of AR2. Data are normalised to a non-targeting sequence (NTS) siRNA with the same chemical backbone. AR2 expression levels are significantly reduced for all tested siRNAs (P<0.01). Expression values for untransfected (UT) myoblasts are also shown. Data are mean±s.e.m. Each dot represents one replicate (n=3). e) Pie chart breakdown of ARE-containing genes among differentially expressed transcripts in human myoblasts where AR2 was either overexpressed or knocked down. Up-regulated and downregulated genes are indicated in red/blue, and pink/light blue, respectively. f) and g) Heat map depicting hierarchical clustering of sample-to-sample distance. Variance-stabilized transformed RNA-seq read counts for ARE-containing transcripts were used to calculate sample-to-sample Euclidean distances (grey scale) for hierarchical clustering. OE: overexpression; EV: empty vector; siRNA: siRNA-treated; NTC: non-targeting control. Transcripts in the over-expression group clustered into 3 main groups: very down-regulated (1), mildly down-regulated (2), and up-regulated (3). h) Cross-linked chromatin from MCF7 cells transiently expressing AR2-FLAG, treated for 24 h with EtOH or DHT, was immunoprecipitated with anti-FLAG antibody or IgG isotype control. GREB1, ZNF485, and EHF are known AR target genes. Data are mean±s.e.m. Each dot represents one replicate (n=3). **P<0.01. i) Representation of the working model: In addition to forming AR:AR homodimers, AR heterodimerises with AR2, resulting in a less efficient transactivating complex.
Figure 2B:
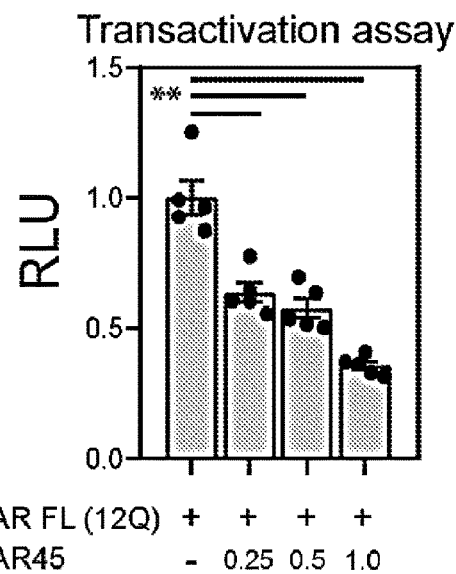

The inventors next went on to characterise the role of AR2 on AR biology. AR2 led to a dose-dependent suppression of full length AR transcriptional activity in response to DHT and this effect was abolished by introducing in the transgene the DBD inactivating substitution A574D (FIG. 2a; FIG. 2b). Overall these findings suggest that the AR2 effect on AR transactivation is selective and requires binding to DNA (FIG. 2a). Of note AR2 alone was not able to activate transcription (FIG. 2a). Activation of transcription requires AR dimerization, which is mediated mainly through N/C-terminal interactions via the FxxLF motif, and DBD/DBD interactions via the dimerization box (D-box) (19).

Figure 2C:
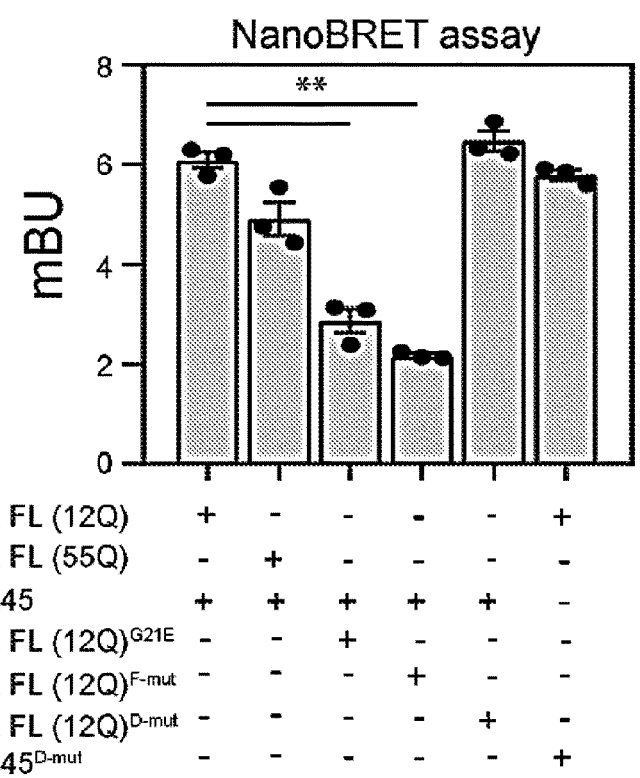

Because the DBD and LBD are conserved, the inventors hypothesized that AR can also form heterodimers with AR2. The inventors tested this hypothesis by using a bioluminescence resonance energy transfer (BRET) assay, which allows real-time detection of complex formation (20). All combinations of N- and C-terminal fusion constructs were transfected into the AR-null cells and one of the combination exhibiting the highest BRET signal was chosen for further analysis. BRET saturation curve indicated specific protein-protein interaction. Mutation in the FxxLF motif (F23, 27A/L26A; F-mut) or N-terminal of this motif (G21E) and not the D-box motif (A596T/S597T; D-mut) inhibited the AR/AR2 dimerization (FIG. 2c). Interestingly, the inventors also found that AR2 forms homodimers. The AR/AR2 interaction was further demonstrated by co-immunoprecipitation assay.

AR protein levels were not affected by the presence of AR2 in a cycloheximide chase experiment, suggesting that AR2 does not alter AR protein steady state.

AR2 Function

Figure 2D:
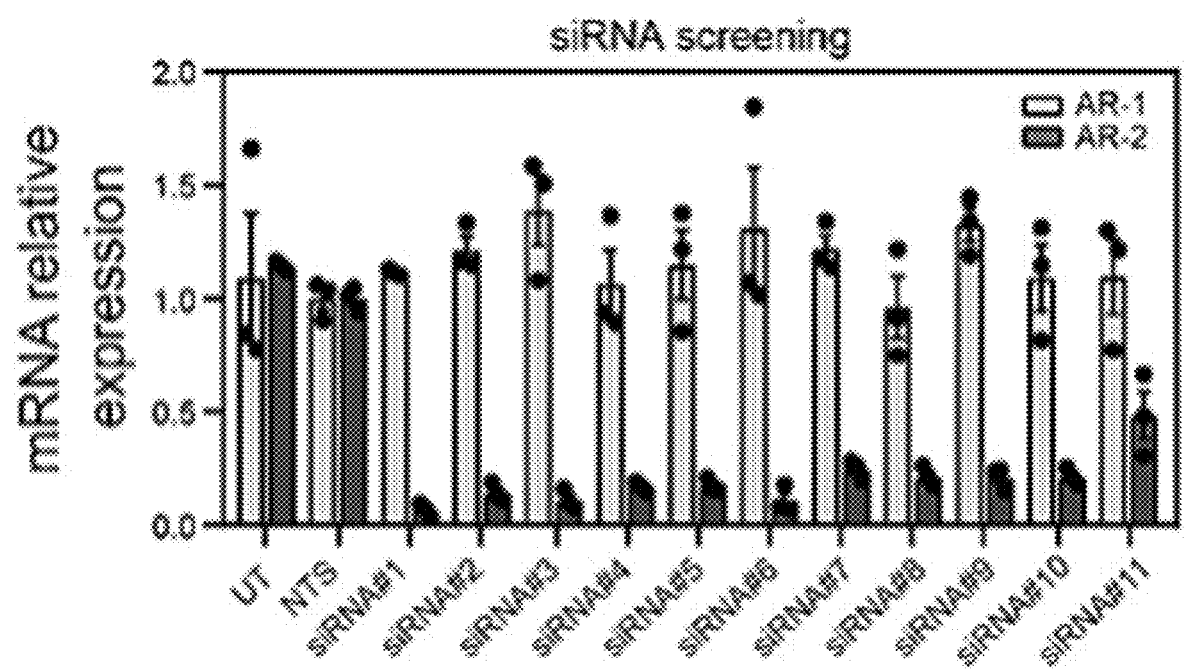
Figure 2E:
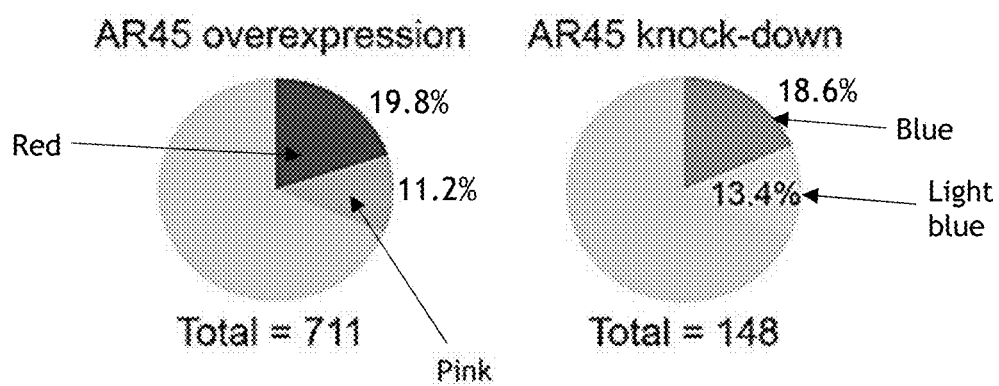
Figure 2F:
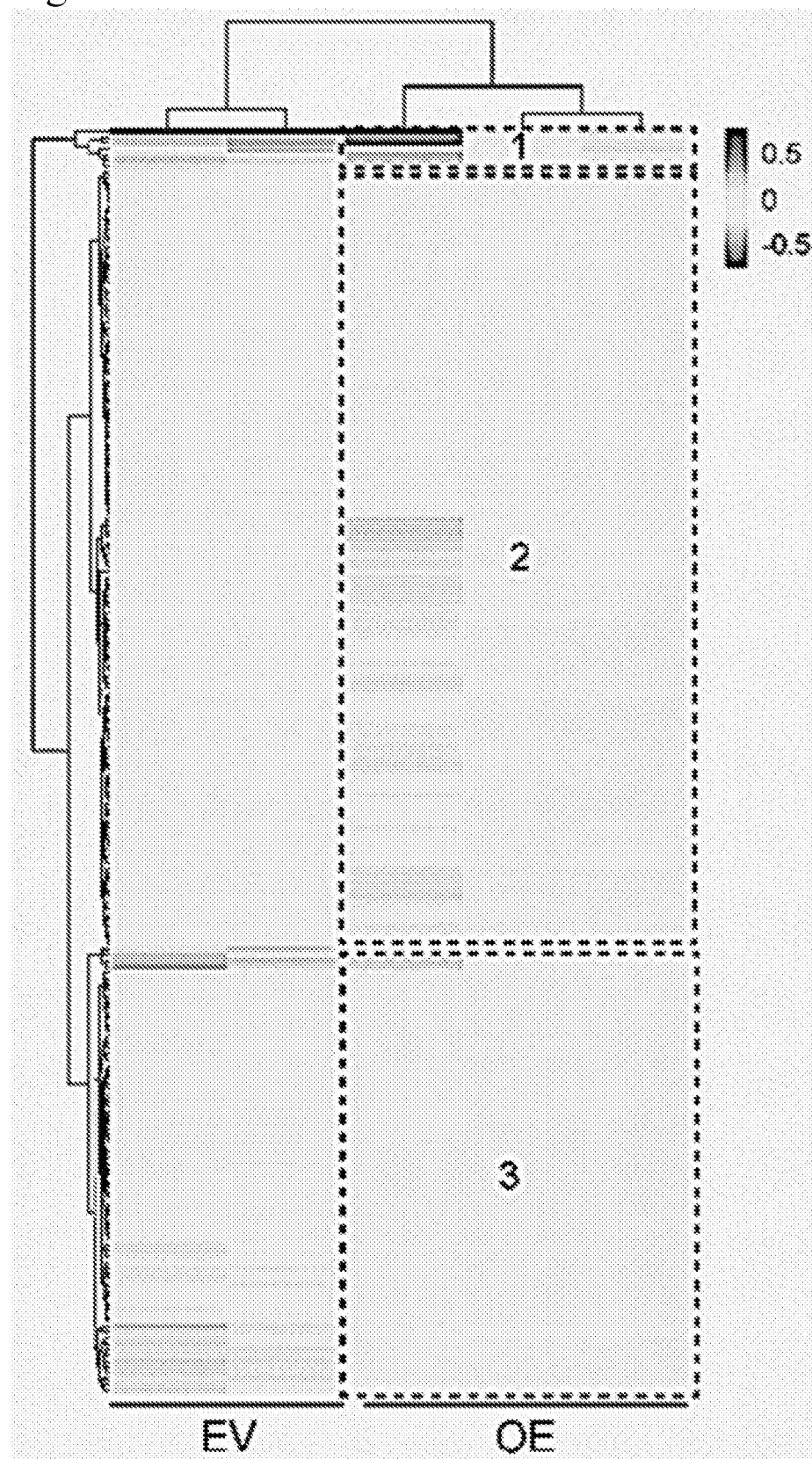
Figure 2G:
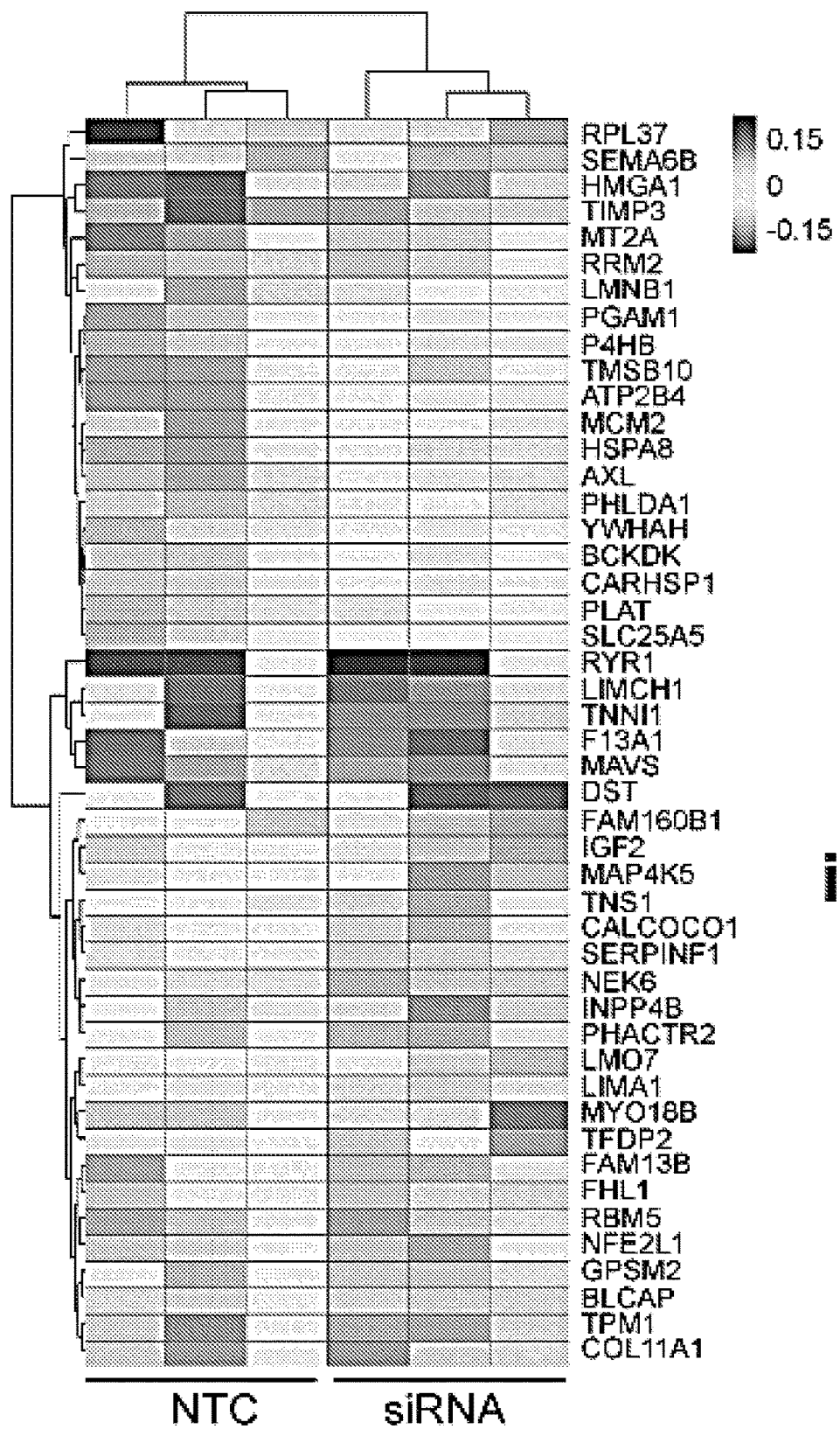

To better delineate AR2 function, the inventors next profiled gene expression in human myoblasts where AR2 was either overexpressed (OE) or knocked-down (KD). First the inventors designed 11 combinations of small interfering RNAs (siRNA), spanning exon 1b sequence. In order to improve their pharmacokinetic properties these siRNAs were chemically modified and lipid conjugated (21). These siRNAs resulted in selective silencing of endogenous AR2 (ranging from 45 to 90%) (FIG. 2d). AR2 overexpression and knock-down using the best performing siRNA were confirmed by qRT-PCR. Principal component analysis (PCA) on the expression data showed clustering of samples according to treatment. Using differential expression analysis (DEseq; $P<0.05$, fold change $>1.5$), the inventors observed a slightly higher number of upregulated transcripts, both upon AR2 overexpression (63%) and knock-down (59%). Gene set enrichment analysis to identify the biological processes associated with AR2-regulated genes showed down-regulation of genes associated with AR response in the AR2 OE samples, while the opposite trend was observed upon AR2 KD. Of the list of genes differentially expressed, 31% and 32% respectively in the OE and KD data set were found to contain an ARE sequence in the promoter region (FIG. 2e). Moreover, several AR target genes in AR2 OE myoblasts, e.g. MYBPH (cluster 1), C3 (cluster 2), MYL4, CASQ2, IGF2 (cluster 3), showed the same pattern of dysregulation compared to muscle of genomic AR knock-out mice (22) (FIG. 2f). Of note, knock-down of endogenous AR2 resulted in downregulation of HSPA8, a member of the chaperone-assisted selective autophagy complex and upregulation of NFE2L1, a master regulator of proteasome subunits, intriguingly suggesting that AR2 may contribute to hamper androgen-induced cell stress signals (23, 24) (FIG. 2g).

Figure 2H:
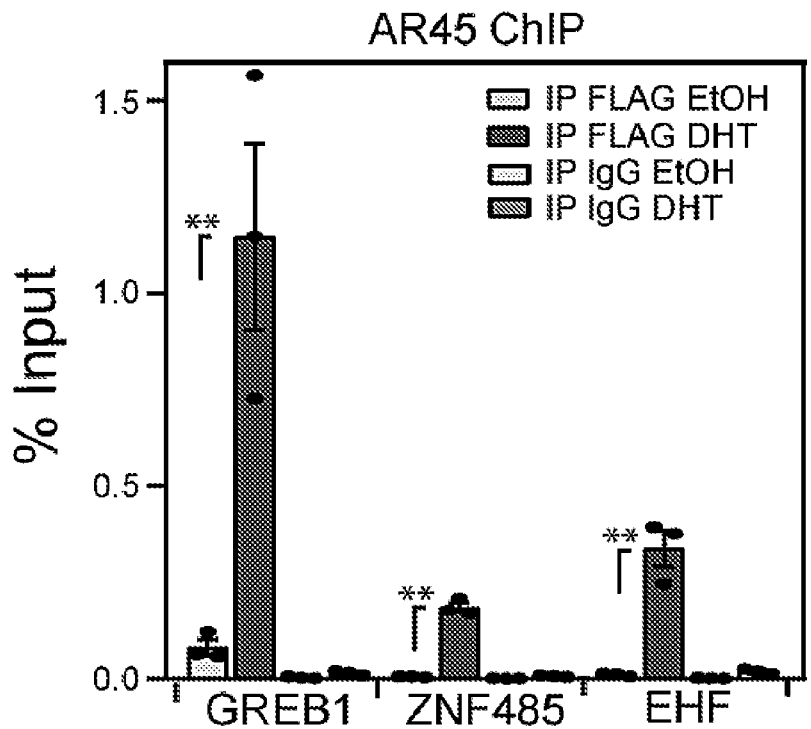
Figure 2I:
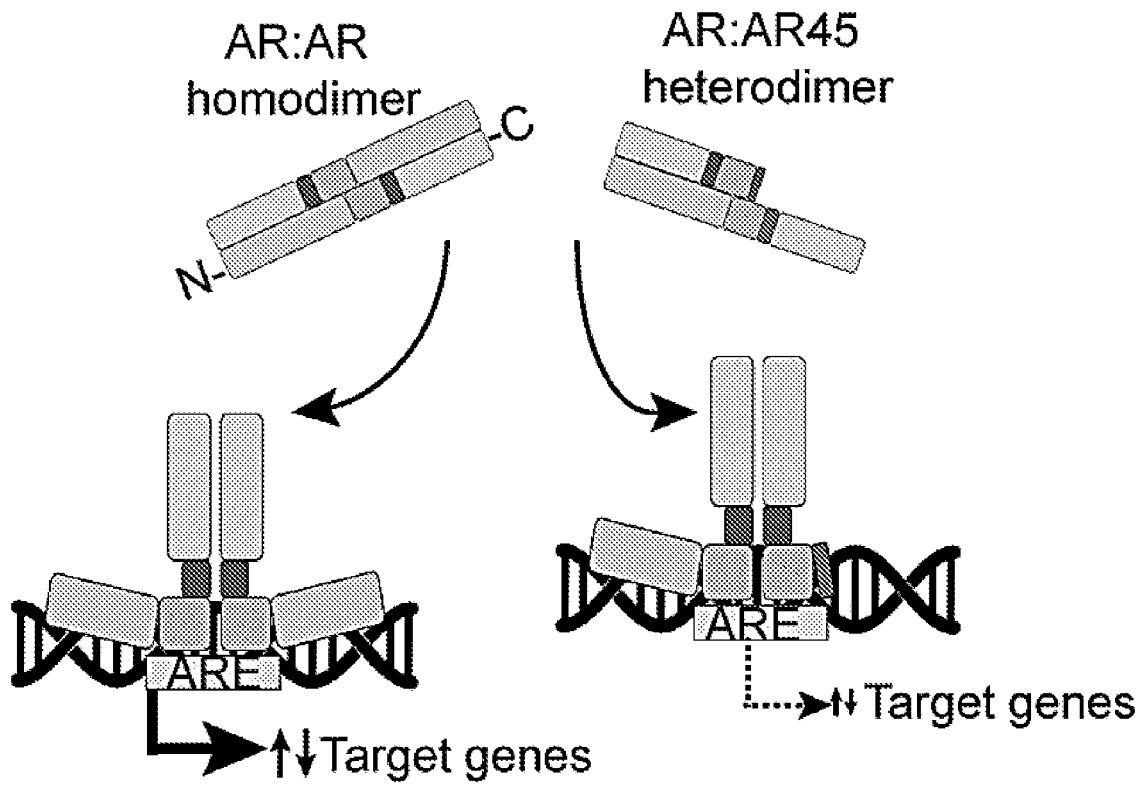

To investigate whether AR and AR2 co-occupy the same genomic loci, the inventors carried out ChIP experiments at known AR target genes (GREB1, ZNF485, and EHF (25). The inventors detected positive signal enrichment (FIG. 2h), indicating a functional interaction of the splice variants at the ARE locus. The inventors confirmed that overexpression of AR2 resulted in reduced transactivation of those targets. Taken together, these results demonstrate that AR2 forms heterodimers with AR and represses transcription of AR-responsive genes (FIG. 2i).

AR2 Overexpression Ameliorates the Disease Phenotype in SBMA Mice

Figure 3A:
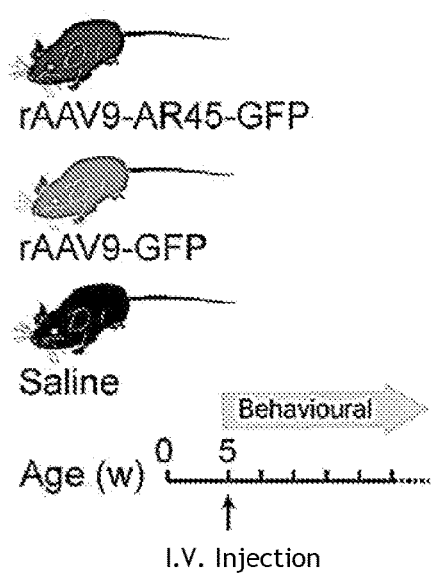
FIG. 3 shows that overexpression of AR2 improves the phenotypic outcomes and pathologic degeneration in a preclinical trial in SBMA mice. a) Schematic diagram of the design of the animal experiment. The colour scheme is conserved across the figure (AAV9-AR2: n=8; AAV9-mock: n=6; saline: n=4). b) Kaplan-Meier survival estimation of AR100Q mice (log-rank test). c) The median disease onset is delayed in AR2-treated mice. d) Mean body weight of AR100Q mice from 5 weeks of age to end stage. e) Kaplan-Meier estimation of rotarod performance of AR100Q mice. Failure is set as drop of riding time≥30 sec. f) Representative skeletal muscle sections (gastrocnemius) from 11-week-old wild type and AR100Q mice treated with rAVV9 expressing AR2 or mock sequence. Sections were stained with H&E or NADH for muscle morphology. Arrows indicate atrophied myofibers. Arrowheads indicate myofibers containing centralized nuclei. Scale bars represent 20 μm (top). Relative frequency distribution of myofiber cross-sectional diameter size sorted by transgene genotype and AR2-treated vs mock (bottom). g) Representative images of skeletal muscle stained with antibodies against NCAM and PSA-NCAM in AR100Q mice treated with rAAV9 expressing AR2 or mock sequence. Scale bars represent 50 μm (top). Quantification of PSA-NCAM/NCAM colocalized regions. n=6 fields for all groups, 3 mice per group (bottom). h) Ubiquitin staining in spinal cord and muscle cross sections of mock- and AR2-treated AR100Q mice. Representative images are shown from 3 independent experiments. Scale bars represent 20 μm for spinal cord sections and 10 μm for muscle sections. i) Representative spinal cord and skeletal muscle cross sections from mock- and AR2-treated AR100Q mice from 3 independent experiments. Sections were stained with 1C2 antibody. Scale bars represent 100 μm. j) mRNA expression levels normalised to Hprt housekeeping gene in spinal cord (MEGF10 and NQO1) and muscle (CACNG1, CHRNA1, MYBPC2, MYBPH, TNNT3, and UNC45B) lysates from mock- or AR2-treated AR100Q mice. Values are expressed as fold change to wild type animals, set as 1.

Given its role as a transcriptional repressor of AR activity, the inventors hypothesized that overexpression of AR2 is able to ameliorate the disease phenotype in SBMA mice. Male transgenic mice were peripherally injected with AAV9 encoding AR2 cDNA, green fluorescent protein (GFP), or saline at 5 weeks of age (FIG. 3a). This model expresses a polyQ AR transgene (AR100Q) and exhibits a disease-relevant phenotype (26). Beginning at approximately 7 weeks of age, these mice demonstrate rapid androgen-dependent declines in survival, body weight, and rotarod activity compared with non-transgenic littermates (26). The treatment resulted in widespread transduction, particularly in muscle, a primary site of pathology in this disease (27, 28), as indicated by high AR2 expression 6 weeks after injection.

Figure 3B:
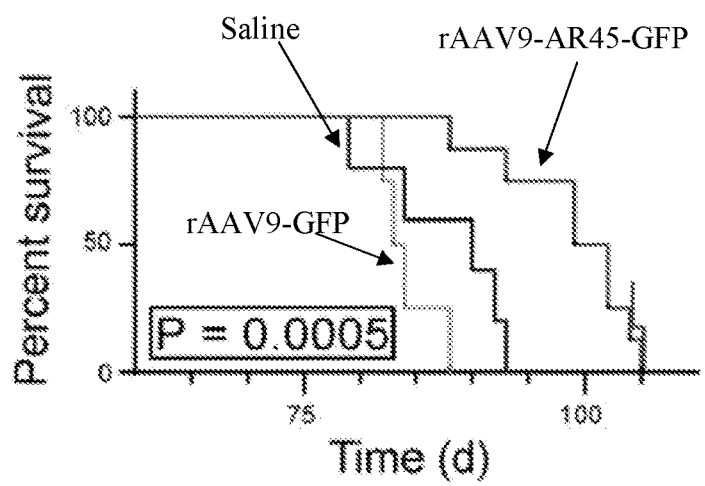
Figure 3C:
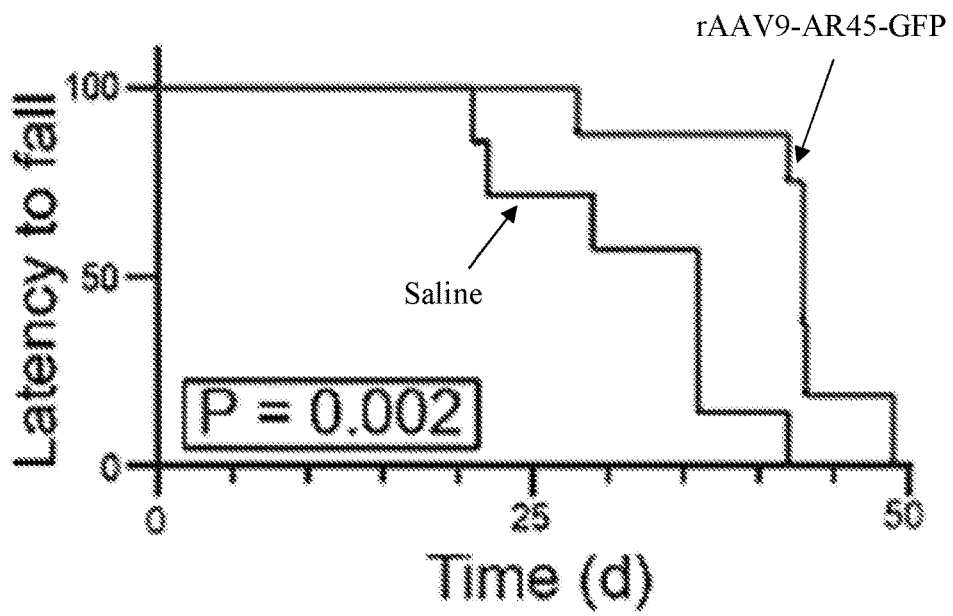
Figure 3D:
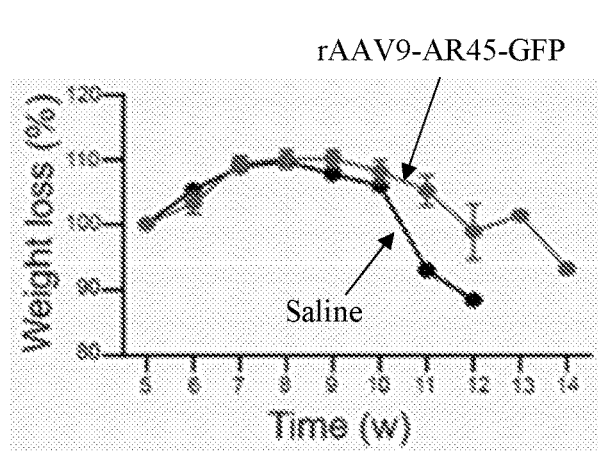
Figure 3E:
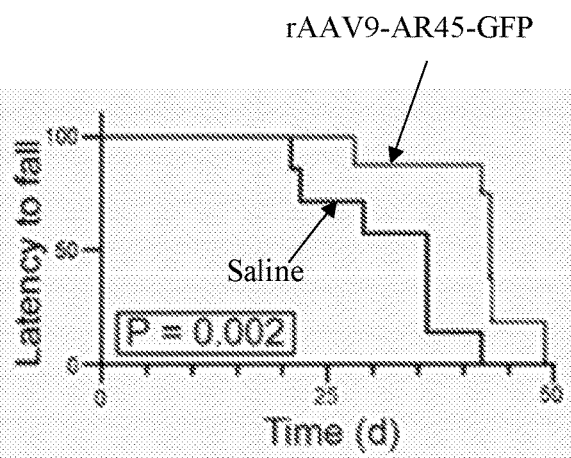
Figure 3F:
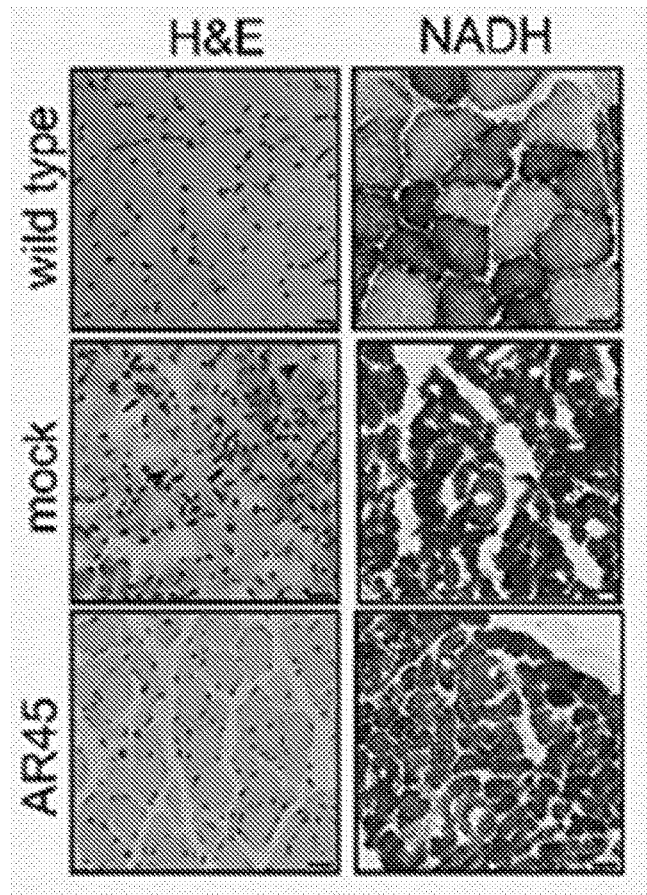
Figure 3G:
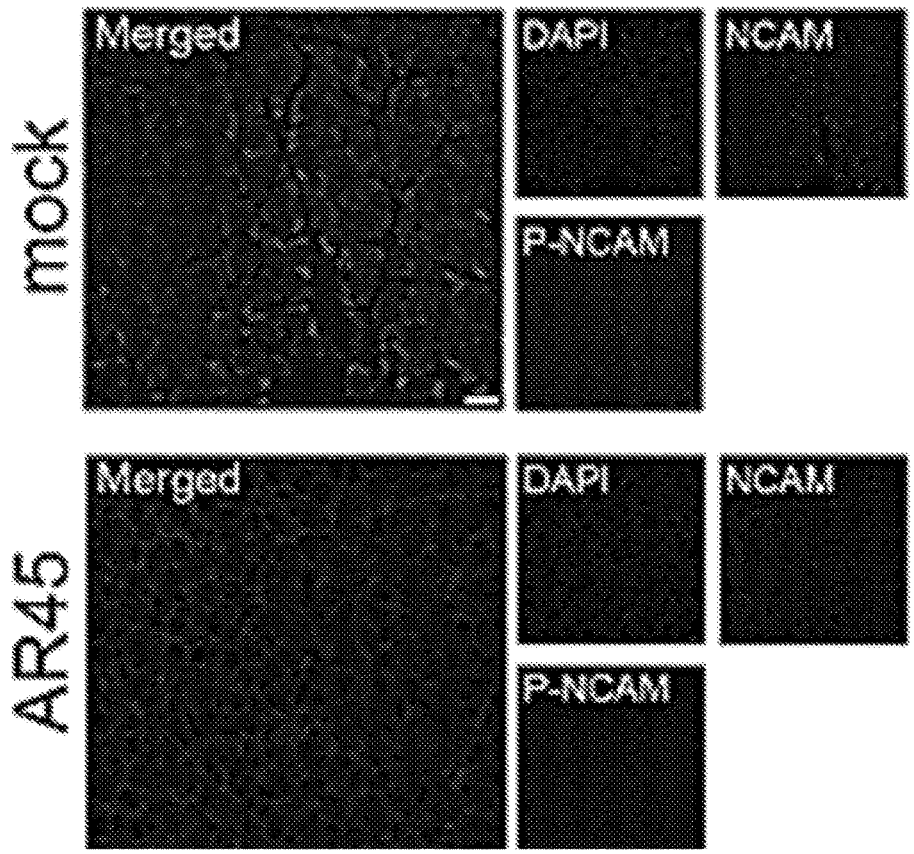
Figure 3G:
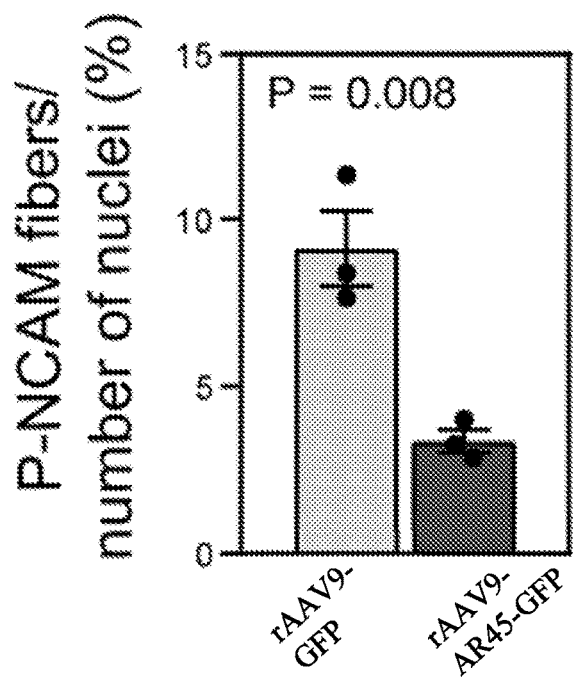

AR2 overexpression significantly prolonged survival (FIG. 3b), delayed disease onset (FIG. 3c), improved weight loss (FIG. 3d) and rotarod activity (FIG. 3e). Furthermore, the inventors observed a dramatic amelioration of the pathologic appearance of skeletal muscle (FIG. 3f), with reduced co-localization of NCAM/PSA-NCAM staining, a marker of denervation/re-innervation activity, consistent with amelioration of the neuromuscular phenotype (FIG. 3g). AR2-treated mice had normal levels of serum testosterone.

Figure 3H:
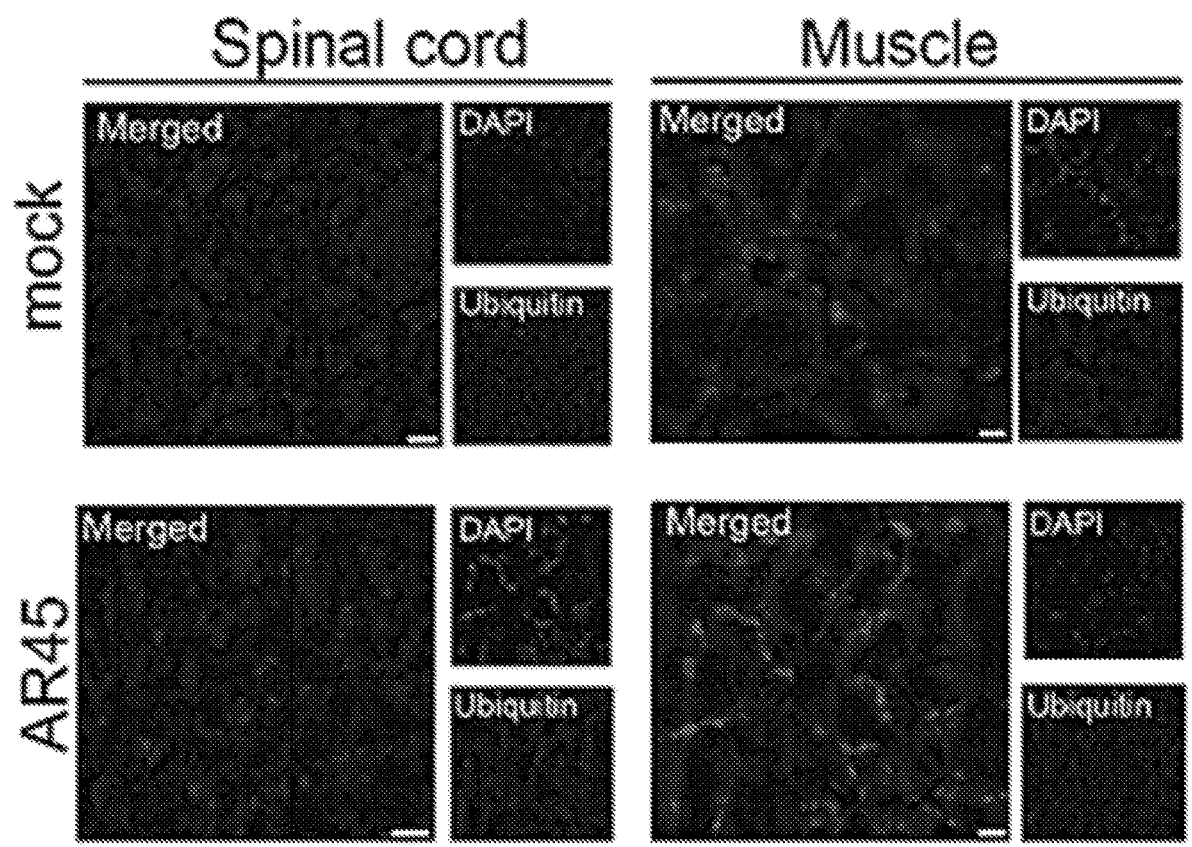
Figure 3I:
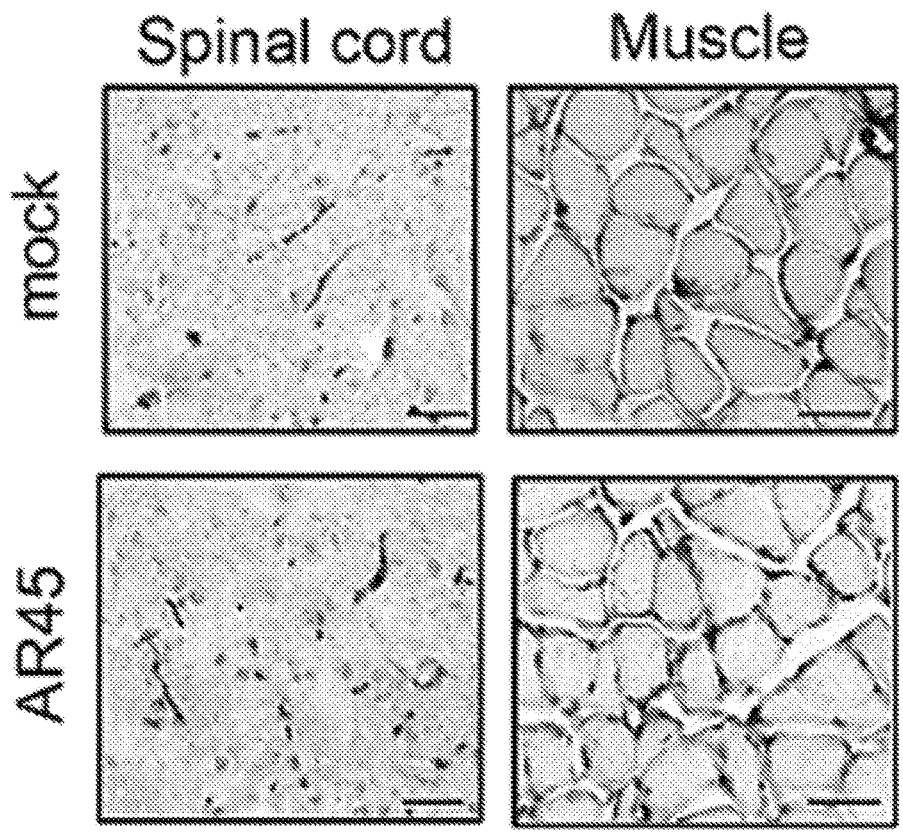

As expected, no changes in AR protein levels, as well as in the number of ubiquitin- (FIG. 3h) and polyQ-positive (FIG. 3i) inclusions in both spinal cord and skeletal muscle were observed, supporting a model where therapeutic benefit can be achieved independently of the polyQ-mediated proteotoxicity.

Figure 3J:
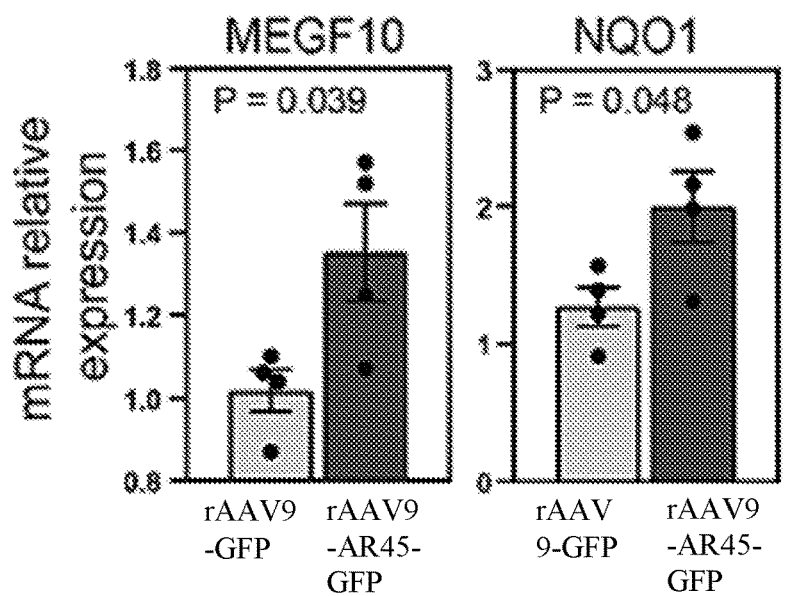
Figure 3K:
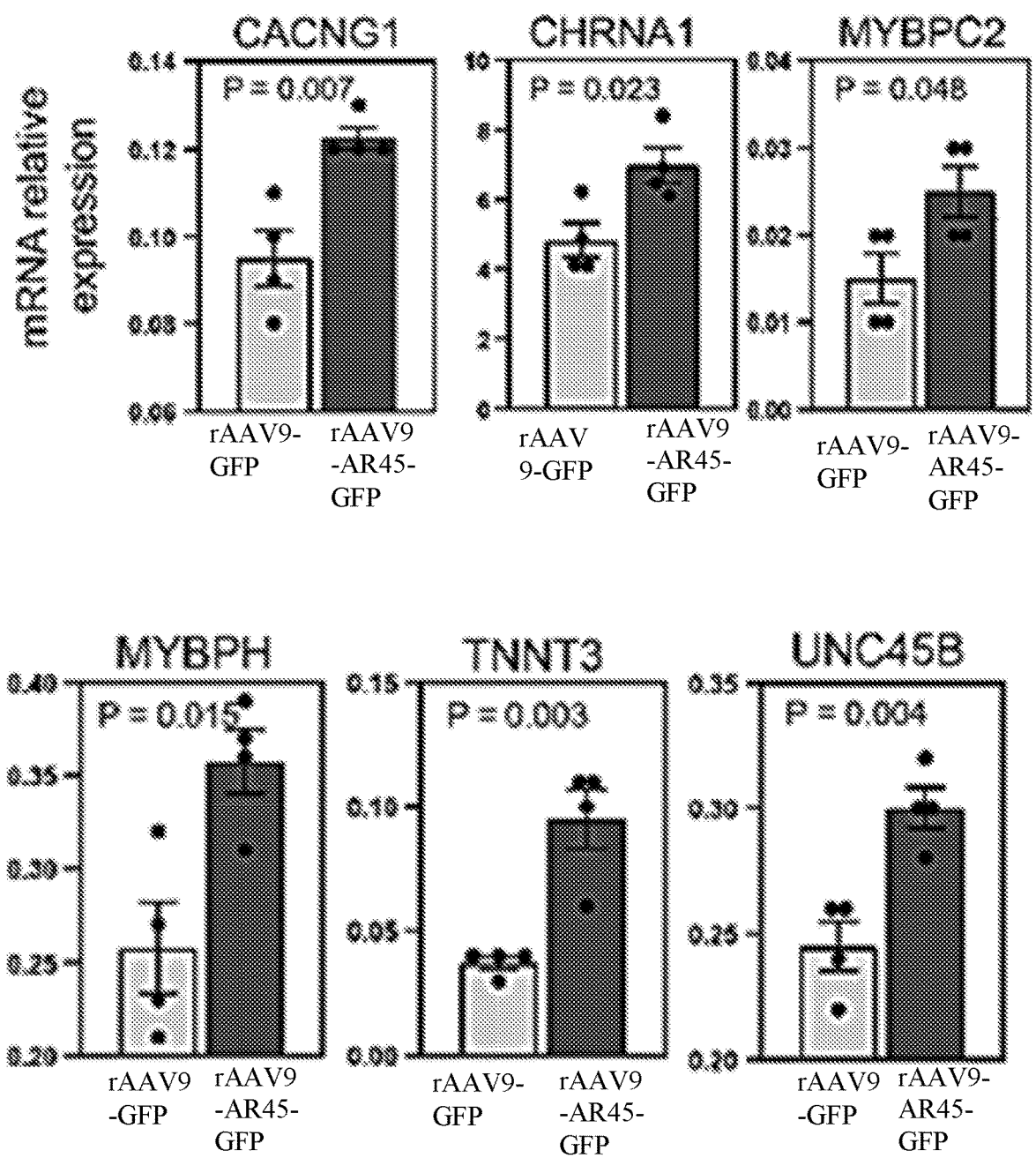

To confirm molecular activity of splice variant overexpression, the inventors selected two genes in spinal cord (MEGF10, NQO1) and five in muscle (CACNG1, CHRNA1, MYBPC2, MYBPH, TNNT3, UNC45B) among known dysregulated transcripts in SBMA mice (29, 30), that were upregulated in the OE data set in human myoblasts, and confirmed a statistically significant increase in expression upon AR2 treatment in vivo (FIG. 3j).

siRNA AR2 Treatment Exacerbates Locomotor Function

The inventors treated a cohort of male transgenic mice harbouring the entire AR gene (27) and therefore endogenously expressing this splice variant, with lipid-conjugated siRNA targeting AR2.

Table 2 shows the sense and antisense AR2-targeting and mock sequences for this study. The sequence of the sense strand (S) of the siRNA targeting AR2 is also provided in SEQ ID NO: 31. The sequence of the antisense strand (AS) of the siRNA targeting AR2 is also provided in SEQ ID NO: 32. The sequence of the sense strand (S) of the mock siRNA is also provided in SEQ ID NO: 32. The sequence of the antisense strand (AS) of the mock siRNA is also provided in SEQ ID NO: 34. The phosphocholine docosanoic acid (PC-DCA) conjugate was covalently attached to the 3'-end of the siRNA sense strand.

TABLE 2 siRNAs used in this study. AS = Antisense; S = Sense; m = 2'OMe; f = 2'F; P = phosphate; # = phosphothioate linkage; PC-DCA = Phosphocholine Docasonoic Acid; VP = Vinylphosphonate

| Name | Strand | Sequence |
| --- | --- | --- |
| siRNA AR-2 | S | 5'-(fG)#(mG)#(fC)(mU)(fU)(mC)(fA)(mC)(fA)(mG)(fU)(mU)(fU) #(mG)#(fG)-PC-DCA-3' (SEQ ID NO: 31) |
| | AS | 5'-VP(mU)#(fC)#(mA)(fA)(mA)(fC)(mU)(fG)(mU)(fG)(mA)(fA) (mG)#(fC)#(mC)#(fA)#(mG)#(fA)#(mG)#(fU)-3' SEQ ID NO: 32 |

TABLE 2-continued siRNAs used in this study. AS = Antisense; S = Sense; m = 2'OMe; f = 2'F;
P = phosphate; # = phosphothioate linkage; PC-DCA = Phosphocholine
Docasonoic Acid; VP = Vinylphosphonate

| Name | Strand | Sequence |
|---|---|---|
| Mock | S | 5'-(fC)#(mA)#(fG)(mU)(fA)(mA)(fA)(mG)(fA)(mG)(fA)(mU)(fU)#(mA)#(fA)-PC-DCA-3' (SEQ ID NO: 33) |
|  | AS | 5'-VP(mU)#(fU)#(mA)(fA)(mU)(fC)(mU)(fC)(mU)(fU)(mU)(fA)(mC)#(fU)#(mG)#(fA)#(mU)#(fA)#(mU)#(fA)-3' (SEQ ID NO: 34) |

Figure 4A:
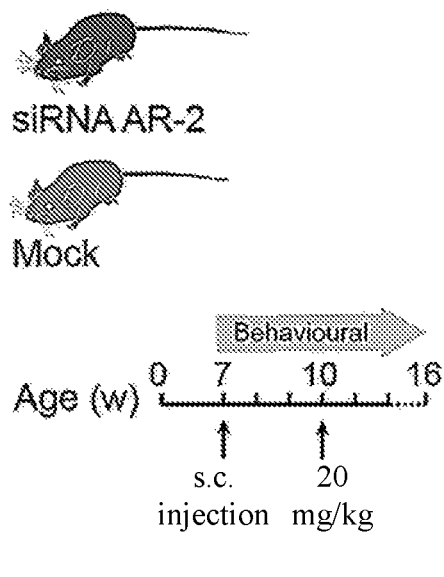
FIG. 4a) shows a schematic diagram of the design of the animal experiment. The colour scheme is conserved across the figure (siRNA AR-2: n=6; Mock: n=5). b) mRNA levels of endogenous AR2 in quadriceps muscles from siRNA-treated versus mock-treated AR121Q mice normalised to Hprt housekeeping gene. Data are mean±s.e.m. Each dot represents one replicate (n=3). One-tail t-test. c) Mean±s.e.m grip strength expressed in units of force (N: Newton) in the last 3 weeks of the study of the AR121Q mice treated with siRNA targeting AR2 or mock sequence. d) Rotarod performance of AR121Q mice treated with siRNA targeting AR-2 or mock sequence in the last week of the study. Data are mean±s.e.m. Each dot represents one replicate (n=4 in mock-treated group and n=6 in the siRNA-treated group).
Figure 4B:
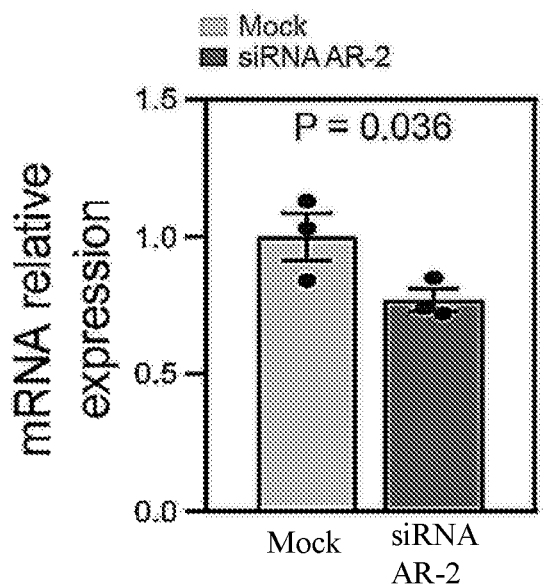
Figure 4C:
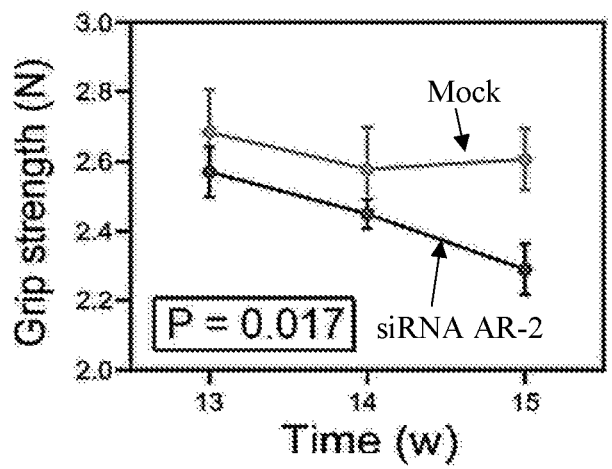
Figure 4D:
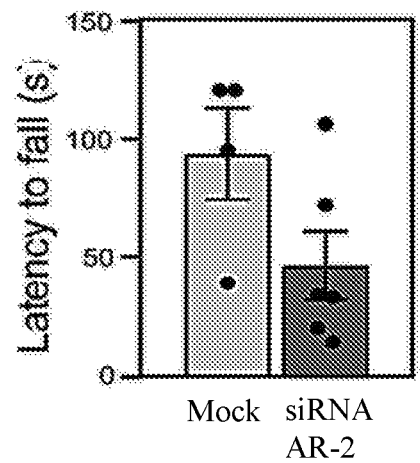

Repetitive subcutaneous injections at 20 mg/kg resulted in sustained reduction in AR2 levels in muscle still 6 weeks after the last injection (FIG. 4a) and determined a worsening of the neuromuscular phenotype (FIG. 4b-d), further confirming that AR2 overexpression is beneficial in SBMA.

In summary, the inventors demonstrate that AR splice variant 2, by heterodimerizing with full length AR and binding to its specific genomic targets, acts as a transcription factor decoy, regulating AR activity. Furthermore, the inventors establish therapeutic modulation of this variant as a new paradigm for treatment of SBMA and other AR-related disorders with high translational potential.

Example 2

To further evaluate the therapeutic capacity of AR splice variant 2 (AR2; also known as AR45), the experiment involving AAV9-AR2 treatment of SBMA mice (n=8) in Example 1 was extended to increase the number of mice to 15 mice per treatment group, a cohort number that is comparable to that of a full scale preclinical trial.

The SBMA mice were injected with AAV9 encoding AR2 cDNA or green fluorescent protein (GFP), or saline, as described in Example 1. The survival, body weight, grip strength and rotarod activity of these mice were observed, as described in Example 1.

Figure 5A:
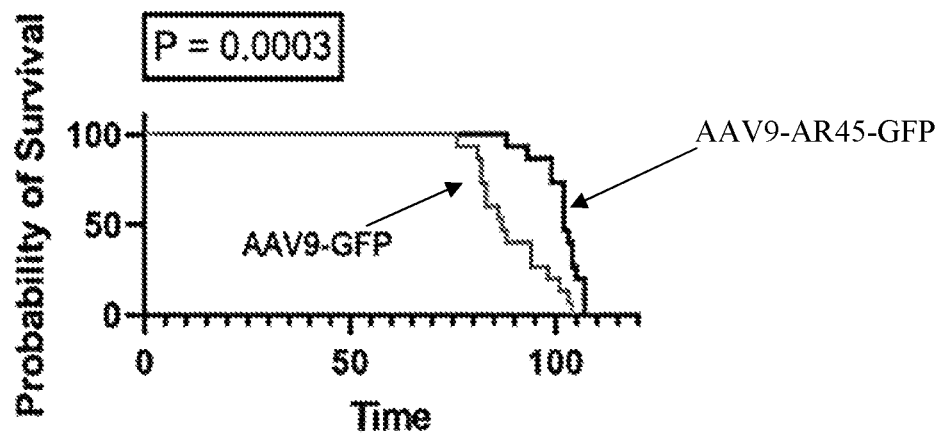
FIG. 5 shows AAV9-AR2 treatment improves the phenotypic outcomes in SBMA mice. a) Survival—Kaplan-Meier survival estimation of SBMA mice (log-rank test). b) Disease onset—Left: Kaplan-Meier estimation of disease onset. Disease onset is defined as time in day when the mice start to exhibit sustained body weight loss for two consecutive weeks. Right: Mean days to onset. c) Body weight—Left: Percentage of body weight from 8 weeks of age to end stage, with mean body weight at week 8 set to 100%. Right: Mean body weight of SBMA mice from the two treatment groups at the age of 13 weeks. d) Grip strength—Percentage of mean grip strength from 8 weeks of age to end stage, with mean grip strength at week 8 set to 100%. e) Mean rotarod activity. AAV9-AR2 is referred to as AAV9-AR45 in the figures.
Figure 5B:
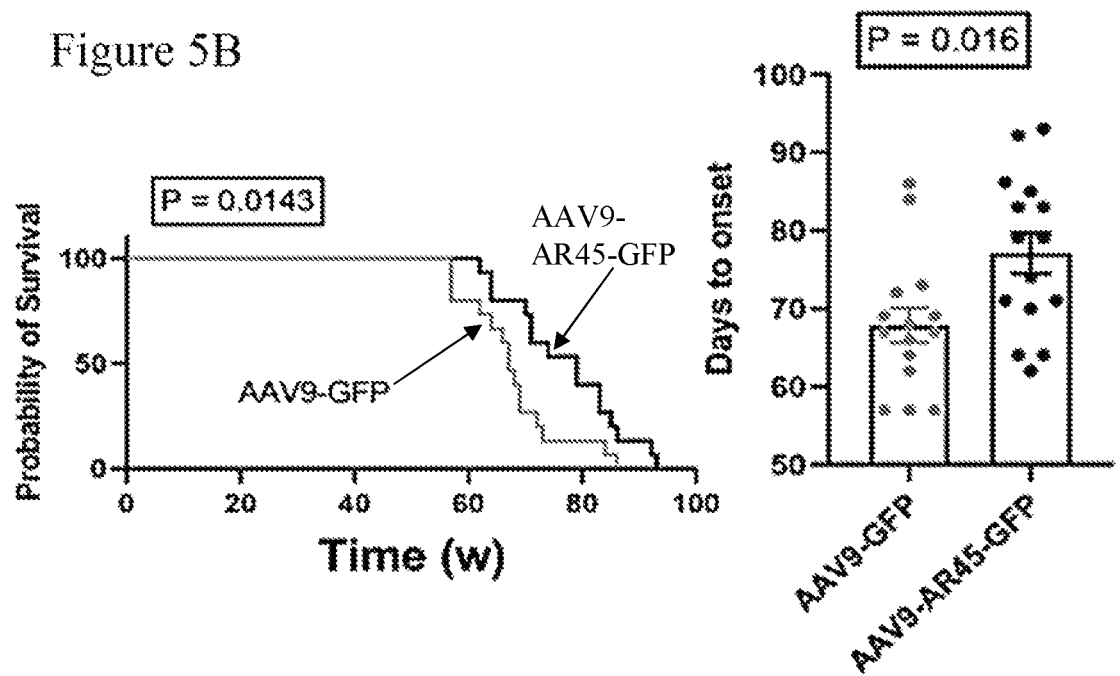
Figure 5C:
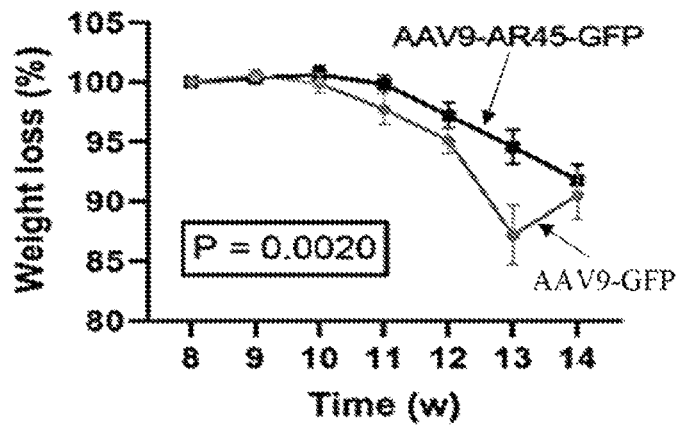
Figure 5C:
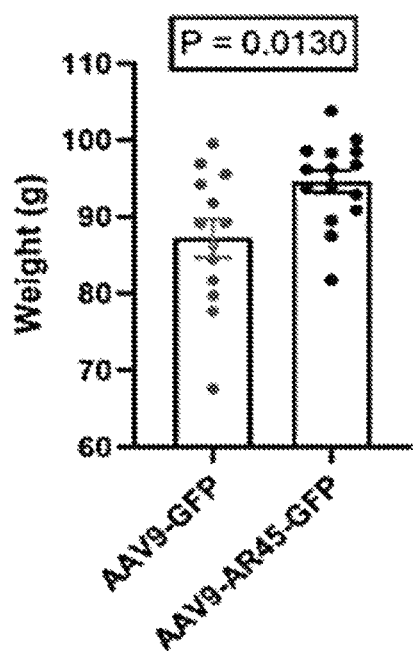
Figure 5D:
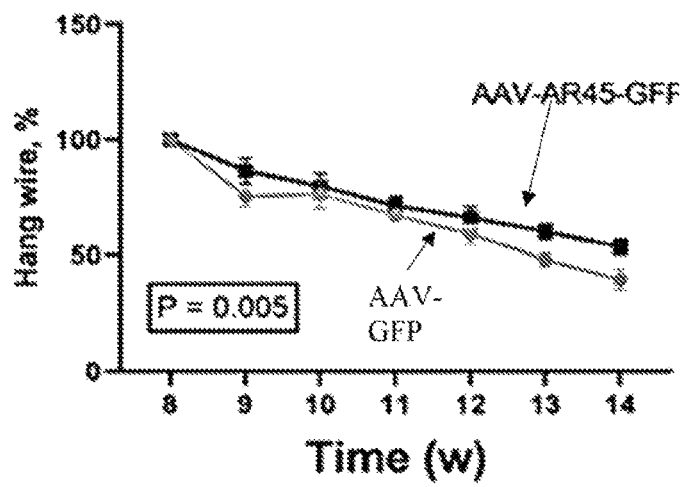
Figure 5E:
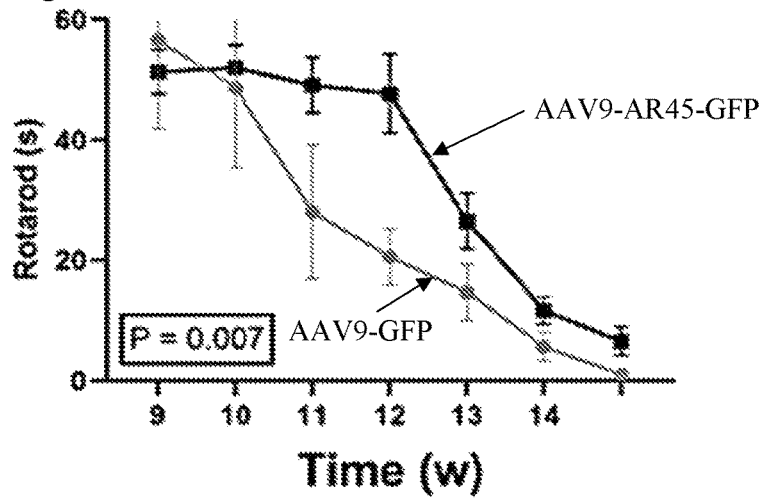

The results show that AAV9-AR2 (referred to as AAV9-AR45 in the figures) treatment of SBMA mice significantly prolonged life span (FIG. 5a), delayed disease onset (FIG. 5b), improved weight loss (FIG. 5c), grip strength (FIG. 5d) and rotarod activity (FIG. 5e).

These results are consistent with the observations in the Example 1, demonstrating that AR2 treatment is capable of ameliorating disease phenotype of SBMA and other AR-related disorders.

REFERENCES

1 Grunseich et al., Lancet Neurol. 2018 December; 17:1043-1052
2 Cunningham et al. Science 244, 1081-1085 (1989)
3 Sambrook et al., Molecular Cloning: A Laboratory Manual, CSH Press 1989, pp. 15.3-15.108
4 Wang et al., Gene Therapy 15, 1489-1499 (2008)
5 Goldspiel et al., Clinical Pharmacy 12:488-505 (1993)
6 Wu and Wu, Biotherapy 3:87-95 (1991)
7 Tolstoshev, Ann. Rev. Pharmacol. Toxicol. 32:573-596 (1993)
8 Mulligan, Science 260:926-932 (1993)
9 Morgan and Anderson, Ann. Rev. Biochem. 62: 191-217 (1993)
10 May, TIBTECH 1 1(5): 155-215 (1993)
11 Ausubel et al. (eds.), Current Protocols in Molecular Biology, John Wiley & Sons, NY (1993)
12 Kriegler, Gene Transfer and Expression, A Laboratory Manual, Stockton Press, NY (1990)
13 Wu and Wu, J Biol. Chem. 262:4429-4432 (1987)
14 WO 92/06180
15 Koller and Smithies, Proc. Natl. Acad. Sci. USA 86:8932-8935(1989)
16 Zijlstra et al., Nature 342:435-438 (1989)
17 WO 94/08598
18 Stemple and Anderson, Cell 71:973-985 (1992)
19 Rheinwald, Meth. Cell Bio. 21A:229 (1980)
20 Pittelkow and Scott, Mayo Clinic Proc. 61:771 (1986)
21 Davey and Grossmann, Clin. Biochem. Rev. 37(1) (2016)
22 Shukla et al., Andrology, 4, 366-381 (2016)
23 Altschul, J Mol Evol. 1993 March; 36(3):290-300
24 Altschul, J Mol Biol. 1990 Oct. 5; 215(3):403-10
25 Henikoff and Henikoff (1992) PNAS 15:10915-9
26 Karlin and Altschul (1993) PNAS 15:5873-7
27 Devereux et al. (1984) Nucleic Acids Res. 12:387-395
28 Schmidt, et al., Methods 48, 240-248 (2009)
29 Burger et al. Nucleic Acids Res. 47, 3467-3484 (2019)
30 Haraszti et al. Nucleic Acids Res. 45, 7581-7592 (2017)
31 Haraszti et al. Nucleic Acids Res. 45, 7581-7592 (2017)
32 Patro et al., Nat. Methods 14, 417-419 (2017)
33 Soneson et al., F1000Research 4, 1521 (2016)
34 Sergushichev et al., bioRxiv 060012 (2016)
35 Turanov et al. Nat. Biotechnol. 36, 1164-1173 (2018)

Sequence Information

SEQ ID NO: 1-the polypeptide sequence of an AR variant
PQKTCLICGDEASGCHYGALTCGSCKVFFKRAAEGKQKYLCASRNDCTIDKFRRK
NCPSCRLRKCYEAGMTLGARKLKKLGNLKLQEEGEASSTTSPTEETTQKLTVSHIE
GYECQPIFLNVLEAIEPGVVCAGHDNNQPDSFAALLSSLNELGERQLVHVVKWAK
ALPGFRNLHVDDQMAVIQYSWMGLMVFAMGWRSFTNVNSRMLYFAPDLVFNEY
RMHKSRMYSQCVRMRHLSQEFGWLQITPQEFLCMKALLLFSIIPVDGLKNQKFFD
ELRMNYIKELDRIIACKRKNPTSCSRRFYQLTKLLDSVQPIARELHQFTFDLLIKSH
MVSVDFPEMMAEIISVQVPKILSGKVKPIYFHTQ

Sequence Information

SEQ ID NO: 2-the cDNA encoding the AR variant of SEQ ID NO: 1
CCCCAGAAGACCTGCCTGATCTGTGGAGATGAAGCTTCTGGGTGTCACTATGG
AGCTCTCACATGTGGAAGCTGCAAGGTCTTCTTCAAAAGAGCCGCTGAAGGGA
AACAGAAGTACCTGTGCGCCAGCAGAAATGATTGCACTATTGATAAATTCCGA
AGGAAAAATTGTCCATCTTGTCGTCTTCGGAAATGTTATGAAGCAGGGATGAC
TCTGGGAGCCCGGAAGCTGAAGAAACTTGGTAATCTGAAACTACAGGAGGAA
GGAGAGGCTTCCAGCACCACCAGCCCCACTGAGGAGACAACCCAGAAGCTGA
CAGTGTCACACATTGAAGGCTATGAATGTCAGCCCATCTTTCTGAATGTCCTGG
AAGCCATTGAGCCAGGTGTAGTGTGTGCTGGACACGACAACAACCAGCCCGAC
TCCTTTGCAGCCTTGCTCTCTAGCCTCAATGAACTGGGAGAGAGACAGCTTGTA
CACGTGGTCAAGTGGGCCAAGGCCTTGCCTGGCTTCCGCAACTTACACGTGGA
CGACCAGATGGCTGTCATTCAGTACTCCTGGATGGGGCTCATGGTGTTTGCCAT
GGGCTGGCGATCCTTCACCAATGTCAACTCCAGGATGCTCTACTTCGCCCCTGA
TCTGGTTTTCAATGAGTACCGCATGCACAAGTCCCGGATGTACAGCCAGTGTGT
CCGAATGAGGCACCTCTCTCAAGAGTTTGGATGGCTCCAAATCACCCCCCAGG
AATTCCTGTGCATGAAAGCACTGCTACTCTTCAGCATTATTCCAGTGGATGGGC
TGAAAAATCAAAAATTCTTTGATGAACTTCGAATGAACTACATCAAGGAACTC
GATCGTATCATTGCATGCAAAAGAAAAAATCCCACATCCTGCTCAAGACGCTT
CTACCAGCTCACCAAGCTCCTGGACTCCGTGCAGCCTATTGCGAGAGAGCTGC
ATCAGTTCACTTTTGACCTGCTAATCAAGTCACACATGGTGAGCGTGGACTTTC
CGGAAATGATGGCAGAGATCATCTCTGTGCAAGTGCCCAAGATCCTTTCTGGG
AAAGTCAAGCCCATCTATTTCCACACCCAGTGA SEQ ID NO: 3-the polypeptide sequence of human AR2 (ENSP00000379358)
MILWLHSLETARDHVLPIDYYFPPQKTCLICGDEASGCHYGALTCGSCKVFFKRAA
EGKQKYLCASRNDCTIDKFRRKNCPSCRLRKCYEAGMTLGARKLKKLGNLKLQE
EGEASSTTSPTEETTQKLTVSHIEGYECQPIFLNVLEAIEPGVVCAGHDNNQPDSFA
ALLSSLNELGERQLVHVVKWAKALPGFRNLHVDDQMAVIQYSWMGLMVFAMG
WRSFTNVNSRMLYFAPDLVFNEYRMHKSRMYSQCVRMRHLSQEFGWLQITPQEF
LCMKALLLFSIIPVDGLKNQKFFDELRMNYIKELDRIIACKRKNPTSCSRRFYQLTK
LLDSVQPIARELHQFTFDLLIKSHMVSVDFPEMMAEIISVQVPKILSGKVKPIYFHT
Q SEQ ID NO: 4-the cDNA sequence of human AR2
ATGATACTCTGGCTTCACAGTTTGGAGACTGCCAGGGACCATGTGTTTGCCCATT
GACTATTACTTTCCACCCCAGAAGACCTGCCTGATCTGTGGAGATGAAGCTTCT
GGGTGTCACTATGGAGCTCTCACATGTGGAAGCTGCAAGGTCTTCTTCAAAAG
AGCCGCTGAAGGGAAACAGAAGTACCTGTGCGCCAGCAGAAATGATTGCACT
ATTGATAAATTCCGAAGGAAAAATTGTCCATCTTGTCGTCTTCGGAAATGTTAT
GAAGCAGGGATGACTCTGGGAGCCCGGAAGCTGAAGAAACTTGGTAATCTGA
AACTACAGGAGGAAGGAGAGGCTTCCAGCACCACCAGCCCCACTGAGGAGAC
AACCCAGAAGCTGACAGTGTCACACATTGAAGGCTATGAATGTCAGCCCATCT
TTCTGAATGTCCTGGAAGCCATTGAGCCAGGTGTAGTGTGTGCTGGACACGAC
AACAACCAGCCCGACTCCTTTGCAGCCTTGCTCTCTAGCCTCAATGAACTGGG
AGAGAGACAGCTTGTACACGTGGTCAAGTGGGCCAAGGCCTTGCCTGGCTTCC
GCAACTTACACGTGGACGACCAGATGGCTGTCATTCAGTACTCCTGGATGGGG
CTCATGGTGTTTGCCATGGGCTGGCGATCCTTCACCAATGTCAACTCCAGGATG
CTCTACTTCGCCCCTGATCTGGTTTTCAATGAGTACCGCATGCACAAGTCCCGG
ATGTACAGCCAGTGTGTCCGAATGAGGCACCTCTCTCAAGAGTTTGGATGGCT
CCAAATCACCCCCCAGGAATTCCTGTGCATGAAAGCACTGCTACTCTTCAGCA
TTATTCCAGTGGATGGGCTGAAAAATCAAAAATTCTTTGATGAACTTCGAATG
AACTACATCAAGGAACTCGATCGTATCATTGCATGCAAAAGAAAAAATCCCAC
ATCCTGCTCAAGACGCTTCTACCAGCTCACCAAGCTCCTGGACTCCGTGCAGCC
TATTGCGAGAGAGCTGCATCAGTTCACTTTTGACCTGCTAATCAAGTCACACAT
GGTGAGCGTGGACTTTCCGGAAATGATGGCAGAGATCATCTCTGTGCAAGTGC
CCAAGATCCTTTCTGGGAAAGTCAAGCCCATCTATTTCCACACCCAGTGA SEQ ID NO: 5-the polypeptide sequence of the NTD of human AR
MEVQLGLGRVYPRPPSKTYRGAFQNLFQSVREVIQNPGPRHPEAASAAPPGASLLL
LQQQQQQQQQQQQQQQQQQQQETSPRQQQQQQGEDGSPQAHRRGPTGYLV
LDEEQQPSQPQSALECHPERGCVPEPGAAVAASKGLPQQLPAPPDEDDSAAPSTLS
LLGPTFPGLSSCSADLKDILSEASTMQLLQQQQQEAVSEGSSSGRAREASGAPTSSK
DNYLGGTSTISDNAKELCKAVSVSMGLGVEALEHLSPGEQLRGDCMYAPLLGVPP
AVRPTPCAPLAECKGSLLDDSAGKSTEDTAEYSPFKGGYTKGLEGESLGCSGSAA
AGSSGTLELPSTLSLYKSGALDEAAAYQSRDYYNFPLALAGPPPPPPPPHPHARIKL
ENPLDYGSAWAAAAAQCRYGDLASLHGAGAAGPGSGSPSAAASSSWHTLFTAEE
GQLYGPCGGGGGGGGGGGGGGGGGGGGEAGAVAPYGYTRPPQGLAGQES
DFTAPDVWYPGGMVSRVPYPSPTCVKSEMGPWMDSYSGPYGDMRLETARDHVL
PIDYYFP SEQ ID NO: 6-the polypeptide sequence of human AR (ENSP00000363822)
MEVQLGLGRVYPRPPSKTYRGAFQNLFQSVREVIQNPGPRHPEAASAAPPGASLLL
LQQQQQQQQQQQQQQQQQQQQETSPRQQQQQQGEDGSPQAHRRGPTGYLV
LDEEQQPSQPQSALECHPERGCVPEPGAAVAASKGLPQQLPAPPDEDDSAAPSTLS
LLGPTFPGLSSCSADLKDILSEASTMQLLQQQQQEAVSEGSSSGRAREASGAPTSSK
DNYLGGTSTISDNAKELCKAVSVSMGLGVEALEHLSPGEQLRGDCMYAPLLGVPP

| Sequence Information |
|---|
| AVRPTPCAPLAECKGSLLDDSAGKSTEDTAEYSPFKGGYTKGLEGESLGCSGSAA
AGSSGTLELPSTLSLYKSGALDEAAAYQSRDYYNFPLALAGPPPPPPPPHPHARIKL
ENPLDYGSAWAAAAAQCRYGDLASLHGAGAAGPGSGSPSAAASSSWHTLFTAEE
GQLYGPCGGGGGGGGGGGGGGGGGGGGGEAGAVAPYGYTRPPQGLAGQES
DFTAPDVWYPGGMVSRVPYPSPTCVKSEMGPWMDSYSGPYGDMRLETARDHVL
PIDYYFPPQKTCLICGDEASGCHYGALTCGSCKVFFKRAAEGKQKYLCASRNDCTI
DKFRRKNCPSCRLRKCYEAGMTLGARKLKKLGNLKLQEEGEASSTTSPTEETTQK
LTVSHIEGYECQPIFLNVLEAIEPGVVCAGHDNNQPDSFAALLSSLNELGERQLVH
VVKWAKALPGFRNLHVDDQMAVIQYSWMGLMVFAMGWRSFTNVNSRMLYFAP
DLVFNEYRMHKSRMYSQCVRMRHLSQEFGWLQITPQEFLCMKALLLFSIIPVDGL
KNQKFFDELRMNYIKELDRIIACKRKNPTSCSRRFYQLTKLLDSVQPIARELHQFTF
DLLIKSHMVSVDFPEMMAEIISVQVPKILSGKVKPIYFHTQ SEQ ID NO: 7-the polypeptide sequence of an AR variant
MEVQLGLGRVYPRPPSKTYRGAFQNLFQSVREVIQNPGPRHPEAASAAPPREASG
APTSSKDNYLGGTSTISDNAKELCKAVSVSMGLGVEALEHLSPGEQLRGDCMYAP
LLGVPPAVRPTPCAPLAECKGSLLDDSAGKSTEDTAEYSPFKGGYTKGLEGESLGC
SGSAAAGSSGTLELPSTLSLYKSGALDEAAAYQSRDYYNFPLALAGPPPPPPPPHPH
ARIKLENPLDYGSAWAAAAAQCRYGDLASLHGAGAAGPGSGSPSAAASSSWHTL
FTAEEGQLYGPCGGGGGGGGGGGGGGGGGGGGGGEAGAVAPYGYTRPPQGLA
GQESDFTAPDVWYPGGMVSRVPYPSPTCVKSEMGPWMDSYSGPYGDMRLETAR
DHVLPIDYYFPPQKTCLICGDEASGCHYGALTCGSCKVFFKRAAEGKQKYLCASR
NDCTIDKFRRKNCPSCRLRKCYEAGMTLGARKLKKLGNLKLQEEGEASSTTSPTE
ETTQKLTVSHIEGYECQPIFLNVLEAIEPGVVCAGHDNNQPDSFAALLSSLNELGER
QLVHVVKWAKALPGFRNLHVDDQMAVIQYSWMGLMVFAMGWRSFTNVNSRM
LYFAPDLVFNEYRMHKSRMYSQCVRMRHLSQEFGWLQITPQEFLCMKALLLFSIIP
VDGLKNQKFFDELRMNYIKELDRIIACKRKNPTSCSRRFYQLTKLLDSVQPIAREL
HQFTFDLLIKSHMVSVDFPEMMAEIISVQVPKILSGKVKPIYFHTQ SEQ ID NO: 8-the polypeptide sequence of an AR variant
REASGAPTSSKDNYLGGTSTISDNAKELCKAVSVSMGLGVEALEHLSPGEQLRGD
CMYAPLLGVPPAVRPTPCAPLAECKGSLLDDSAGKSTEDTAEYSPFKGGYTKGLE
GESLGCSGSAAAGSSGTLELPSTLSLYKSGALDEAAAYQSRDYYNFPLALAGPPPP
PPPPHPHARIKLENPLDYGSAWAAAAAQCRYGDLASLHGAGAAGPGSGSPSAAAS
SSWHTLFTAEEGQLYGPCGGGGGGGGGGGGGGGGGGGGGEAGAVAPYGYT
RPPQGLAGQESDFTAPDVWYPGGMVSRVPYPSPTCVKSEMGPWMDSYSGPYGD
MRLETARDHVLPIDYYFPPQKTCLICGDEASGCHYGALTCGSCKVFFKRAAEGKQ
KYLCASRNDCTIDKFRRKNCPSCRLRKCYEAGMTLGARKLKKLGNLKLQEEGEA
SSTTSPTEETTQKLTVSHIEGYECQPIFLNVLEAIEPGVVCAGHDNNQPDSFAALLSS
LNELGERQLVHVVKWAKALPGFRNLHVDDQMAVIQYSWMGLMVFAMGWRSFT
NVNSRMLYFAPDLVFNEYRMHKSRMYSQCVRMRHLSQEFGWLQITPQEFLCMK
ALLLFSIIPVDGLKNQKFFDELRMNYIKELDRIIACKRKNPTSCSRRFYQLTKLLDS
VQPIARELHQFTFDLLIKSHMVSVDFPEMMAEIISVQVPKILSGKVKPIYFHTQ SEQ ID NOs: 9-34-see Examples for the siRNA sequences (sense and antisense)

SEQ ID NO: 35-polypeptide sequence at the N-terminus of AR2 resulting from the alternative exon 1b
MILWLHS |

The invention claimed is:

1. A method for treatment of spinal and bulbar muscular atrophy (SBMA) in a patient, comprising administering to the patient a therapeutically effective amount of an expression construct encoding androgen receptor splice variant 2 (AR2), wherein the patient is a human patient having expansion of the polyglutamine tract in the N terminus domain (NTD) of androgen receptor (AR), wherein the expansion causes SBMA.

2. The method according to claim 1, wherein the expression construct is a vector derived from an adeno-associated virus (AAV).

3. The method according to claim 1, wherein the AR2 is expressed from a muscle-specific promoter or a motor neuron-specific promoter.

4. A method for treatment of SBMA in a patient, comprising administering to the patient a therapeutically effective amount of a host cell comprising or producing an expression construct encoding AR2, wherein the patient is a human patient having expansion of the polyglutamine tract in the N terminus domain (NTD) of androgen receptor (AR), wherein the expansion causes SBMA.

5. A method for treatment of spinal and bulbar muscular atrophy (SBMA) in a patient, comprising administering to the patient a therapeutically effective amount of a pharmaceutical composition, wherein the pharmaceutical composition comprises a pharmaceutically acceptable carrier and:
   (a) an expression construct encoding AR2, or
   (b) a host cell comprising or producing the expression construct,
   wherein the patient is a human patient having expansion of the polyglutamine tract in the N terminus domain (NTD) of androgen receptor (AR), wherein the expansion causes SBMA.

* * * * *